US012084513B2

(12) United States Patent
Feng et al.

(10) Patent No.: US 12,084,513 B2
(45) Date of Patent: Sep. 10, 2024

(54) ANTI-C1S ANTIBODIES AND METHODS OF USE

(71) Applicant: Chugai Seiyaku Kabushiki Kaisha, Tokyo (JP)

(72) Inventors: Shu Feng, Singapore (SG); Taichi Kuramochi, Singapore (SG); Masaru Muraoka, Singapore (SG); Noriyuki Takahashi, Singapore (SG)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/763,134

(22) PCT Filed: Nov. 14, 2018

(86) PCT No.: PCT/JP2018/042054
§ 371 (c)(1),
(2) Date: May 11, 2020

(87) PCT Pub. No.: WO2019/098212
PCT Pub. Date: May 23, 2019

(65) Prior Publication Data
US 2021/0032365 A1 Feb. 4, 2021

(30) Foreign Application Priority Data

Nov. 14, 2017 (JP) ................ 2017-219507
Oct. 4, 2018 (JP) ................ 2018-188765

(51) Int. Cl.
*C07K 16/40* (2006.01)
*A61K 39/00* (2006.01)

(52) U.S. Cl.
CPC ........ *C07K 16/40* (2013.01); *A61K 2039/505* (2013.01); *C07K 2317/21* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,737,056 B1 | 5/2004 | Presta | |
| 7,317,091 B2 | 1/2008 | Lazar et al. | |
| 7,662,925 B2 | 2/2010 | Lazar et al. | |
| 7,786,270 B2 | 8/2010 | Johnson et al. | |
| 7,960,512 B2 | 6/2011 | Stavenhagen et al. | |
| 8,063,187 B2 | 11/2011 | Chu et al. | |
| 8,101,720 B2 | 1/2012 | Lazar et al. | |
| 8,188,231 B2 | 5/2012 | Lazar et al. | |
| 8,193,318 B2 | 6/2012 | Koenig et al. | |
| 8,388,955 B2 | 3/2013 | Lazar et al. | |
| 8,410,328 B2 | 4/2013 | Chung et al. | |
| 8,551,485 B2 | 10/2013 | Bernett et al. | |
| 8,652,466 B2 | 2/2014 | Stavenhagen et al. | |
| 8,685,725 B2 | 4/2014 | Beliard et al. | |
| 8,735,545 B2 | 5/2014 | Lazar et al. | |
| 8,802,820 B2 | 8/2014 | Chamberlain et al. | |
| 8,802,823 B2 | 8/2014 | Lazar et al. | |
| 8,945,562 B2 * | 2/2015 | Van Vlasselaer ....... A61P 25/00 530/387.3 |
| 9,029,515 B2 | 5/2015 | Pons et al. | |
| 9,051,373 B2 | 6/2015 | Lazar et al. | |
| 9,079,949 B1 | 7/2015 | Andrien, Jr. et al. | |
| 9,107,861 B1 | 8/2015 | Andrien, Jr. et al. | |
| 9,334,334 B2 | 5/2016 | McWhirter et al. | |
| 9,540,449 B2 | 1/2017 | Yancopoulos et al. | |
| 9,644,018 B2 | 5/2017 | Stevis et al. | |
| 9,648,856 B2 | 5/2017 | McWhirter et al. | |
| 9,790,273 B2 | 10/2017 | Murphy et al. | |
| 9,890,218 B2 | 2/2018 | Mimoto et al. | |
| 9,920,134 B2 | 3/2018 | Jackson et al. | |
| 10,000,560 B2 | 6/2018 | Ruike et al. | |
| 10,111,953 B2 | 10/2018 | Swergold et al. | |
| 10,618,965 B2 | 4/2020 | Igawa et al. | |
| 10,766,960 B2 | 9/2020 | Igawa et al. | |
| 10,919,953 B2 | 2/2021 | Katada et al. | |
| 11,142,563 B2 | 10/2021 | Igawa et al. | |
| 11,236,168 B2 | 2/2022 | Igawa et al. | |
| 11,267,868 B2 | 3/2022 | Mimoto et al. | |
| 2004/0001822 A1 | 1/2004 | Levanon et al. | |
| 2004/0001839 A1 | 1/2004 | Levanon et al. | |
| 2004/0002450 A1 | 1/2004 | Lazarovits et al. | |
| 2004/0110226 A1 | 6/2004 | Lazar et al. | |

(Continued)

FOREIGN PATENT DOCUMENTS

AU  2012222252 A1  10/2013
AU  2012222252 B2  8/2016

(Continued)

OTHER PUBLICATIONS

"An Introduction to Antibodies:Antibody-Antigen Interaction" MilliporeSigma [online]2022 Merck KGaA, Darmstadt, Germany, [retrieved on Mar. 11, 2022]. Retrieved from Internet: <URL: https://www.sigmaaldrich.com/us/en/technical-documents/technical-article/protein-biology/elisa/antibody-antigen-interaction> (Year: 2022).*

(Continued)

*Primary Examiner* — Sharon X Wen
(74) *Attorney, Agent, or Firm* — Nixon & Vanderhye P.C.

(57) ABSTRACT

The invention provides anti-C1s antibodies and methods of using the same. The affinities of the antibodies to C1s depend on pH and other conditions. The invention also provides pharmaceutical formulations comprising the antibodies, and methods of treating an individual having a complement-mediated disease or disorder comprising administering the antibody to the individual. In addition, the binding affinity of the antibody at high and low pH was measured, and mice PK study was conducted on the antibodies, and pharmacokinetics parameters of the antibodies were evaluated in this application.

18 Claims, 2 Drawing Sheets
Specification includes a Sequence Listing.

(56) References Cited

U.S. PATENT DOCUMENTS

| | | |
|---|---|---|
| 2004/0132101 A1 | 7/2004 | Lazar et al. |
| 2005/0032114 A1 | 2/2005 | Hinton et al. |
| 2005/0054832 A1 | 3/2005 | Lazar et al. |
| 2005/0064514 A1 | 3/2005 | Stavenhagen et al. |
| 2005/0260213 A1 | 11/2005 | Koenig et al. |
| 2006/0024298 A1 | 2/2006 | Lazar et al. |
| 2007/0003546 A1 | 1/2007 | Lazar et al. |
| 2007/0009523 A1 | 1/2007 | Presta |
| 2007/0231329 A1 | 10/2007 | Lazar et al. |
| 2007/0248602 A1 | 10/2007 | Lazar et al. |
| 2008/0044417 A1 | 2/2008 | Johnson et al. |
| 2008/0138349 A1 | 6/2008 | Stavenhagen et al. |
| 2008/0181890 A1 | 7/2008 | Lazar et al. |
| 2008/0199471 A1 | 8/2008 | Bernett et al. |
| 2008/0206867 A1 | 8/2008 | Desjarlais et al. |
| 2009/0035836 A1 | 2/2009 | Datta et al. |
| 2009/0041770 A1 | 2/2009 | Chamberlain et al. |
| 2009/0053211 A9 | 2/2009 | Lazar et al. |
| 2009/0053240 A1 | 2/2009 | Lazar et al. |
| 2009/0076251 A1 | 3/2009 | Koenig et al. |
| 2009/0136485 A1 | 5/2009 | Chu et al. |
| 2010/0098730 A1 | 4/2010 | Lowman et al. |
| 2010/0184959 A1 | 7/2010 | Guler-Gane et al. |
| 2010/0249482 A1 | 9/2010 | Chung et al. |
| 2011/0021755 A1 | 1/2011 | Lazar et al. |
| 2011/0027276 A1 | 2/2011 | Bernett et al. |
| 2011/0111406 A1 | 5/2011 | Igawa et al. |
| 2011/0223658 A1 | 9/2011 | Beliard et al. |
| 2011/0229489 A1 | 9/2011 | Pons et al. |
| 2012/0093818 A1 | 4/2012 | Jackson et al. |
| 2013/0085265 A1 | 4/2013 | Jackson et al. |
| 2013/0131319 A1 | 5/2013 | Igawa et al. |
| 2013/0209457 A1 | 8/2013 | Lazar et al. |
| 2013/0247234 A1 | 9/2013 | McWhirter et al. |
| 2013/0259876 A1 | 10/2013 | Murphy et al. |
| 2014/0044730 A1 | 2/2014 | Yancopoulos et al. |
| 2014/0073768 A1 | 3/2014 | Lazar et al. |
| 2014/0082760 A1 | 3/2014 | McWhirter et al. |
| 2014/0093496 A1 | 4/2014 | Mimoto et al. |
| 2014/0105889 A1 | 4/2014 | Igawa et al. |
| 2014/0199294 A1 | 7/2014 | Mimoto et al. |
| 2014/0234340 A1 | 8/2014 | Igawa et al. |
| 2014/0271617 A1 | 9/2014 | Igawa et al. |
| 2014/0335089 A1 | 11/2014 | Igawa et al. |
| 2014/0356371 A1 | 12/2014 | Swergold et al. |
| 2015/0166636 A1 | 6/2015 | Igawa et al. |
| 2015/0166654 A1 | 6/2015 | Igawa et al. |
| 2015/0203577 A1 | 7/2015 | Igawa et al. |
| 2015/0210763 A1 | 7/2015 | Kuramochi et al. |
| 2015/0252107 A1 | 9/2015 | Stevis et al. |
| 2015/0299296 A1 | 10/2015 | Katada et al. |
| 2015/0299313 A1 | 10/2015 | Igawa et al. |
| 2015/0344570 A1 | 12/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0053023 A1 | 2/2016 | Rosenthal et al. |
| 2016/0090425 A1* | 3/2016 | Rosenthal ............... C07K 16/40 435/7.1 |
| 2016/0176954 A1 | 6/2016 | Ruike et al. |
| 2016/0200807 A1* | 7/2016 | Ruike ....................... A61P 9/04 424/139.1 |
| 2016/0326237 A1 | 11/2016 | Rosenthal et al. |
| 2018/0319877 A1 | 11/2018 | Ruike et al. |
| 2019/0112393 A1 | 4/2019 | Igawa et al. |
| 2020/0230834 A1 | 11/2020 | Koga |
| 2021/0261648 A1 | 8/2021 | Katada et al. |
| 2023/0140797 A1 | 5/2023 | Igawa et al. |

FOREIGN PATENT DOCUMENTS

| | | |
|---|---|---|
| CA | 2827923 A1 | 8/2012 |
| CN | 1763097 A | 4/2006 |
| CN | 101001873 A | 7/2007 |
| CN | 101014619 A | 8/2007 |
| CN | 101014619 B | 11/2010 |
| CN | 101932593 A | 12/2010 |
| CN | 1763097 B | 4/2011 |
| CN | 102056946 A | 5/2011 |
| CN | 102149729 A | 8/2011 |
| CN | 102633880 A | 8/2012 |
| CN | 102666584 A | 9/2012 |
| CN | 101001873 B | 3/2013 |
| CN | 103492565 A | 1/2014 |
| CN | 103958547 A | 7/2014 |
| CN | 102633880 B | 2/2015 |
| CN | 104884088 B | 6/2018 |
| CN | 108348600 A | 7/2018 |
| CN | 108948197 A | 12/2018 |
| EA | 004317 B1 | 2/2004 |
| EP | 2275443 A1 | 1/2011 |
| EP | 2368911 A1 | 9/2011 |
| EP | 2409990 A | 1/2012 |
| EP | 2647706 A1 | 10/2013 |
| EP | 2679681 A | 1/2014 |
| EP | 2698431 A1 | 2/2014 |
| EP | 2762166 A1 | 8/2014 |
| EP | 2762493 A1 | 8/2014 |
| EP | 2765192 A1 | 8/2014 |
| EP | 2818183 A1 | 12/2014 |
| EP | 2889377 A1 | 7/2015 |
| EP | 2275443 B1 | 12/2015 |
| EP | 2679681 B1 | 8/2019 |
| EP | 2698431 B1 | 9/2020 |
| JP | 2003512019 A | 4/2003 |
| JP | 2006512407 A | 4/2006 |
| JP | 2007532139 A | 11/2007 |
| JP | 2008505174 A | 2/2008 |
| JP | 2008511292 A | 4/2008 |
| JP | 2009511067 A | 3/2009 |
| JP | 2010514460 A | 5/2010 |
| JP | 4580340 B2 | 11/2010 |
| JP | 5055603 B2 | 10/2012 |
| JP | 2013539361 A | 10/2013 |
| JP | 5357778 B2 | 12/2013 |
| JP | 5367982 B2 | 12/2013 |
| JP | 2014514345 A | 6/2014 |
| JP | 2016503400 A | 2/2016 |
| JP | 2016505240 A | 2/2016 |
| JP | 5953303 B2 | 7/2016 |
| JP | 6024025 B2 | 11/2016 |
| JP | 6227191 B1 | 11/2017 |
| JP | 2017535244 A | 11/2017 |
| JP | 6543572 B2 | 7/2019 |
| JP | 2021508441 A | 3/2021 |
| KR | 20110004435 A | 1/2011 |
| RU | 2236222 C2 | 9/2004 |
| RU | 2005112742 A | 1/2006 |
| RU | 2005137578 A | 6/2007 |
| RU | 2325186 C2 | 5/2008 |
| RU | 2337107 C2 | 10/2008 |
| RU | 2008104038 A | 8/2009 |
| RU | 2390527 C2 | 5/2010 |
| SG | 192945 A1 | 9/2013 |
| TW | 201202419 A | 1/2012 |
| WO | WO 9734631 A1 | 9/1997 |
| WO | WO-9958572 A1 | 11/1999 |
| WO | WO-0015214 A1 | 3/2000 |
| WO | WO-0042072 A2 | 7/2000 |
| WO | WO-0170968 A2 | 9/2001 |
| WO | WO0177342 A1 | 10/2001 |
| WO | WO-2004029207 A2 | 4/2004 |
| WO | WO-2004099249 A2 | 11/2004 |
| WO | WO 2005047327 A2 | 5/2005 |
| WO | WO-2005056606 A2 | 6/2005 |
| WO | WO-2005059106 A2 | 6/2005 |
| WO | WO-2005115452 A2 | 12/2005 |
| WO | WO-2006019447 A1 | 2/2006 |
| WO | WO-2006020114 A2 | 2/2006 |
| WO | WO-2006023403 A2 | 3/2006 |
| WO | WO-2006023420 A2 | 3/2006 |
| WO | WO-2006047350 A2 | 5/2006 |
| WO | WO-2006076594 A2 | 7/2006 |

(56) References Cited

FOREIGN PATENT DOCUMENTS

| | | |
|---|---|---|
| WO | WO 2006130834 A2 | 12/2006 |
| WO | WO-2007022520 A2 | 2/2007 |
| WO | WO-2007024249 A2 | 3/2007 |
| WO | WO-2007041635 A2 | 4/2007 |
| WO | WO-2007047578 A2 | 4/2007 |
| WO | WO-2008002933 A2 | 1/2008 |
| WO | WO-2008091954 A2 | 7/2008 |
| WO | WO 2008150494 A1 | 12/2008 |
| WO | WO-2009062083 A2 | 5/2009 |
| WO | WO 2009095235 A | 8/2009 |
| WO | WO 2009125825 A1 | 10/2009 |
| WO | WO 2009131702 A | 10/2009 |
| WO | WO-2009139822 A1 | 11/2009 |
| WO | WO-2009155513 A2 | 12/2009 |
| WO | WO-2010058860 A1 | 5/2010 |
| WO | WO-2010077854 A1 | 7/2010 |
| WO | WO-2010107109 A1 | 9/2010 |
| WO | WO2010131185 A1 | 11/2010 |
| WO | WO-2010136831 A1 | 12/2010 |
| WO | WO 2011008517 A2 | 1/2011 |
| WO | WO-2011091078 A2 | 7/2011 |
| WO | WO 2011111007 A2 | 9/2011 |
| WO | WO-2011122011 A2 | 10/2011 |
| WO | WO2012016227 A2 | 2/2012 |
| WO | WO-2012044831 A1 | 4/2012 |
| WO | WO-2012073992 A1 | 6/2012 |
| WO | WO-2012115241 A1 | 8/2012 |
| WO | WO-2012132067 A1 | 10/2012 |
| WO | WO-2012133782 A1 | 10/2012 |
| WO | WO-2012151199 A1 | 11/2012 |
| WO | WO2013046704 A | 4/2013 |
| WO | WO-2013047729 A1 | 4/2013 |
| WO | WO-2013047748 A1 | 4/2013 |
| WO | WO-2013047752 A1 | 4/2013 |
| WO | WO-2013125667 A1 | 8/2013 |
| WO | WO-2013138681 A1 | 9/2013 |
| WO | WO-2013180200 A1 | 12/2013 |
| WO | WO-2013192240 A2 | 12/2013 |
| WO | WO-2014030728 A1 | 2/2014 |
| WO | WO-2014030750 A1 | 2/2014 |
| WO | WO 2014066744 A2 | 5/2014 |
| WO | WO 2014071206 A1 | 5/2014 |
| WO | WO-2014140366 A1 | 9/2014 |
| WO | WO-2014144080 A2 | 9/2014 |
| WO | WO-2014144577 A1 | 9/2014 |
| WO | WO-2014150983 A2 | 9/2014 |
| WO | WO-2014163101 A1 | 10/2014 |
| WO | WO-2014164959 A2 | 10/2014 |
| WO | WO-2014186599 A2 | 11/2014 |
| WO | WO2015006504 A1 | 1/2015 |
| WO | WO-2015006507 A1 | 1/2015 |
| WO | WO-2015042250 A1 | 3/2015 |
| WO | WO-2015077491 A1 | 5/2015 |
| WO | WO-2015134894 A1 | 9/2015 |
| WO | WO-2016073685 A1 | 5/2016 |
| WO | WO2016125495 A1 | 8/2016 |
| WO | WO-2016164358 A1 | 10/2016 |
| WO | WO2016210172 A1 | 12/2016 |
| WO | WO-2017091719 A1 | 6/2017 |
| WO | WO2017129737 A1 | 8/2017 |
| WO | WO2018071676 A1 | 4/2018 |
| WO | WO-2019098212 A1 | 5/2019 |
| WO | WO 2019198807 A1 | 10/2019 |
| WO | WO2020230834 A1 | 11/2020 |
| WO | WO-2021075479 A1 | 4/2021 |
| WO | WO2022220275 A1 | 10/2022 |

OTHER PUBLICATIONS

Lloyd et al. (Protein Engineering, Design & Selection 2009, 22:159-168) (Year: 2009).*
Schroeder et al. (J Allergy Clin Immunol 2010, 125:S41-S52) (Year: 2010).*
Arlaud, G. J., et al., "A Study on the Structure and Interactions of the C1 Sub-Components C1r and C1s in the Fluid Phase," Biochim Biophys Acta, 616:105-115 (1980).
Edwards, B. M., et al., "The Remarkable Flexibility of the Human Antibody Repertoire; Isolation of Over One Thousand Different Antibodies to a Single Protein, BLyS," J Mol Biol., 334:103-118 (2003).
Flores, M., et al., "Dominant Expression of the Inhibitory FcγRIIB Prevents Antigen Presentation by Murine Plasmacytoid Dendritic Cells," J Immunol., 183:7129-7139 (2009).
Howard, G. and Kaser, M., editors, "Making and Using Antibodies: A Practical Handbook," CRC Press, Taylor & Francis Group, 157-177 (2006).
Igawa, T., et al., "Antibody recycling by engineered pH-dependent antigen binding improves the duration of antigen neutralization," Nat Biotechnol., 28(11):1203-1207 (2010).
Kim, H.-Y., et al., "Affinity Maturation of Monoclonal Antibodies by Multi-Site-Directed Mutagenesis," Meth Mol Biol., 1131:407-420 (2014).
King, D. J., "Applications and Engineering of Monoclonal Antibodies," Taylor & Francis, 151-159, 162-164 (2005).
Lloyd, C., et al., "Modelling the human immune response: performance of a $10^{11}$ human antibody repertoire against a broad panel of therapeutically relevant antigens," Protein Eng Des Sel., 22(3):159-168 (2009).
Matsumoto, M. and Nagaki, K., "Functional Analysis of Activated C1s, a Subcomponent of the First Component of Human Complement, by Monoclonal Antibodies," J Immunol., 137(9):2907-2912 (1986).
Mendez-Fernandez, Y. V., et al., "The inhibitory FcγRIIb modulates the inflammatory response and influences atherosclerosis in male $apoE^{-/-}$ mice," Atherosclerosis, 214(1):73-80 (2011).
Mortensen, S. A., et al., "Structure and activation of C1, the complex initiating the classical pathway of the complement cascade," PNAS, 114(5):986-991 (2017).
Pakula, A. A. and Sauer, R. T., "Genetic Analysis of Protein Stability and Function," Annu Rev Genet., 23:289-310 (1989).
Petillot, Y., et al., "Analysis of the N-linked oligosaccharides of human C1s using electrospray ionization mass spectrometry," FEBS Lett., 358:323-328 (1995).
Poosarla, V. G., et al., "Computational de novo Design of Antibodies binding to a Peptide with High Affinity," Biotechnol Bioeng., 114(6):1331-1342 (2017).
Rivas, G., et al., "Calcium-Linked Self-Association of Human Complement C1s," Biochem., 31:11707-11712 (1992).
Roitt, I., et al., "Immunology," Moscow: Mir, 373-374 (2000).
Rossi, V., et al., "Classical Complement Pathway Components C1r and C1s: Purification from Human Serum and in Recombinant Form and Functional Characterization," Meth Mol Biol., 1100:43-60 (2014).
Rudikoff, S., et al., "Single amino acid substitution altering antigen-binding specificity," PNAS, 79:1979-1983 (1982).
Shi, J., et al., "TNT003, an inhibitor of the serine protease C1s, prevents complement activation induced by cold agglutinins," Blood, 123(26):4015-4022 (2014).
Singer, Genes and Genomes, Moscow, Mir, 115-188 (1998).
Tackenberg, B., et al., "Impaired inhibitory Foy receptor IIB expression on B cells in chronic inflammatory demyelinating polyneuropathy," PNAS, 106(12):4788-4792 (2009).
Torres, M. and Casadevall, A., "The immunoglobulin constant region contributes to affinity and specificity," Trends Immunol., 29(2):91-97 (2008).
Wang, G., et al., "Molecular Basis of Assembly and Activation of Complement Component C1 in Complex with Immunoglobulin G1 and Antigen," Mol Cell, 63:135-145 (2016).
Yarilin, A. A., Fundamentals of Immunology (Osnovy immunologii), Moscow, Medicina, 172-174 (1999).
Yarilin, A. A., Fundamentals of Immunology (Osnovy immunologii), Moscow, Medicina, 171 (1999).
U.S. Appl. No. 17/028,210, 371(c) date Sep. 22, 2020, Katada et al., related application.
U.S. Appl. No. 17/046,395, 371(c) date Oct. 9, 2020, Fukuzawa et al., related application.

(56) References Cited

OTHER PUBLICATIONS

U.S. Appl. No. 17/028,210, 371(c) date Sep. 22, 2020, Katada et al.
U.S. Appl. No. 17/046,395, 371(c) date Oct. 9, 2020, Fukuzawa et al.
U.S. Appl. No. 14/001,218, filed Dec. 2, 2013, Mimoto, et al.
U.S. Appl. No. 14/347,321, filed Sep. 28, 2012, Igawa, et al.
U.S. Appl. No. 14/379,825, filed Feb. 22, 2013, Igawa, et al.
U.S. Appl. No. 14/422,207, filed Aug. 23, 2013, Igawa, et al.
U.S. Appl. No. 14/423,269, filed Aug. 23, 2013, Katada, et al.
U.S. Appl. No. 14/781,069, filed Apr. 2, 2014, Mimoto, et al.
U.S. Appl. No. 15/977,757, filed May 11, 2018, Igawa, et al.
U.S. Appl. No. 17/561,207, filed Dec. 23, 2021, Igawa et al.
U.S. Appl. No. 17/610,204, filed Nov. 10, 2021, Koga.
U.S. Appl. No. 17/671,185, filed Feb. 14, 2022, Mimoto et al.
U.S. Appl. No. 17/768,053, filed Apr. 11, 2022, Koga et al.
U.S. Appl. No. 17/846,672, filed Jun. 22, 2022, Mimoto et al.
U.S. Appl. No. 17/854,023, filed Jun. 30, 2022, Igawa et al.
Abdiche, Y.N., et al., "Antibodies Targeting Closely Adjacent or Minimally Overlapping Epitopes Can Displace One Another," PLoS One 12(1):e0169535 (2017).
Almitairi, J.O.M., et al., "Structure of the C1r-C1s Interaction of the C1 Complex of Complement Activation," Proceedings of the National Academy of Sciences of the United States of America 115(4):768-773 (2018).
Amigorena, S., et al., "FcγRII expression in resting and activated B lymphocytes," Eur J Immunol., 19:1379-1385 (1989).
Amigorena, S., et al., "Cytoplasmic Domain Heterogeneity and Functions of IgG Fc Receptors in B Lymphocytes," Science, 256:1808-1812 (1992).
Armour, K. L., "Differential binding to human FcγRIIa and FcγRIIb receptors by human IgG wildtype and mutant antibodies," Mol Immunol., 40:585-593 (2003).
Bally, I., et al., "Identification of the C1q-Binding Sites of Human C1r and C1s: A Refined Three-Dimensional Model of the C1 Complex of Complement," The Journal of Biological Chemistry 284(29):19340-19348 (2009).
Blank, M. C., et al., "Decreased transcription of the human FCGR2B gene mediated by the-343 G/C promoter polymorphism and association with systemic lupus erythematosus," Hum Genet., 117:220-227 (2005).
Bonvin, P., et al., "De novo isolation of antibodies with pH-dependent binding properties," mAbs, 7(2):294-302 (2015).
Boruchov, A. M., et al., Activating and inhibitory IgG Fc receptors on human DCs mediate opposing functions, J Clin Invest., 115(10):2914-2923 (2005).
Boumpas, D. T., et al., "A Short Course of BG9588 (Anti-CD40 Ligand Antibody) Improves Serologic Activity and Decreases Hematuria in Patients With Proliferative Lupus Glomerulonephritis," Arth Rheum., 48(3):719-727 (2003).
Bruhns, P., et al., "Specificity and affinity of human Fcγreceptors and their polymorphic variants for human IgG subclasses," Blood, 113:3716-3725 (2009).
Bruhns, P., "Properties of mouse and human IgG receptors and their contribution to disease models," Blood, 119(24):5640-5649 (2012).
Burmeister, W. P., et al., "Crystal structure of the complex of rat neonatal Fc receptor with Fc," Nature, 372:379-383 (1994).
Cartron, G., et al., "Therapeutic activity of humanized anti-CD20 monoclonal antibody and polymorphism in IgG Fc receptor FcγRIIIa gene," Blood, 99:754-758 (2002).
Cemerski, S., et al., "Suppression of mast cell degranulation through a dual-targeting tandem IgE-IgG Fc domain biologic engineered to bind with high affinity to FcγRIIb," Immunol Lett., 143:34-43 (2012).
Chaparro-Riggers, J., et al., "Increasing Serum Half-life and Extending Cholesterol Lowering in Vivo by Engineering Antibody with pH-sensitive Binding to PCSK9," J Biol Chem 287(14):11090-11097 (2012).
Chen, J.-Y., et al., "Association of a Transmembrane Polymorphism of Fcγ Receptor IIb (FCGR2B) With Systemic Lupus Erythematosus in Taiwanese Patients," Arth Rheum., 54(12):3908-3917 (2006).
Chu, S. Y., et al., "Inhibition of B cell receptor-mediated activation of primary human B cells by coengagement of CD19 and FcγRIIb with Fc-engineered antibodies," Mol Immunol., 45:3926-3933 (2008).
Chu, S. Y., et al., "Reduction of total IgE by targeted coengagement of IgE B-cell receptor and FcγRIIb with Fc-engineered antibody," J Allergy Clin Immunol., 129(4):1102-1115 (2012).
Chuntharapai, A., et al., "Isotype-Dependent Inhibition of Tumor Growth In Vivo by Monoclonal Antibodies to Death Receptor 4," J Immunol, 166:4891-4898 (2001).
Clark, R., "IgG Effector Mechanisms," Chemical Immunology, 65:88-110 (1997).
Clynes, R., et al., "Fc Receptors Are Required in Passive and Active Immunity to Melanoma," Proc Natl Acad Sci., 95:652-656 (1998).
Clynes, R.A., et al., "Inhibitory Fc receptors modulate in vivo cytotoxicity against tumor targets," Nature Medicine 6(4):443-446 (2000).
Crowe, J. S., et al., "Humanized monoclonal antibody CAMPATH-1H: myeloma cell expression of genomic constructs, nucleotide sequence of cDNA constructs and comparison of effector mechanisms of myeloma and Chinese hamster ovary cell-derived material," Clin Exp Immunol., 87:105-110 (1992).
Dall' Acqua, W. F., et al., "Increasing the Affinity of a Human IgG1 for the Neonatal Fc Receptor: Biological Consequences," J Immunol 169:5171-5180 (2002).
Datta-Mannan, A., et al., "Monoclonal Antibody Clearance—Impact of Modulating the Interaction of IgG With the Neonatal Fc Receptor," J Biol Chem., 282(3):1709-1717 (2007).
Desai, D.D., et al., "Fc Gamma Receptor IIB on Dendritic Cells Enforces Peripheral Tolerance by Inhibiting Effector T Cell Responses," 178(10):6217-6226 (2007).
Dhodapkar, K. M., et al., "Selective blockade of inhibitory Fcγ receptor enables human dendritic cell maturation with IL-12p70 production and immunity to antibody-coated tumor cells," PNAS, 102(8):2910-2915 (2005).
Diamond, B. and Scharff, M. D., "Somatic mutation of the T15 heavy chain gives rise to an antibody with autoantibody specificity," Proc Natl Acad Sci., 81:5841-5844 (1984).
Duffau, P., et al., "Platelet CD154 Potentiates Interferon-a Secretion by Plasmacytoid Dendritic Cells in Systemic Lupus Erythematosus," Sci Transl Med., 2(47):47ra63 (2010).
Examination Report No. 1 for Australian Patent Application 2013306700 dated Jun. 7, 2018.
Fillipovic, "Biochemical basis of human life activity," VLADOS, 38-43 (2005).
Fillipovich, "Biochemical basis of human life," VLADOS, 49-50 (2005).
Floto, R. A., et al., "Loss of function of a lupus-associated FcγRIIb polymorphism through exclusion from lipid rafts," Nat Med., 11(10):1056-1058 (2005).
Fournier, E. M., et al., "Activation of Human Peripheral IgM+ B Cells Is Transiently Inhibited by BCR-Independent Aggregation of FcγRIIB," J Immunol., 181:5350-5359 (2008).
Fukuzawa, T., et al., "Long lasting neutralization of C5 by SKY59, a novel recycling antibody, is a potential therapy for complement-mediated diseases," Sci Rep., 7:1080 (2017).
Gal, P., et al., "Early Complement Proteases: C1r, C1s and MASPs. A Structural Insight into Activation and Functions," Molecular Immunology, 46(14):2745-2752 (2009).
Ghetie, V., et al., "Increasing the serum persistence of an IgG fragment by random mutagenesis," Nature Biotechnol 15:637-640 (1997).
Greenwood, J., et al., "Structural motifs involved in human IgG antibody effector functions," Eur J Immunol., 23:1098-1104 (1993).
Hanson, C. V., et al., "Catalytic antibodies and their applications," Curr Opin Biotechnol., 16:631-636 (2005).
Hasemann, C. A. and Capra, J. D., "Mutational Analysis of Arsonate Binding by a $CRI_{A+}$ Antibody," J Biol Chem., 266(12):7626-7632 (1991).
Henne, K. R., et al., "Anti-PCSK9 Antibody Pharmacokinetics and Low-Density Lipoprotein-Cholesterol Pharmacodynamics in Non-human Primates Are Antigen Affinity-Dependent and Exhibit Limited Sensitivity to Neonatal Fc Receptor-Binding Enhancement," J Pharmacol Exp Ther., 353(1):119-131 (2015).

(56) References Cited

OTHER PUBLICATIONS

Heyman, B., "Feedback regulation by IgG antibodies," Immunol Lett., 88:157-161 (2003).
Hinton, P. R., et al., "An Engineered Human IgG1 Antibody with Longer Serum Half-Life," J Immunol 176:346-356 (2006).
Hjelm, F., et al., "Antibody-Mediated Regulation of the Immune Response," Scand J Immunol., 64:177-184 (2006).
Horton, H. M., et al., "Potent In vitro and In vivo Activity and an Fc-Engineered Anti-CD19 Monoclonal Antibody against Lymphoma and Leukemia," Cancer Res., 68(19):8049-8057 (2008).
Idusogie, E.E., et al., "Engineered Antibodies with Increased Activity to Recruit Complement," J Immunol., 166(4):2571-2575 (2001).
Idusogie, E.E., et al., "Mapping of the C1q Binding Site on Rituxan, A Chimeric Antibody with a Human IgG1 Fc," J Immunol., 164(8):4178-4184 (2000).
Igawa, T., et al., "Reduced elimination of IgG antibodies by engineering the variable region," Protein Eng Des Sel 23(5):385-392 (2010).
Igawa, T., et al., "Sweeping antibody as a novel therapeutic antibody modality capable of eliminating soluble antigens from circulation," Immunol Rev., 270:132-151 (2016).
Ito, W., et al., "The His-probe method: effects of histidine residues introduced into the complementarity-determining regions of antibodies on antigen-antibody interactions at different pH values," FEBS Letters 309(1):85-88 (1992).
Jaeger, "Clinical Immunology and Allergology," 2nd edition, M.: Medicina, 2:484-485 (1990).
James, L. C., et al., "1.9 A Structure of the Therapeutic Antibody CAMPATH-1H Fab in Complex with a Synthetic Peptide Antigen," J Mol Biol., 289:293-301 (1999).
Janeway, et al., Immunobiology, 3rd Edition, Garland Press, 3:1-3:11 (1997).
Jefferis, R and Lund, J., "Interaction Sites on Human IgG-Fc for FcgammaR: Current Models," Immunology Letters, 82(1-2):57-65(2002).
Kabat, E. A., et al., "Sequences of Proteins of Immunological Interest," NIH, Pub. No. 91-3242, $5^{th}$ ed., vol. 1, pp. 679-687 (1991).
Kamata, N., et al., "Comparison of pH and Ionic Strength Dependence of Interactions between Monoclonal Antibodies and Bovine β-Lactoglobulin," Biosci Biotech Biochem., 60(1):25-29 (1996).
Kim, S. J., et al., "Antibody Engineering for the Development of Therapeutic Antibodies," Mol Cells 20(1):17-29 (2005).
King, D.J., "Applications And Engineering Of Monoclonal Antibodies," CRC Press, pp. 2, 13-4, (1998).
Kohrt, H. E., "Stimulation of natural killer cells with a CD137-specific antibody enhances trastuzumab efficacy in xenotransplant models of breast cancer," J Clin Invest., 122(3):1066-1075 (2012).
Lacroix, M., et al., "Assembly and Enzymatic Properties of the Catalytic Domain of Human Complement Protease C1r," The Journal of Biological Chemistry, 276(39):36233-36240, (2001).
Lazar, G. A., et al., "Engineered antibody Fc variants with enhanced effector function," PNAS, 103(11):4005-4010 (2006).
Li, D. H., et al., "CD72 Down-Modulates BCR-Induced Signal Transduction and Diminishes Survival in Primary Mature B Lymphocytes," J Immunol., 176:5321-5328 (2006).
Li, F. and Ravetch, J. V., "Inhibitory Fcγ receptor engagement drives adjuvant and anti-tumor activities of agonistic CD40 antibodies," Science, 333(6045):1030-1034 (2011).
Li, F. and Ravetch, J. V., "Apoptotic and antitumor activity of death receptor antibodies require inhibitory Fcγ receptor engagement," PNAS, 109(27):10966-10971 (2012).
Liberti, P. A., et al., "Antigenicity of Polypeptides (Poly-alpha-amino Acids). Physicochemical Studies of a Calcium-dependent Antigen-antibody Reaction," Biochemistry 10(9):1632-1639 (1971).
Lund, L., et al., "Multiple Binding Sites on the $C_H2$ Domain of IgG for Mouse FcγRII," Mol Immunol., 29(1):53-59 (1992).
Maccallum, R. M., et al., "Antibody-antigen Interactions: Contact Analysis and Binding Site Topography," J Mol Biol 262:732-745 (1996).

Mackay, M., et al., "Selective dysregulation of the FcγRIIB receptor on memory B cells in SLE," J Exp Med., 203(9):2157-2164 (2006).
Malbec, O. and Daëron, M., "Antibodies against growth factor receptors can inhibit the proliferation of transformed cells via a cis-interaction with inhibitory FcR," Immunol Lett., 143:28-33 (2012).
Manger, K., et al., "Fcγ Receptor IIa Polymorphism in Caucasian Patients with Systemic Lupus Erythematosus," Arth Rheum., 41(7):1181-1189 (1998).
Matsumiya, S., et al., "Structural Comparison of Fucosylated and Nonfucosylated Fc Fragments of Human Immunoglobulin G1," J Mol Biol., 368:767-779 (2007).
Maurer, P. H., et al., "Antigenicity of Polypeptides (PolyαAmino Acids): Calcium-dependent and Independent Antibodies," J Immunol., 105(3):567-573 (1970).
Maxfield, F. R. and Mcgraw, T. E., "Endocytic Recycling," Nat Rev Mol Cell Biol 5(2):121-132 (2004).
Maxwell, K. F., et al., "Crystal structure of the human leukocyte Fc receptor, FcγRIIa," Nat Struct Biol., 6(5):437-442 (1999).
Meyer, T., et al., "Bevacizumab immune complexes activate platelets and induce thrombosis in FCGR2A in transgenic mice," J Thromb Haemost., 7:171-181 (2009).
Mi, W., et al., "Targeting the neonatal Fc receptor for antigen delivery using engineered Fc fragments," J Immunol., 181(11):7550-7561 (2008).
Mimoto, F., et al., "Engineered antibody Fc variant with selectively enhanced FcγRIIb binding over both FcγRIIa$^{R131}$ and FcγRIIa$^{H131}$," Protein Eng Des Sel., 26(10):589-598 (2013).
Moore, G. L., et al., "Engineered Fc variant antibodies with enhanced ability to recruit complement and mediate effector functions," mAbs, 2(2):181-189 (2010).
Morgan, A., et al., "The N-terminal end of the $C_H2$ domain of chimeric human IgG1 anti-HLA-DR is necessary for C1q, FcγRI and FcγRIII binding," Immunol., 86:319-324 (1995).
Murtaugh, M. L., et al., "A Combinatorial Histidine Scanning Library Approach to Engineer Highly pH-Dependent Protein Switches," Protein Sci., 20:1619-1631 (2011).
Muta, T., et al., "A 13-amino-acid motif in the cytoplasmic domain of FcγRIIB modulates B-cell receptor signalling," Nature, 368:70-73 (1994).
Nagaoka, M., et al., "Single Amino Acid Substitution in the Mouse IgG1 Fc Region Induces Drastic Enhancement of the Affinity to Protein A," Protein Engineering, 16(4):243-245 (2003).
Nakagawa, K., et al., "Complement C1s activation in degenerating articular cartilage of rheumatoid arthritis patients: immunohistochemical studies with an active form specific antibody," Ann Rheum Dis., 58:175-181 (1999).
Nakamura, A., et al., "Fcγ Receptor IIB-deficient Mice Develop Goodpasture's Syndrome upon Immunization with Type IV Collagen: A Novel Murine for Autoimmune Glomerular Basement Membrane Disease," J Exp Med., 191(5):899-905 (2000).
Nicholas, R., et al., "Regulation of the immune response. I. Reduction in ability of specific antibody to inhibit long-lasting IgG immunological priming after removal of the Fc fragment," Journal of Experimental Medicine, 129(6):1183-1201 (1969).
Nimmerjahn, F. and Ravetch, J. V., "Fcγ receptors as regulators of immune responses," Nat Rev Immunol., 8:34-47 (2008).
Nimmerjahn, F. and Ravetch, J. V., "Divergent Immunoglobulin G Subclass Activity Through Selective Fc Receptor Binding," Science, 310:1510-1512 (2005).
Ohno, S., et al., "Antigen-binding specificities of antibodies are primarily determined by seven residues of $V_H$," Proc Natl Acad Sci., 82:2945-2949 (1985).
Olferiev, M., et al., "The Role of Activating Protein 1 in the Transcriptional Regulation of the Human FCGR2B Promoter Mediated by the—343 G → C Polymorphism Associated with Systemic Lupus Erythematosus," J Biol Chem., 282(3):1738-1746 (2007).
Pavlou, A. K. and Belsey, M. J., "The therapeutic antibodies market to 2008," Eur J Pharmaceut Biopharmaceut 59:389-396 (2005).
Radaev, S. and Sun, P. D., "Recognition of IgG by Fcγ Receptor," J Biol Chem., 276(19):16478-16483 (2001).
Radaev, S., et al., "The Structure of a Human Type III Fcγ Receptor in Complex with Fc," J Biol Chem., 276(19):16469-16477 (2001).

(56) References Cited

OTHER PUBLICATIONS

Rajpal, A., et al., "A general method for greatly improving the affinity of antibodies by using combinatorial libraries," PNAS 102(24):8466-8471 (2005).
Rathanaswami, P., et al., "Demonstration of an in vivo generated sub-picomolar affinity fully human monoclonal antibody to interleukin-8," Biochem Biophys Res Communic 334:1004-1013 (2005).
Ravetch, J. V. and Lanier, L. L., "Immune Inhibitory Receptors," Science, 290:84-89 (2000).
Reichert, J. M., et al., "Monoclonal antibody successes in the clinic," Nat Biotechnol., 23(9):1073-1078 (2005).
Reverberi, R. and Reverberi, L., "Factors affecting the antigen-antibody reaction," Blood Transfus 5:227-240 (2007).
Richards, J. O., et al., "Optimization of antibody binding to FcγRIIa enhances macrophage phagocytosis of tumor cells," Mol Cancer Ther., 7(8):2517-2527 (2008).
Robles-Carrillo, L., et al., "Anti-CD40L Immune Complexes Potently Activate Platelets In Vitro and Cause Thrombosis in FCGR2A Transgenic Mice," J Immunol., 185:1577-1583 (2010).
Roitt, A., et al., Extract from Chapter 6, Immunology (2000), Moscow, "Mir", pp. 110-111 and English translation of section bridging pp. 110-111.
Roitt, I., et al., Immunology, Moscow, Mir, 110 (2000).
Roitt, I., et al., Immunology, Moscow, Mir, 9 (2000).
Rossi, V., et al., "Baculovirus-Mediated Expression of Truncated Modular Fragments From the Catalytic Region of Human Complement Serine Protease C1s. Evidence for the Involvement of Both Complement Control Protein Modules in the Recognition of the C4 Protein Substrate," The Journal of Biological Chemistry 273(2):1232-1239 (1998).
Safdari, Y., et al., "Antibody Humanization Methods—A Review and Update," Biotechnology & Genetic Engineering Reviews, 29(2):175-186 (2013).
Salmon, J. E., et al., "FcγRIIA Alleles Are Heritable Risk Factors for Lupus Nephritis in African Americans," J Clin Invest., 97:1348-1354 (1996).
Sazinsky, S. L., et al., "Aglycosylated immunoglobulin $G_1$ variants productively engage activating Fc receptors," PNAS, 105(51):20167-20172 (2008).
Scappaticci, F. A., et al., "Arterial Thromboembolic Events in Patients with Metastatic Carcinoma Treated with Chemotherapy and Bevacizumab," J Natl Cancer Inst., 99:1232-1239 (2007).
Schlothauer, T., et al., "Novel human IgG1 and IgG4 Fc-engineered antibodies with completely abolished immune effector functions," Protein Eng Des Sel., 29(10):457-466 (2016).
Schroter, C., et al., "A generic approach to engineer antibody pH-switches using combinatorial histidine scanning libraries and yeast display," mAbs 7:1, 138-151 (2015).
Shields, R. L., et al., "High Resolution Mapping of the Binding Site of Human IgG1 for $Fc_\gamma RI$, $Fc_\gamma RII$, $Fc_\gamma RIII$, and FcRn and Design of IgG1 Variants with Improved Binding to the $Fc_\gamma R$," J Biol Chem 276(9):6591-6604 (2001).
Shinkawa, T., et al., "The Absence of Fucose but Not the Presence of Galactose or Bisecting N-Acteylglucosamine of Human IgG1 Complex-type Oligosaccharides Shows the Critical Role of Enhancing Antibody-dependent Cellular Cytotoxicity," J Biol Chem., 278(5):3466-3473 (2003).
Siberil, S., et al., "Molecular aspects of human FcγR interactions with IgG: Functional and therapeutic consequences," Immunol Lett., 106:111-118 (2006).
Singer, et al., Genes & Genomes, 1:63-64 (1998).
Smith, K. G. C. and Clatworthy, M. R., "FcγRIIB in autoimmunity and infection: evolutionary and therapeutic implications," Nat Rev Immunol., 10(5):328-343 (2010).
Sondermann, P., et al., "Crystal structure of the soluble form of the human Fcγ-receptor IIb: a new member of the immunoglobulin superfamily at 1.7 Å resolution," The EMBO Journal, 18(5):1095-1103 (1999).
Sondermann, P., et al., "Molecular Basis for Immune Complex Recognition: A Comparison of Fc-Receptor Structures," J Mol Biol., 309:737-749 (2001).
Sondermann, P., et al., "The 3.2-A crystal structure of the human IgG1 Fc fragment-FcγRIII complex," Nature, 406:267-273 (2000).
Stepanov, V. M., "Molecular Biology. Structure and Functions of Proteins," $3^{rd}$ Edition, Moscow University Publishing House: Science, pp. 61-62 (2005).
Su, K., et al., "Expression Profiled of FcγRIIb on Leukocytes and Its Dysregulation in Systemic Lupus Erythematosus," J Immunol., 178(5):3272-3280 (2007).
Suzuki, T., et al., "Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neonatal FcR," J Immunol., 184:1968-1976 (2010).
Travis, J., et al., "Isolation of Albumin from Whole Human Plasma and Fractionation of Albumin-Depleted Plasma," Biochem J., 157:301-306 (1976).
Tseng, Y., et al., "Probing the Structure of C1 with An Anti-C1s Monoclonal Antibody: The Possible Existence of Two Forms of C1 in Solution," Molecular Immunology 34(8-9):671-679 (1997).
Vajdos, F. F., et al., "Comprehensive Functional Maps of the Antigen-binding Site of an Anti-ErbB2 Antibody Obtained with Shotgun Scanning Mutagenesis," J Mol Biol 320:415-428 (2002).
Veri, M.-C., et al., "Monoclonal antibodies capable of discriminating the human inhibitory Fcγ-receptor IIb (CD32B) from the activating Fcγ-receptor IIa (CD32A): biochemical, biological and functional characterization," Immunology, 121:392-404 (2007).
Veri, M.-C., et al., "Therapeutic Control of B Cell Activation via Recruitment of Fcγ Receptor IIb (CD32B) Inhibitory Function With a Novel Bispecific Antibody Scaffold," Arth Rheum., 62(7):1933-1943 (2010).
Wang, W., et al., "Monoclonal Antibodies with Identical Fc Sequences Can Bind to FcRn Differentially with Pharmacokinetic Consequences," Drug Metab Dispos., 39(9):1469-1477 (2011).
Warmerdam, P. A., et al., "The Human Low Affinity Immunoglobulin G Fc Receptor IIC Gene is a Result of an Unequal Crossover Event," The Journal of Biological Chemistry 268(10):7346-7349 (1993).
Warmerdam, P. A. M., et al.,"Molecular Basis for a Polymorphism of Human Fcγ II (CD32)," J Exp Med., 172:19-25 (1990).
Weiss, G. A., et al., "Rapid mapping of protein functional epitopes by combinatorial alanine scanning," PNAS, 97(16):8950-8954 (2000).
Wenink, M. H., et al., "The Inhibitory FcγIIb Receptor Dampens TLR4-Mediated Immune Responses and Is Selectively Up-regulated on Dendritic Cells from Rheumatoid Arthritis Patients with Quiescent Disease," J Immunol., 183:4509-4520 (2009).
Wernersson, S., et al., "IgG-Mediated Enhancement of Antibody Responses is Low in Fc Receptor γ Chain-Deficient Mice and Increased in FcγRII-Deficient Mice," J Immunol, 163:618-622 (1999).
Wilson, N. S., et al., "An Fcγ Receptor-Dependent Mechanism Drives Antibody-Mediated Target-Receptor Signaling in Cancer Cells," Cancer Cell, 19:101-113 (2011).
Wines, B.D., et al., "The IgG Fc Contains Distinct Fc Receptor (FcR) Binding Sites: the Leukocyte Receptors Fc Gamma Ri and Fc Gamma Riia Bind to a Region in the Fc Distinct From That Recognized by Neonatal FcR and Protein A," Journal of immunology 164(10):5313-5318 (2000).
Wu, H., et al., "Development of Motavizumab, an Ultra-potent Antibody for the Prevention of Respiratory Syncytial Virus Infection in the Upper and Lower Respiratory Tract," Journal of Molecular Biology, 368:652-665 (2007).
Xu, Y., et al., "FcγRs Modulate Cytotoxicity of Anti-Fas Antibodies: Implications for Agonistic Antibody-Based Therapeutics," J Immunol., 171:562-568 (2003).
Yarilin, A. A., "Principles of immunology: Textbook—M.: Medicina," Fundamentals of Immunology 608:169-172, 354-358 (1999).
Yarilin, "Osnovy immunologii," M. Meditsina, 181-184 (1999).
Yeung, Y. A., et al., "Engineering Human IgG1 Affinity to Human Neonatal Fc Receptor: Impact of Affinity Improvement on Pharmacokinetics in Primates," J Immunol 182:7663-7671 (2009).

(56) References Cited

OTHER PUBLICATIONS

Yuasa, T., et al., "Deletion of Fcγ Receptor IIB Renders H-2$^b$ Mice Susceptible to Collagen-induced Arthritis," J Exp Med., 189(1):187-194 (1999).
Zalevsky, J., et al., "Enhanced antibody half-life improves in vivo activity," Nat Biotechnol., 28(2):157-159 (2010).
Zalevsky, J., et al., "The impact of Fc engineering on an anti-CD19 antibody: increased Fcγ receptor affinity enhances B-cell clearing in nonhuman primates," Blood, 113(16):3735-3743 (2009).
Zhang, Y., et al., "Immune Complex/Ig Negatively Regulate TLR4-Triggered Inflammatory Response in Macrophages through FcγRIIb-Dependent PGE$_2$ Production," J Immunol., 182:554-562 (2009).
Zhang, M., et al., "Effective therapy for a murine model of human anaplastic large-cell lymphoma with the anti-CD30 monoclonal antibody, HeFi-1, does not require activating Fc receptors," Blood, 108(2):705-710 (2006).
U.S. Appl. No. 14/782,392, filed Oct. 5, 2015, Rosenthal et al.
U.S. Appl. No. 14/939,706, filed Nov. 12, 2015, Rosenthal et al.
U.S. Appl. No. 09/483,588, filed Jan. 14, 2000, Presta.
U.S. Appl. No. 10/029,988, filed Dec. 31, 2001, Levanon et al.
U.S. Appl. No. 10/032,037, filed Dec. 31, 2001, Levanon et al.
U.S. Appl. No. 10/032,423, filed Dec. 31, 2001, Lazarovits et al.
U.S. Appl. No. 10/379,392, filed Mar. 3, 2003, Lazar et al.
U.S. Appl. No. 10/672,280, filed Sep. 26, 2003, Lazar et al.
U.S. Appl. No. 10/822,231, filed Mar. 26, 2004, Lazar et al.
U.S. Appl. No. 10/902,588, filed Jul. 28, 2004, Stavenhagen et al.
U.S. Application No. 11/108, 135, filed Apr. 15, 2005, Koenig et al.
U.S. Appl. No. 11/124,620, filed May 5, 2005, Lazar et al.
U.S. Appl. No. 11/483,250, filed Jul. 7, 2006, Lazar et al.
U.S. Appl. No. 11/520,121, filed Sep. 13, 2006, Presta.
U.S. Appl. No. 11/754,015, filed May 25, 2007, Johnson et al.
U.S. Appl. No. 11/764,001, filed Jun. 15, 2007, Lazar et al.
U.S. Appl. No. 11/765,353, filed Jun. 19, 2007, Lazar et al.
U.S. Appl. No. 11/929,742, filed Oct. 30, 2007, Lazar et al.
U.S. Appl. No. 11/932,151, filed Oct. 31, 2007, Chamberlai, et al.
U.S. Appl. No. 11/952,568, filed Dec. 7, 2007, Stavenhagen et al.
U.S. Appl. No. 11/981,647, filed Oct. 31, 2007, Desjarlais et al.
U.S. Appl. No. 12/018,754, filed Jan. 23, 2008, Bernett et al.
U.S. Appl. No. 12/020,443, filed Jan. 25, 2008, Lazar et al.
U.S. Appl. No. 12/147,379, filed Jun. 26, 2008, Datt et al.
U.S. Appl. No. 12/156,183, filed May 30, 2008, Chu et al.
U.S. Appl. No. 12/186,058, filed Aug. 5, 2008, Koenig et al.
U.S. Appl. No. 12/532,022, filed Mar. 19, 2008, Guler-Gane et al.
U.S. Appl. No. 12/577,967, filed Oct. 13, 2009, Lowman et al.
U.S. Appl. No. 12/733,865, filed Aug. 24, 2008, Chung et al.
U.S. Appl. No. 12/864,075, filed Oct. 6, 2010, Bernett et al.
U.S. Appl. No. 12/896,610, filed Oct. 1, 2010, Lazar et al.
U.S. Appl. No. 13/045,345, filed Mar. 10, 2011, Pons et al.
U.S. Appl. No. 13/077,644, filed Mar. 31, 2011, Beliard et al.
U.S. Appl. No. 13/174,423, filed Jun. 30, 2011, Jackson et al.
U.S. Appl. No. 13/422,887, filed Mar. 16, 2012, Jackson et al.
U.S. Appl. No. 13/637,415, filed Mar. 30, 2011, Igawa et al.
U.S. Appl. No. 13/764,693, filed Feb. 11, 2013, Lazar et al.
U.S. Appl. No. 13/832,247, filed Mar. 15, 2013, McWhirter et al.
U.S. Appl. No. 13/855,448, filed Apr. 2, 2013, Murphy et al.
U.S. Appl. No. 13/964,159, filed Aug. 12, 2013, Yancopoulos et al.
U.S. Appl. No. 13/990,158, filed Nov. 30, 2011, Igawa et al.
U.S. Appl. No. 14/001,218, filed Dec. 2, 2013, Mimoto et al., related application.
U.S. Appl. No. 14/007,947, filed Dec. 30, 2013, Igawa et al.
U.S. Appl. No. 14/078,501, filed Nov. 12, 2013, Lazar et al.
U.S. Appl. No. 14/085,424, filed Nov. 20, 2013, McWhirter et al.
U.S. Appl. No. 14/127,576, filed Jun. 29, 2012, Mimoto et al.
U.S. Appl. No. 14/290,544, filed May 29, 2014, Swergold et al.
U.S. Appl. No. 14/347,321, filed Sep. 28, 2012, Igawa et al., related application.
U.S. Appl. No. 14/349,884, filed Oct. 5, 2012, Igawa et al.
U.S. Appl. No. 14/377,556, filed Feb. 8, 2013, Kuramochi et al.
U.S. Appl. No. 14/379,825, filed Feb. 22, 2013, Igawa et al., related application.
U.S. Appl. No. 14/402,574, filed May 30, 2013, Igawa et al.
U.S. Appl. No. 14/404,051, filed Nov. 26, 2014, Igawa et al.
U.S. Appl. No. 14/406,232, filed Jun. 14, 2013, Igawa et al.
U.S. Appl. No. 14/422,207, filed Aug. 23, 2013, Igawa et al., related application.
U.S. Appl. No. 14/423,269, filed Aug. 23, 2013, Katada et al., related application.
U.S. Appl. No. 14/641,026, filed Mar. 6, 2015, Andrien et al.
U.S. Appl. No. 14/654,895, filed Dec. 26, 2013, Igawa et al.
U.S. Appl. No. 14/717,914, filed May 20, 2015, Stevis et al.
U.S. Appl. No. 14/727,313, filed Jun. 1, 2015, Andrien et al.
U.S. Appl. No. 14/781,069, filed Apr. 2, 2014, Mimoto et al., related application.
U.S. Appl. No. 14/890,811, filed Nov. 12, 2015, Rosenthal et al.
U.S. Appl. No. 14/974,488, filed Dec. 18, 2015, Ruike et al.
U.S. Appl. No. 15/963,455, filed Apr. 26, 2018, Ruike et al.
U.S. Appl. No. 15/977,757, filed May 11, 2018, Igawa et al., related application.
U.S. Appl. No. 17/561,207, filed Dec. 23, 2021, Igawa et al., related application.
U.S. Appl. No. 17/610,204, filed Nov. 10, 2021, Koga, related application.
U.S. Appl. No. 17/671,185, filed Feb. 14, 2022, Mimoto et al., related application.
U.S. Appl. No. 17/768,053, filed Apr. 11, 2022, Koga et al., related application.
U.S. Appl. No. 17/846,672, filed Jun. 22, 2022, Mimoto et al., related application.
U.S. Appl. No. 17/854,023, filed Jun. 30, 2022, Igawa et al., related application.
Office Action dated Mar. 23, 2023 in U.S. Appl. No. 17/046,395, filed Oct. 9, 2020, Fukukawa et al.
Restriction Requirement dated Jul. 28, 2022 in U.S. Appl. No. 17/046,395, filed Oct. 9, 2020, Fukukawa et al.
Hironiwa, H., et al., "Calcium-dependent antigen binding as a novel modality for antibody recycling by endosomal antigen dissociation," mAbs, 8(1):65-73 (2016).
Goel, M., et al., "Plasticity within the Antigen-Combining Site May Manifest as Molecular Mimicry in the Humoral Immune Response," J Immunol., 173:7358-7367 (2004).
Igawa, T., et al., "pH-dependent antigen-binding antibodies as a novel therapeutic modality," Biochim Biophys Acta., 1844(11): 1943-1950 (2014).
Kanyavuz, A., et al., "Breaking the law: unconventional strategies for antibody diversification," Nat Rev Immunol., 19:355-368 (2019).
Lescar, J., et al., "Crystal Structure of a Cross-reaction Complex between Fab F9.13.7 and Guinea Fowl Lysozyme," J Biol Chem., 270(30):18067-18076 (1995).
Patton, A., et al., "An acid dissociation bridging ELISA for detection of antibodies directed against therapeutic proteins in the presence of antigen," J Immunol Meth., 304:189-195 (2005).
U.S. Appl. No. 18/286,471, filed Oct. 11, 2023, Koga.
U.S. Appl. No. 18/472,932, filed Sep. 22, 2023, Fukuzawa et al.
Eskandary, F., et al., "Anti-C1s monoclonal antibody BIVV009 in late antibody-mediated kidney allograft rejection-results from a first-in-patient phase 1 trial," Am J Transplant., 18:916-926 (2018).
Uchio-Yamada, K., et al., "C1r/C1s deficiency is insufficient to induce murine systemic lupus erythematosus," Genes Immun., 20:121-130 (2019).
Wu, et al., "Research Progress on Complement C1 Inhibitors," International Journal of Blood Transfusion and Hematology, 22(4):260-263 (1999), with English abstract.
Eskandary, F., et al., "Complement inhibition as a potential new therapy for antibody-mediated rejection," Transpl Int., 29(4):392-402 (2016).
Li, X. and Wen, J., "Antibody-mediated rejection in kidney transplantation: diagnosis and management," Chinese Journal of Nephrology, Dialysis and Transplantation, 24(5):481-486 (2015), with English abstract.
Roth, A., et al., "Sutimlimab in Cold Agglutinin Disease," N Engl J Med., 384(14):1323-1334 (2021).
U.S. Appl. No. 18/286,471, filed Oct. 11, 2023, Koga, related application.

(56) References Cited

OTHER PUBLICATIONS

U.S. Appl. No. 18/472,932, filed Sep. 22, 2023, Fukuzawa et al., related application.

* cited by examiner

[Fig. 1]
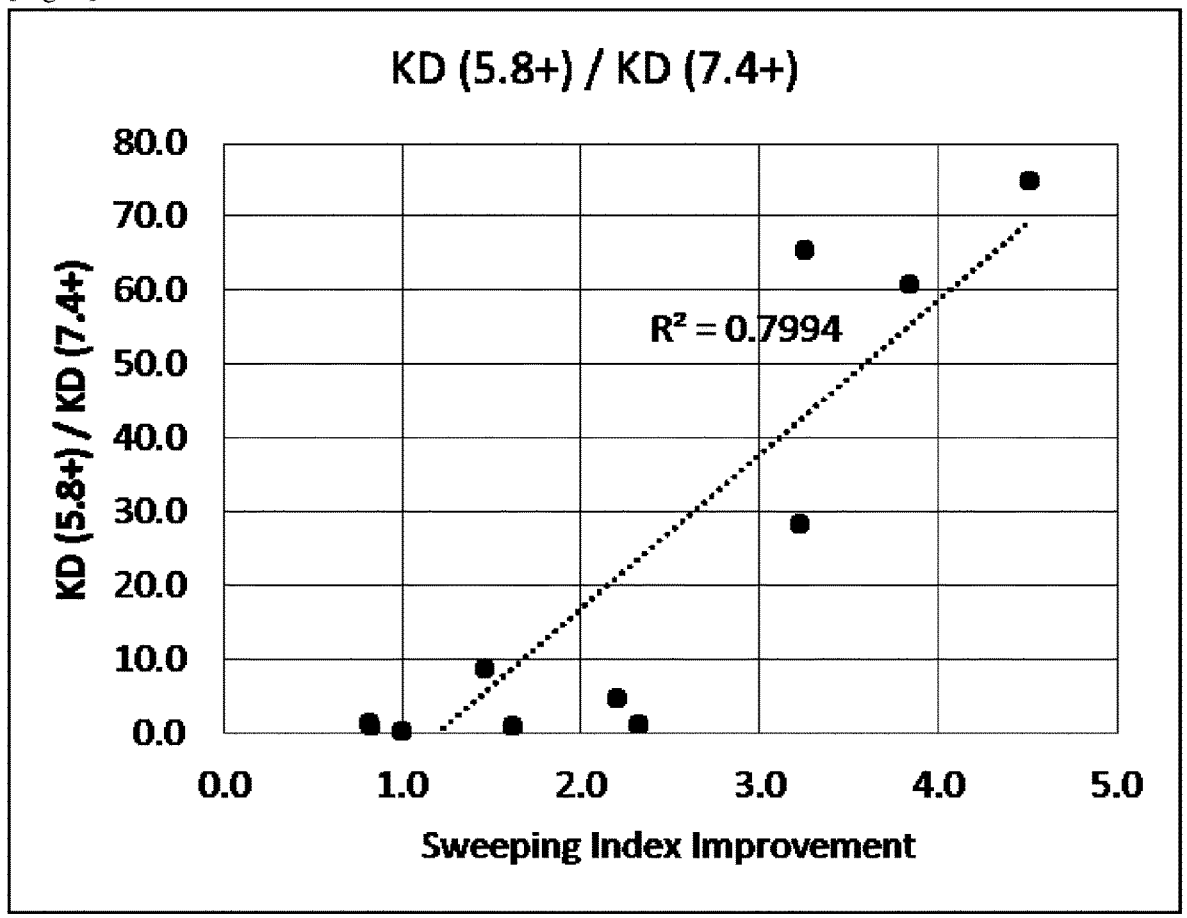

[Fig. 2]
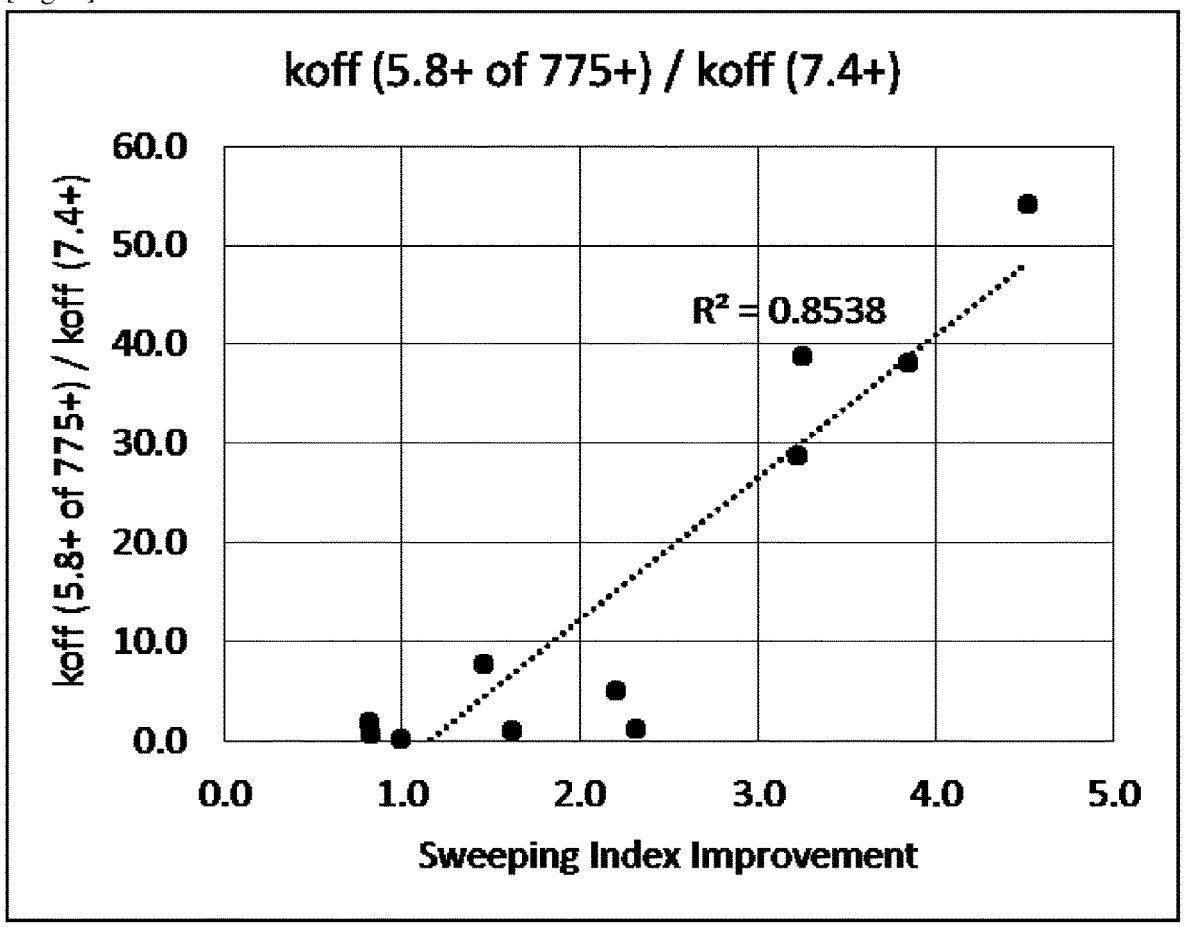

```
                          SEQUENCE LISTING

<160> NUMBER OF SEQ ID NOS: 88

<210> SEQ ID NO 1
<211> LENGTH: 673
<212> TYPE: PRT
<213> ORGANISM: Homo sapiens

<400> SEQUENCE: 1

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
                20                  25                  30

Tyr Gly Ile His Leu Tyr Phe Thr His Leu Asp Ile Glu Leu Ser Glu
            35                  40                  45

Asn Cys Ala Tyr Asp Ser Val Gln Ile Ile Ser Gly Asp Thr Glu Glu
        50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
                100                 105                 110

Val Ala Thr Asp Ile Asn Glu Cys Thr Asp Phe Val Asp Val Pro Cys
            115                 120                 125

Ser His Phe Cys Asn Asn Phe Ile Gly Gly Tyr Phe Cys Ser Cys Pro
        130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
                180                 185                 190

Leu Glu Lys Gly Phe Gln Val Val Val Thr Leu Arg Arg Glu Asp Phe
            195                 200                 205

Asp Val Glu Ala Ala Asp Ser Ala Gly Asn Cys Leu Asp Ser Leu Val
        210                 215                 220
```

```
Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
        275                 280                 285

Trp Glu Pro Ala Lys Ala Lys Tyr Val Phe Arg Asp Val Val Gln Ile
        290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
        355                 360                 365

Tyr Thr Cys Glu Glu Pro Tyr Tyr Tyr Met Glu Asn Gly Gly Gly Gly
        370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
            420                 425                 430

Asn Phe Pro Trp Gln Val Phe Phe Asp Asn Pro Trp Ala Gly Gly Ala
        435                 440                 445

Leu Ile Asn Glu Tyr Trp Val Leu Thr Ala Ala His Val Val Glu Gly
        450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
        515                 520                 525

Thr Val Ser Pro Ile Cys Leu Pro Gly Thr Ser Ser Asp Tyr Asn Leu
        530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
        610                 615                 620

Asp Pro Asn Asp Lys Thr Lys Phe Tyr Ala Ala Gly Leu Val Ser Trp
625                 630                 635                 640
```

Gly Pro Gln Cys Gly Thr Tyr Gly Leu Tyr Thr Arg Val Lys Asn Tyr
                    645                 650                 655

Val Asp Trp Ile Met Lys Thr Met Gln Glu Asn Ser Thr Pro Arg Glu
            660                 665                 670

Asp

<210> SEQ ID NO 2
<211> LENGTH: 673
<212> TYPE: PRT
<213> ORGANISM: Ruttus norvegicus

<400> SEQUENCE: 2

Glu Pro Thr Met Tyr Gly Glu Ile Leu Ser Pro Asn Tyr Pro Gln Ala
1               5                   10                  15

Tyr Pro Asn Glu Val Val Lys Thr Trp Asp Ile Glu Val Pro Glu Gly
            20                  25                  30

Phe Gly Ile His Leu Tyr Phe Thr His Leu Asp Met Glu Leu Ser Glu
        35                  40                  45

Asn Cys Ala Tyr Asp Ser Val Gln Ile Ile Ser Gly Ile Glu Glu
    50                  55                  60

Glu Arg Leu Cys Gly Gln Arg Thr Ser Lys Ser Pro Asn Ser Pro Thr
65                  70                  75                  80

Val Glu Glu Phe Gln Phe Pro Tyr Asn Arg Leu Gln Val Val Phe Thr
                85                  90                  95

Ser Asp Phe Ser Asn Glu Glu Arg Phe Thr Gly Phe Ala Ala Tyr Tyr
            100                 105                 110

Ser Ala Val Asp Val Asn Glu Cys Thr Asp Phe Thr Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Arg Thr Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Asn Pro Tyr Pro Glu Asn Ser Arg Cys Glu Tyr Gln Ile Arg
            180                 185                 190

Leu Gln Glu Gly Phe Arg Leu Val Leu Thr Ile Arg Arg Glu Asp Phe
        195                 200                 205

Asp Val Glu Pro Ala Asp Ser Glu Gly Asn Cys His Asp Ser Leu Thr
    210                 215                 220

Phe Ala Ala Lys Asn Gln Gln Phe Gly Pro Tyr Cys Gly Asn Gly Phe
225                 230                 235                 240

Pro Gly Pro Leu Thr Ile Lys Thr Gln Ser Asn Thr Leu Asp Ile Val
                245                 250                 255

Phe Gln Thr Asp Leu Thr Gly Gln Asn Lys Gly Trp Lys Leu Arg Tyr
            260                 265                 270

His Gly Asp Pro Ile Pro Cys Pro Lys Glu Ile Ser Ala Asn Ser Ile
        275                 280                 285

Trp Glu Pro Glu Lys Ala Lys Tyr Val Phe Lys Asp Val Val Lys Ile
    290                 295                 300

Thr Cys Val Asp Gly Phe Glu Val Val Glu Gly Asn Val Gly Ser Thr
305                 310                 315                 320

Ser Phe Tyr Ser Thr Cys Gln Ser Asn Gly Gln Trp Ser Asn Ser Arg
                325                 330                 335

Leu Glu Cys Gln Pro Val Asp Cys Gly Val Pro Glu Pro Ile Glu Asn
                340                 345                 350

Gly Lys Val Glu Asp Pro Glu Asp Thr Val Phe Gly Ser Val Ile His
            355                 360                 365

Tyr Thr Cys Glu Glu Pro Tyr Tyr Met Glu Gln Glu Gly Gly
    370                 375                 380

Glu Tyr His Cys Ala Ala Asn Gly Ser Trp Val Asn Asp Gln Leu Gly
385                 390                 395                 400

Val Glu Leu Pro Lys Cys Ile Pro Val Cys Gly Val Pro Thr Glu Pro
                405                 410                 415

Phe Lys Val Gln Gln Arg Ile Phe Gly Gly Tyr Ser Thr Lys Ile Gln
            420                 425                 430

Ser Phe Pro Trp Gln Val Tyr Phe Glu Ser Pro Arg Gly Gly Gly Ala
        435                 440                 445

Leu Ile Asp Glu Tyr Trp Val Leu Thr Ala Ala His Val Val Glu Gly
        450                 455                 460

Asn Ser Asp Pro Val Met Tyr Val Gly Ser Thr Leu Leu Lys Ile Glu
465                 470                 475                 480

Arg Leu Arg Asn Ala Gln Arg Leu Ile Thr Glu Arg Val Ile Ile His
                485                 490                 495

Pro Ser Trp Lys Gln Glu Asp Asp Leu Asn Thr Arg Thr Asn Phe Asp
            500                 505                 510

Asn Asp Ile Ala Leu Val Gln Leu Lys Asp Pro Val Lys Met Gly Pro
        515                 520                 525

Thr Val Ala Pro Ile Cys Leu Pro Glu Thr Ser Ser Asp Tyr Asn Pro
    530                 535                 540

Ser Glu Gly Asp Leu Gly Leu Ile Ser Gly Trp Gly Arg Thr Glu Asn
545                 550                 555                 560

Arg Thr Asn Val Ile Gln Leu Arg Gly Ala Lys Leu Pro Ile Thr Ser
                565                 570                 575

Leu Glu Lys Cys Gln Gln Val Lys Val Glu Asn Pro Lys Ala Arg Ser
            580                 585                 590

Asn Asp Tyr Val Phe Thr Asp Asn Met Ile Cys Ala Gly Glu Lys Gly
        595                 600                 605

Val Asp Ser Cys Glu Gly Asp Ser Gly Gly Ala Phe Ala Leu Pro Val
    610                 615                 620

Pro Asn Val Lys Asp Pro Lys Phe Tyr Val Ala Gly Leu Val Ser Trp
625                 630                 635                 640

Gly Lys Lys Cys Gly Thr Tyr Gly Ile Tyr Thr Lys Val Lys Asn Tyr
                645                 650                 655

Val Asp Trp Ile Leu Lys Thr Met Gln Glu Asn Ser Gly Pro Lys Lys
            660                 665                 670

Asp

<210> SEQ ID NO 3
<211> LENGTH: 673
<212> TYPE: PRT
<213> ORGANISM: Macaca fascicularis

<400> SEQUENCE: 3

Glu Pro Thr Met Tyr Gly Glu Ile Leu Ser Pro Asn Tyr Pro Gln Ala
1                 5                   10                  15

Tyr Pro Ser Glu Val Glu Lys Ser Trp Asp Ile Glu Val Pro Glu Gly
                20                  25                  30

-continued

```
Tyr Gly Ile His Leu Tyr Phe Thr His Leu Asp Ile Glu Leu Ser Glu
         35                  40                  45
Asn Cys Ala Tyr Asp Ser Val Gln Ile Met Ser Gly Asp Ile Glu Glu
 50                  55                  60
Gly Arg Leu Cys Gly Gln Arg Thr Ser Asn Asn Pro Tyr Ser Pro Ile
 65                  70                  75                  80
Val Glu Glu Phe Gln Val Pro Tyr Asn Lys Leu Gln Val Ile Phe Lys
                 85                  90                  95
Ser Asp Phe Ser Asn Glu Glu Arg Phe Thr Gly Phe Ala Ala Tyr Tyr
                100                 105                 110
Val Ala Thr Asp Ile Asn Glu Cys Thr Asp Phe Val Asp Ala Pro Cys
                115                 120                 125
Ser His Phe Cys Asn Asn Phe Ile Gly Gly Tyr Phe Cys Ser Cys Pro
            130                 135                 140
Pro Glu Tyr Phe Leu His Asp Asp Met Lys Asn Cys Gly Val Asn Cys
145                 150                 155                 160
Ser Gly Asp Val Phe Thr Ala Leu Ile Gly Glu Ile Ala Ser Pro Asn
                    165                 170                 175
Tyr Pro Lys Pro Tyr Pro Glu Asn Ser Arg Cys Glu Tyr Gln Ile Arg
                180                 185                 190
Leu Glu Lys Gly Phe Gln Val Val Thr Val Arg Arg Glu Asp Phe
                195                 200                 205
Asp Val Glu Pro Ala Asp Ser Glu Gly Asn Cys Leu Asp Ser Leu Val
                210                 215                 220
Phe Val Ala Gly Asp Gln Gln Phe Gly Pro Tyr Cys Gly Arg Gly Phe
225                 230                 235                 240
Pro Gly Pro Leu Asn Ile Glu Thr Lys Ser Asn Val Leu Asp Ile Ile
                245                 250                 255
Phe Gln Thr Asp Leu Thr Gly Gln Asn Lys Gly Trp Lys Leu Arg Tyr
                260                 265                 270
His Gly Asp Pro Met Pro Cys Pro Lys Glu Glu Thr Pro Thr Ser Val
            275                 280                 285
Trp Glu Pro Ala Lys Ala Lys Tyr Val Phe Arg Asp Val Val Arg Ile
290                 295                 300
Thr Cys Leu Asp Gly Phe Glu Val Val Glu Gly Arg Val Gly Ala Thr
305                 310                 315                 320
Ser Phe His Ser Thr Cys Gln Ser Asn Gly Lys Trp Ser Asn Ser Lys
                    325                 330                 335
Leu Lys Cys Gln Pro Val Asp Cys Gly Ile Pro Glu Ser Ile Glu Asn
                340                 345                 350
Gly Lys Val Glu Asp Pro Glu Ser Thr Leu Phe Gly Ser Val Thr Arg
            355                 360                 365
Tyr Thr Cys Glu Glu Pro Tyr Tyr Met Glu Asn Gly Gly Asn Gly
370                 375                 380
Gln Tyr His Cys Ala Ser Asn Gly Ser Trp Val Asn Glu Ala Leu Ser
385                 390                 395                 400
Pro Glu Leu Pro Lys Cys Val Pro Val Cys Gly Val Pro Arg Glu Pro
                405                 410                 415
Phe Glu Gly Lys Gln Arg Ile Ile Gly Gly Ser Asp Ala Asp Ile Lys
                420                 425                 430
Asn Phe Pro Trp Gln Val Phe Phe Asp Asn Pro Trp Ala Gly Gly Ala
                435                 440                 445
Leu Ile Asp Glu Tyr Trp Val Leu Thr Ala Ala His Val Val Glu Gly
```

```
                450             455             460
Asn Gln Glu Pro Thr Met Tyr Val Gly Ser Thr Ser Val Gln Thr Ser
465                 470                 475                 480

Arg Leu Ala Lys Ser Lys Met Leu Thr Ser Glu Arg Val Phe Ile His
                485                 490                 495

Pro Gly Trp Lys Leu Leu Glu Val Pro Glu Ala Arg Thr Asn Phe Asp
            500                 505                 510

Asn Asp Ile Ala Leu Val Gln Leu Lys Asp Pro Val Lys Met Gly Pro
            515                 520                 525

Thr Val Ala Pro Ile Cys Leu Pro Gly Thr Ser Ser Asp Tyr Asn Leu
            530                 535                 540

Met Asp Gly Asp Leu Gly Leu Ile Ala Gly Trp Gly Arg Thr Glu Lys
545                 550                 555                 560

Arg Asp Arg Ala Leu Arg Leu Lys Ala Ala Arg Leu Pro Val Ala Pro
                565                 570                 575

Leu Arg Lys Cys Arg Glu Val Lys Val Glu Asn Pro Lys Ala Asp Ala
            580                 585                 590

Gly Ala Tyr Val Phe Thr Pro Asn Met Ile Cys Ala Gly Gly Glu Lys
            595                 600                 605

Gly Met Asp Ser Cys Lys Gly Asp Ser Gly Gly Ala Phe Ala Val Gln
610                 615                 620

Asp Pro Asn Asp Lys Thr Lys Phe Tyr Val Ala Gly Leu Val Ser Trp
625                 630                 635                 640

Gly Pro Gln Cys Gly Thr Tyr Gly Leu Tyr Thr Arg Val Gln Asn Tyr
                645                 650                 655

Val Asp Trp Ile Lys Lys Thr Met Gln Glu Asn Ser Thr Pro Ser Lys
                660                 665                 670
Asp

<210> SEQ ID NO 4
<211> LENGTH: 30
<212> TYPE: PRT
<213> ORGANISM: Artificial Sequnce
<220> FEATURE:
<223> OTHER INFORMATION: an artificially synthesized sequence

<400> SEQUENCE: 4

Glu Val Met Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 5
<211> LENGTH: 14
<212> TYPE: PRT
<213> ORGANISM: Artificial Sequnce
<220> FEATURE:
<223> OTHER INFORMATION: an artificially synthesized sequence

<400> SEQUENCE: 5

Trp Val Arg Gln Ala Pro Gly Lys Gly Leu Glu Trp Val Ala
1               5                   10

<210> SEQ ID NO 6
<211> LENGTH: 32
<212> TYPE: PRT
<213> ORGANISM: Artificial Sequnce
<220> FEATURE:
<223> OTHER INFORMATION: an artificially synthesized sequence
```

```
<400> SEQUENCE: 6

Arg Phe Thr Ile Ser Arg Asp Asn Ser Lys Asp Thr Leu Tyr Leu Gln
1               5                   10                  15

Met Asn Ser Leu Arg Ala Glu Asp Thr Ala Leu Tyr Tyr Cys Ala Arg
            20                  25                  30

<210> SEQ ID NO 7
<211> LENGTH: 11
<212> TYPE: PRT
<213> ORGANISM: Artificial Sequnce
<220> FEATURE:
<223> OTHER INFORMATION: an artificially synthesized sequence

<400> SEQUENCE: 7

Trp Gly Gln Gly Thr Leu Val Thr Val Ser Ser
1               5                   10

<210> SEQ ID NO 8
<211> LENGTH: 23
<212> TYPE: PRT
<213> ORGANISM: Artificial Sequnce
<220> FEATURE:
<223> OTHER INFORMATION: an artificially synthesized sequence

<400> SEQUENCE: 8

Gln Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 9
<211> LENGTH: 15
<212> TYPE: PRT
<213> ORGANISM: Artificial Sequnce
<220> FEATURE:
<223> OTHER INFORMATION: an artificially synthesized sequence

<400> SEQUENCE: 9

Trp Tyr Gln Gln Lys Pro Gly Lys Ala Pro Lys Leu Trp Ile Tyr
1               5                   10                  15

<210> SEQ ID NO 10
<211> LENGTH: 32
<212> TYPE: PRT
<213> ORGANISM: Artificial Sequnce
<220> FEATURE:
<223> OTHER INFORMATION: an artificially synthesized sequence

<400> SEQUENCE: 10

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 11
<211> LENGTH: 10
<212> TYPE: PRT
<213> ORGANISM: Artificial Sequnce
<220> FEATURE:
<223> OTHER INFORMATION: an artificially synthesized sequence

<400> SEQUENCE: 11

Phe Gly Gln Gly Thr Lys Leu Glu Ile Lys
1               5                   10
```

<210> SEQ ID NO 12
<211> LENGTH: 30
<212> TYPE: PRT
<213> ORGANISM: Artificial Sequnce
<220> FEATURE:
<223> OTHER INFORMATION: an artificially synthesized sequence

<400> SEQUENCE: 12

Glu Val Met Leu Val Glu Ser Gly Gly Gly Leu Val Lys Pro Gly Gly
1               5                   10                  15

Ser Leu Arg Leu Ser Cys Ala Ala Ser Gly Phe Glu Phe Glu
            20                  25                  30

<210> SEQ ID NO 13
<211> LENGTH: 118
<212> TYPE: PRT
<213> ORGANISM: Artificial Sequnce
<220> FEATURE:
<223> OTHER INFORMATION: an artificially synthesized sequence

<400> SEQUENCE: 13

Glu Val Met Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Ser His Thr Tyr Tyr Leu Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Leu Tyr Tyr Cys
                85                  90                  95

Ala Arg Leu Phe Thr Gly Tyr Ala Met Asp Tyr Trp Gly Gln Gly Thr
            100                 105                 110

Leu Val Thr Val Ser Ser
        115

<210> SEQ ID NO 14
<211> LENGTH: 109
<212> TYPE: PRT
<213> ORGANISM: Artificial Sequnce
<220> FEATURE:
<223> OTHER INFORMATION: an artificially synthesized sequence

<400> SEQUENCE: 14

Gln Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr Tyr Arg Leu Pro
                85                  90                  95

Pro Ile Thr Phe Gly Gln Gly Thr Lys Leu Glu Ile Lys
            100                 105

<210> SEQ ID NO 15
<211> LENGTH: 327
<212> TYPE: PRT
<213> ORGANISM: Artificial Sequnce
<220> FEATURE:
<223> OTHER INFORMATION: an artificially synthesized sequence

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 16
<211> LENGTH: 107

```
<212> TYPE: PRT
<213> ORGANISM: Artificial Sequnce
<220> FEATURE:
<223> OTHER INFORMATION: an artificially synthesized sequence

<400> SEQUENCE: 16

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 17
<211> LENGTH: 118
<212> TYPE: PRT
<213> ORGANISM: Artificial Sequnce
<220> FEATURE:
<223> OTHER INFORMATION: an artificially synthesized sequence

<400> SEQUENCE: 17

Glu Val Met Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Ser His Thr Tyr Tyr Leu Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Leu Tyr Tyr Cys
                85                  90                  95

Ala Arg Leu Phe Thr Gly His Ala Met Asp Tyr Trp Gly Gln Gly Thr
            100                 105                 110

Leu Val Thr Val Ser Ser
        115

<210> SEQ ID NO 18
<211> LENGTH: 109
<212> TYPE: PRT
<213> ORGANISM: Artificial Sequnce
<220> FEATURE:
<223> OTHER INFORMATION: an artificially synthesized sequence

<400> SEQUENCE: 18

Gln Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Leu His Trp Tyr Gln Gln Lys Pro Gly Lys Ala Pro Lys Leu Trp
```

```
                35                  40                  45
Ile Tyr Ser Thr Ser Asn Leu Ala Ser Gly Val Pro Ser Arg Phe Ser
        50                  55                  60
Gly Ser Gly Ser Gly Thr Asp Tyr Thr Leu Thr Ile Ser Ser Leu Gln
65                  70                  75                  80
Pro Glu Asp Phe Ala Thr Tyr Tyr Cys His Gln Tyr Tyr Arg Leu His
                85                  90                  95
Pro Ile Thr Phe Gly Gln Gly Thr Lys Leu Glu Ile Lys
            100                 105

<210> SEQ ID NO 19
<211> LENGTH: 118
<212> TYPE: PRT
<213> ORGANISM: Artificial Sequnce
<220> FEATURE:
<223> OTHER INFORMATION: an artificially synthesized sequence

<400> SEQUENCE: 19

Glu Val Met Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asn Tyr
            20                  25                  30
Ala Met Ser Trp Val Arg Gln Ala Pro Gly Lys Gly Leu Glu Trp Val
        35                  40                  45
Ala Thr Ile Ser Ser Gly Gly Ser His Thr Tyr Glu Leu Asp Ser Val
    50                  55                  60
Asp Gly Arg Phe Thr Ile Ser Arg Asp Asn Ser Lys Asp Thr Leu Tyr
65                  70                  75                  80
Leu Gln Met Asn Ser Leu Arg Ala Glu Asp Thr Ala Leu Tyr Tyr Cys
                85                  90                  95
Ala Arg Leu Phe Thr Lys His Ala Met Asp Tyr Trp Gly Gln Gly Thr
            100                 105                 110
Leu Val Thr Val Ser Ser
        115

<210> SEQ ID NO 20
<211> LENGTH: 109
<212> TYPE: PRT
<213> ORGANISM: Artificial Sequnce
<220> FEATURE:
<223> OTHER INFORMATION: an artificially synthesized sequence

<400> SEQUENCE: 20

Gln Ile Val Leu Thr Gln Ser Pro Ala Thr Leu Ser Leu Ser Pro Gly
1               5                   10                  15
Glu Arg Ala Thr Leu Ser Cys Thr Ala Ser Ser Glu Val Ser Glu Ser
            20                  25                  30
Tyr Leu His Trp Tyr Gln Gln Lys Pro Gly Lys Ala Pro Lys Leu Trp
        35                  40                  45
Ile Tyr Ser Thr Ser Asn Leu Ala Ser Gly Val Pro Ser Arg Phe Ser
    50                  55                  60
Gly Ser Gly Ser Gly Thr Asp Tyr Thr Leu Thr Ile Ser Ser Leu Gln
65                  70                  75                  80
Pro Glu Asp Phe Ala Thr Tyr Tyr Cys His Gln Tyr Tyr Arg Leu His
                85                  90                  95
Pro Ile Thr Phe Gly Gln Gly Thr Lys Leu Glu Ile Lys
            100                 105
```

<210> SEQ ID NO 21
<211> LENGTH: 109
<212> TYPE: PRT
<213> ORGANISM: Artificial Sequnce
<220> FEATURE:
<223> OTHER INFORMATION: an artificially synthesized sequence

<400> SEQUENCE: 21

Gln Ile Val Leu Thr Gln Ser Pro Ala Thr Leu Ser Leu Ser Pro Gly
1               5                   10                  15

Glu Arg Ala Thr Leu Ser Cys Thr Ala Ser Ser Glu Val Ser Ser Ser
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr Tyr Arg Leu His
                85                  90                  95

Pro Ile Thr Phe Gly Gln Gly Thr Lys Leu Glu Ile Lys
            100                 105

<210> SEQ ID NO 22
<211> LENGTH: 118
<212> TYPE: PRT
<213> ORGANISM: Artificial Sequnce
<220> FEATURE:
<223> OTHER INFORMATION: an artificially synthesized sequence

<400> SEQUENCE: 22

Glu Val Met Leu Val Glu Ser Gly Gly Gly Leu Val Lys Pro Gly Gly
1               5                   10                  15

Ser Leu Arg Leu Ser Cys Ala Ala Ser Gly Phe Glu Phe Glu Asn Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Ser His Thr Tyr Glu Leu Asp Ser Val
    50                  55                  60

Asp Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Leu Tyr Tyr Cys
                85                  90                  95

Ala Arg Leu Phe Thr Lys His Ala Met Asp Tyr Trp Gly Gln Gly Thr
            100                 105                 110

Leu Val Thr Val Ser Ser
        115

<210> SEQ ID NO 23
<211> LENGTH: 5
<212> TYPE: PRT
<213> ORGANISM: Artificial Sequnce
<220> FEATURE:
<223> OTHER INFORMATION: an artificially synthesized sequence

<400> SEQUENCE: 23

Asn Tyr Ala Met Ser
1               5

```
<210> SEQ ID NO 24
<211> LENGTH: 17
<212> TYPE: PRT
<213> ORGANISM: Artificial Sequnce
<220> FEATURE:
<223> OTHER INFORMATION: an artificially synthesized sequence

<400> SEQUENCE: 24

Thr Ile Ser Ser Gly Gly Ser His Thr Tyr Tyr Leu Asp Ser Val Lys
1               5                   10                  15
Gly

<210> SEQ ID NO 25
<211> LENGTH: 9
<212> TYPE: PRT
<213> ORGANISM: Artificial Sequnce
<220> FEATURE:
<223> OTHER INFORMATION: an artificially synthesized sequence

<400> SEQUENCE: 25

Leu Phe Thr Gly Tyr Ala Met Asp Tyr
1               5

<210> SEQ ID NO 26
<211> LENGTH: 12
<212> TYPE: PRT
<213> ORGANISM: Artificial Sequnce
<220> FEATURE:
<223> OTHER INFORMATION: an artificially synthesized sequence

<400> SEQUENCE: 26

Thr Ala Ser Ser Ser Val Ser Ser Ser Tyr Leu His
1               5                   10

<210> SEQ ID NO 27
<211> LENGTH: 7
<212> TYPE: PRT
<213> ORGANISM: Artificial Sequnce
<220> FEATURE:
<223> OTHER INFORMATION: an artificially synthesized sequence

<400> SEQUENCE: 27

Ser Thr Ser Asn Leu Ala Ser
1               5

<210> SEQ ID NO 28
<211> LENGTH: 10
<212> TYPE: PRT
<213> ORGANISM: Artificial Sequnce
<220> FEATURE:
<223> OTHER INFORMATION: an artificially synthesized sequence

<400> SEQUENCE: 28

His Gln Tyr Tyr Arg Leu Pro Pro Ile Thr
1               5                   10

<210> SEQ ID NO 29
<211> LENGTH: 12
<212> TYPE: PRT
<213> ORGANISM: Artificial Sequnce
<220> FEATURE:
<223> OTHER INFORMATION: an artificially synthesized sequence

<400> SEQUENCE: 29

Gly Phe Asn Ile Lys Asp Asp Tyr Ile His Trp Val
1               5                   10
```

<210> SEQ ID NO 30
<211> LENGTH: 10
<212> TYPE: PRT
<213> ORGANISM: Artificial Sequnce
<220> FEATURE:
<223> OTHER INFORMATION: an artificially synthesized sequence

<400> SEQUENCE: 30

Ile Asp Pro Ala Asp Asp His Thr Lys Tyr
1               5                   10

<210> SEQ ID NO 31
<211> LENGTH: 12
<212> TYPE: PRT
<213> ORGANISM: Artificial Sequnce
<220> FEATURE:
<223> OTHER INFORMATION: an artificially synthesized sequence

<400> SEQUENCE: 31

Ala Ile Tyr Gly Ser Gly Trp Ala Trp Phe Pro Tyr
1               5                   10

<210> SEQ ID NO 32
<211> LENGTH: 12
<212> TYPE: PRT
<213> ORGANISM: Artificial Sequnce
<220> FEATURE:
<223> OTHER INFORMATION: an artificially synthesized sequence

<400> SEQUENCE: 32

Gln Ser Val Asp Tyr Asp Gly Asp Ser Tyr Met Asn
1               5                   10

<210> SEQ ID NO 33
<211> LENGTH: 10
<212> TYPE: PRT
<213> ORGANISM: Artificial Sequnce
<220> FEATURE:
<223> OTHER INFORMATION: an artificially synthesized sequence

<400> SEQUENCE: 33

Ala Ala Ser Asn Leu Glu Ser Gly Ile Pro
1               5                   10

<210> SEQ ID NO 34
<211> LENGTH: 9
<212> TYPE: PRT
<213> ORGANISM: Artificial Sequnce
<220> FEATURE:
<223> OTHER INFORMATION: an artificially synthesized sequence

<400> SEQUENCE: 34

Gln Gln Ser Asn Glu Asp Pro Trp Thr
1               5

<210> SEQ ID NO 35
<211> LENGTH: 118
<212> TYPE: PRT
<213> ORGANISM: Artificial Sequnce
<220> FEATURE:
<223> OTHER INFORMATION: an artificially synthesized sequence

<400> SEQUENCE: 35

Glu Val Met Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr

```
                 20                  25                  30
Ala Met Ser Trp Val Arg Gln Ala Pro Gly Lys Gly Leu Glu Trp Val
             35                  40                  45

Ala Thr Ile Ser Ser Gly Gly Ser His Thr Tyr Tyr Leu Asp Ser Val
         50                  55                  60

Lys Gly Arg Phe Thr Ile Ser Arg Asp Asn Ser Lys Asp Thr Leu Tyr
 65                  70                  75                  80

Leu Gln Met Asn Ser Leu Arg Ala Glu Asp Thr Ala Leu Tyr Tyr Cys
                 85                  90                  95

Ala Arg Leu Phe Thr Gly Tyr Ala Met Asp Tyr Trp Gly Gln Gly Thr
            100                 105                 110

Leu Val Thr Val Ser Ser
            115

<210> SEQ ID NO 36
<211> LENGTH: 118
<212> TYPE: PRT
<213> ORGANISM: Artificial Sequnce
<220> FEATURE:
<223> OTHER INFORMATION: an artificially synthesized sequence

<400> SEQUENCE: 36

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
             20                  25                  30

Ala Met Ser Trp Val Arg Gln Ala Pro Gly Lys Gly Leu Glu Trp Val
             35                  40                  45

Ala Thr Ile Ser Ser Gly Gly Ser His Thr Tyr Tyr Leu Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Arg Leu Phe Thr Gly Tyr Ala Met Asp Tyr Trp Gly Gln Gly Thr
            100                 105                 110

Leu Val Thr Val Ser Ser
            115

<210> SEQ ID NO 37
<211> LENGTH: 109
<212> TYPE: PRT
<213> ORGANISM: Artificial Sequnce
<220> FEATURE:
<223> OTHER INFORMATION: an artificially synthesized sequence

<400> SEQUENCE: 37

Gln Ile Val Leu Thr Gln Ser Pro Ala Thr Leu Ser Leu Ser Pro Gly
 1               5                  10                  15

Glu Arg Ala Thr Leu Ser Cys Thr Ala Ser Ser Ser Val Ser Ser Ser
             20                  25                  30

Tyr Leu His Trp Tyr Gln Gln Lys Pro Gly Lys Ala Pro Lys Leu Trp
             35                  40                  45

Ile Tyr Ser Thr Ser Asn Leu Ala Ser Gly Val Pro Ser Arg Phe Ser
         50                  55                  60

Gly Ser Gly Ser Gly Thr Asp Tyr Thr Leu Thr Ile Ser Ser Leu Gln
 65                  70                  75                  80
```

Pro Glu Asp Phe Ala Thr Tyr Tyr Cys His Gln Tyr Tyr Arg Leu Pro
            85                  90                  95

Pro Ile Thr Phe Gly Gln Gly Thr Lys Leu Glu Ile Lys
            100                 105

<210> SEQ ID NO 38
<211> LENGTH: 109
<212> TYPE: PRT
<213> ORGANISM: Artificial Sequnce
<220> FEATURE:
<223> OTHER INFORMATION: an artificially synthesized sequence

<400> SEQUENCE: 38

Gln Ile Val Leu Thr Gln Ser Pro Ala Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr Tyr Arg Leu Pro
            85                  90                  95

Pro Ile Thr Phe Gly Gln Gly Thr Lys Leu Glu Ile Lys
            100                 105

<210> SEQ ID NO 39
<211> LENGTH: 5
<212> TYPE: PRT
<213> ORGANISM: Artificial Sequnce
<220> FEATURE:
<223> OTHER INFORMATION: an artificially synthesized sequence

<400> SEQUENCE: 39

Asn Tyr Ala Met Ser
1               5

<210> SEQ ID NO 40
<211> LENGTH: 17
<212> TYPE: PRT
<213> ORGANISM: Artificial Sequnce
<220> FEATURE:
<223> OTHER INFORMATION: an artificially synthesized sequence

<400> SEQUENCE: 40

Thr Ile Ser Ser Gly Gly Ser His Thr Tyr Glu Leu Asp Ser Val Asp
1               5                   10                  15

Gly

<210> SEQ ID NO 41
<211> LENGTH: 9
<212> TYPE: PRT
<213> ORGANISM: Artificial Sequnce
<220> FEATURE:
<223> OTHER INFORMATION: an artificially synthesized sequence

<400> SEQUENCE: 41

Leu Phe Thr Lys His Ala Met Asp Tyr
1               5

```
<210> SEQ ID NO 42
<211> LENGTH: 12
<212> TYPE: PRT
<213> ORGANISM: Artificial Sequnce
<220> FEATURE:
<223> OTHER INFORMATION: an artificially synthesized sequence

<400> SEQUENCE: 42

Thr Ala Ser Ser Glu Val Ser Glu Ser Tyr Leu His
1               5                   10

<210> SEQ ID NO 43
<211> LENGTH: 7
<212> TYPE: PRT
<213> ORGANISM: Artificial Sequnce
<220> FEATURE:
<223> OTHER INFORMATION: an artificially synthesized sequence

<400> SEQUENCE: 43

Ser Thr Ser Asn Leu Ala Ser
1               5

<210> SEQ ID NO 44
<211> LENGTH: 10
<212> TYPE: PRT
<213> ORGANISM: Artificial Sequnce
<220> FEATURE:
<223> OTHER INFORMATION: an artificially synthesized sequence

<400> SEQUENCE: 44

His Gln Tyr Tyr Arg Leu His Pro Ile Thr
1               5                   10

<210> SEQ ID NO 45
<211> LENGTH: 12
<212> TYPE: PRT
<213> ORGANISM: Artificial Sequnce
<220> FEATURE:
<223> OTHER INFORMATION: an artificially synthesized sequence

<400> SEQUENCE: 45

Thr Ala Ser Ser Glu Val Ser Ser Ser Tyr Leu His
1               5                   10

<210> SEQ ID NO 46
<211> LENGTH: 115
<212> TYPE: PRT
<213> ORGANISM: Artificial sequence
<220> FEATURE:
<223> OTHER INFORMATION: an artificially synthesized sequence

<400> SEQUENCE: 46

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Thr Lys Tyr Thr
            20                  25                  30

Val Ser Trp Val Arg Gln Ala Pro Gly Lys Gly Leu Glu Trp Ile Gly
        35                  40                  45

Ile Ile Asn Thr Gly Gly Ser Ala Tyr Tyr Ala Thr Trp Ala Lys Gly
    50                  55                  60

Arg Phe Thr Phe Ser Lys Thr Ser Thr Thr Val Asp Leu Gln Ile Thr
65                  70                  75                  80

Ser Pro Thr Thr Glu Asp Thr Ala Thr Tyr Phe Cys Ala Arg Gly Asn
                85                  90                  95
```

Gly Asp Thr Asp Tyr Thr Asn Leu Trp Gly Pro Gly Thr Leu Val Thr
            100                 105                 110

Val Ser Ser
        115

<210> SEQ ID NO 47
<211> LENGTH: 117
<212> TYPE: PRT
<213> ORGANISM: Artificial sequence
<220> FEATURE:
<223> OTHER INFORMATION: an artificially synthesized sequence

<400> SEQUENCE: 47

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Pro
            20                  25                  30

Met Gly Trp Val Arg Gln Val Pro Gly Glu Gly Leu Glu Trp Ile Gly
        35                  40                  45

Thr Ile Ser Ala Gly Gly Ser Thr Tyr Tyr Pro Ser Trp Ala Lys Gly
    50                  55                  60

Arg Phe Thr Ile Ser Arg Thr Ser Thr Thr Val Asp Leu Lys Met Thr
65                  70                  75                  80

Ser Leu Thr Thr Glu Asp Thr Ala Thr Tyr Phe Cys Ala Arg Gly Tyr
                85                  90                  95

Pro Tyr Thr Asp Gly Thr Tyr Met Thr Leu Trp Gly Pro Gly Thr Leu
            100                 105                 110

Val Thr Val Ser Ser
        115

<210> SEQ ID NO 48
<211> LENGTH: 118
<212> TYPE: PRT
<213> ORGANISM: Artificial sequence
<220> FEATURE:
<223> OTHER INFORMATION: an artificially synthesized sequence

<400> SEQUENCE: 48

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn Asn Tyr Pro
            20                  25                  30

Met Gly Trp Val Arg Gln Ala Pro Gly Lys Gly Leu Glu Tyr Ile Gly
        35                  40                  45

Ile Ile Ser Ser Ser Gly Gly Thr Ser Tyr Ala Ser Trp Ala Lys Gly
    50                  55                  60

Arg Phe Thr Ile Ser Lys Thr Ser Ser Thr Val Asp Leu Lys Met Thr
65                  70                  75                  80

Thr Ser Leu Thr Thr Glu Asp Thr Ala Thr Tyr Phe Cys Ala Arg Gly
                85                  90                  95

Tyr Pro Tyr Arg Asp Ile Thr Tyr Phe Asn Leu Trp Gly Pro Gly Thr
            100                 105                 110

Leu Val Thr Val Ser Ser
        115

<210> SEQ ID NO 49
<211> LENGTH: 113
<212> TYPE: PRT
<213> ORGANISM: Artificial sequence
<220> FEATURE:
<223> OTHER INFORMATION: an artificially synthesized sequence

<400> SEQUENCE: 49

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Thr
                20                  25                  30

Met Ile Trp Val Arg Gln Ala Pro Gly Lys Gly Leu Glu Trp Ile Gly
            35                  40                  45

Val Val Gly Gly Ser Gly Ile Thr Tyr Tyr Ala Ser Trp Ala Lys Gly
        50                  55                  60

Arg Phe Thr Ile Ser Lys Thr Ser Thr Thr Val Asp Leu Gln Ile Thr
65              70                  75                  80

Ser Pro Thr Thr Glu Asp Thr Ala Thr Tyr Phe Cys Ala Arg Asp Thr
                85                  90                  95

Ser Val Ala Gly Asp Leu Trp Gly Pro Gly Thr Leu Val Thr Val Ser
            100                 105                 110

Ser

<210> SEQ ID NO 50
<211> LENGTH: 117
<212> TYPE: PRT
<213> ORGANISM: Artificial sequence
<220> FEATURE:
<223> OTHER INFORMATION: an artificially synthesized sequence

<400> SEQUENCE: 50

Gln Ser Val Glu Glu Ser Gly Gly Arg Leu Val Thr Pro Gly Gly Ser
1               5                   10                  15

Leu Thr Leu Thr Cys Thr Val Ser Gly Phe Ser Leu Ser Arg Asn Ala
                20                  25                  30

Ile Asn Trp Val Arg Gln Ala Pro Gly Lys Gly Leu Glu Trp Ile Gly
            35                  40                  45

Gly Val Ser Gly Gly Ala Thr Thr Tyr Tyr Ala Ser Trp Ala Asn Gly
        50                  55                  60

Arg Phe Thr Ile Ser Lys Thr Ser Thr Thr Val Asp Leu Lys Met Thr
65              70                  75                  80

Gly Leu Thr Ala Ala Asp Thr Ala Thr Tyr Phe Cys Ala Arg Gly Ala
                85                  90                  95

Gly Ser Asn Ile Asp Gly Pro Phe Asn Leu Trp Gly Pro Gly Thr Leu
            100                 105                 110

Val Thr Val Ser Ser
        115

<210> SEQ ID NO 51
<211> LENGTH: 106
<212> TYPE: PRT
<213> ORGANISM: Artificial sequence
<220> FEATURE:
<223> OTHER INFORMATION: an artificially synthesized sequence

<400> SEQUENCE: 51

Gln Val Leu Thr Gln Thr Pro Ser Ser Val Ser Glu Pro Val Gly Gly
1               5                   10                  15

Thr Val Thr Ile Asn Cys Gln Ala Ser Glu Asn Ile Tyr Ser Ala Leu
                20                  25                  30

Ala Trp Tyr Gln Gln Lys Pro Gly Gln Pro Pro Lys Leu Leu Ile Tyr

```
                35                  40                  45
Gly Ala Ser Asn Leu Glu Ser Gly Val Pro Ser Arg Phe Lys Gly Ser
             50                  55                  60
Gly Ser Gly Thr Gln Phe Thr Leu Thr Ile Ser Asp Leu Glu Cys Ala
 65                  70                  75                  80
Asp Ala Ala Thr Tyr Tyr Cys Gln Gln Tyr Tyr Phe Thr Ser Ser Thr
                 85                  90                  95
Phe Gly Gly Gly Thr Lys Val Glu Ile Lys
            100                 105

<210> SEQ ID NO 52
<211> LENGTH: 108
<212> TYPE: PRT
<213> ORGANISM: Artificial sequence
<220> FEATURE:
<223> OTHER INFORMATION: an artificially synthesized sequence

<400> SEQUENCE: 52

Ala Phe Glu Leu Thr Gln Thr Pro Ser Ser Val Glu Ala Ala Val Gly
 1               5                  10                  15
Gly Thr Val Thr Ile Lys Cys Gln Ala Ser Glu Asn Ile Tyr Ser Leu
             20                  25                  30
Leu Ala Trp Tyr Gln Gln Lys Pro Gly Gln Pro Pro Lys Leu Leu Ile
         35                  40                  45
Tyr Gly Ala Ser Thr Leu Ala Ser Gly Val Ser Ser Arg Phe Ser Gly
     50                  55                  60
Ser Gly Tyr Gly Thr Glu Phe Thr Leu Thr Ile Ser Asp Leu Glu Cys
 65                  70                  75                  80
Ala Asp Ala Ala Thr Tyr Tyr Cys Gln Ser Tyr Tyr Asp Ser Ser Thr
                 85                  90                  95
Thr Thr Phe Gly Gly Gly Thr Lys Val Glu Ile Lys
            100                 105

<210> SEQ ID NO 53
<211> LENGTH: 110
<212> TYPE: PRT
<213> ORGANISM: Artificial sequence
<220> FEATURE:
<223> OTHER INFORMATION: an artificially synthesized sequence

<400> SEQUENCE: 53

Asp Pro Val Leu Thr Gln Thr Pro Ser Pro Val Ser Ala Pro Val Gly
 1               5                  10                  15
Gly Ser Val Thr Ile Lys Cys Gln Ala Ser Gln Asn Ile Tyr Ser Tyr
             20                  25                  30
Leu Ser Trp Tyr Gln His Lys Pro Gly Gln Pro Pro Lys Leu Leu Ile
         35                  40                  45
Tyr Gly Ala Ser Thr Leu Thr Asn Gly Val Ser Ser Arg Phe Thr Gly
     50                  55                  60
Ser Gly Tyr Gly Thr Glu Phe Thr Leu Thr Ile Ser Asp Leu Glu Cys
 65                  70                  75                  80
Glu Asp Ala Ala Thr Tyr Tyr Cys Gln Asn Tyr Tyr Ser Gly Gly Ser
                 85                  90                  95
Ala Asp Thr Thr Phe Gly Gly Gly Thr Lys Val Glu Ile Lys
            100                 105                 110

<210> SEQ ID NO 54
<211> LENGTH: 110
```

```
<212> TYPE: PRT
<213> ORGANISM: Artificial sequence
<220> FEATURE:
<223> OTHER INFORMATION: an artificially synthesized sequence

<400> SEQUENCE: 54

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Gly Val Ser
            20                  25                  30

Leu Ala Trp Tyr Gln Gln Lys Pro Gly Gln Arg Pro Lys Leu Leu Ile
        35                  40                  45

Tyr Lys Ala Ser Asn Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Asp Tyr Thr Tyr Ser Asp
                85                  90                  95

Val Thr Asn Ile Phe Gly Gly Gly Thr Lys Val Glu Ile Lys
            100                 105                 110

<210> SEQ ID NO 55
<211> LENGTH: 108
<212> TYPE: PRT
<213> ORGANISM: Artificial sequence
<220> FEATURE:
<223> OTHER INFORMATION: an artificially synthesized sequence

<400> SEQUENCE: 55

Ala Phe Glu Met Thr Gln Thr Pro Ser Ser Val Ser Ala Pro Val Gly
1               5                   10                  15

Gly Thr Val Thr Ile Lys Cys Gln Ala Ser Gln Asn Ile Tyr Ser Tyr
            20                  25                  30

Leu Ser Trp Tyr Gln Gln Lys Pro Gly His Pro Pro Lys Leu Leu Ile
        35                  40                  45

Tyr Gly Ala Ser Thr Leu Ala Ser Gly Val Pro Ser Arg Phe Lys Gly
    50                  55                  60

Ser Gly Tyr Gly Thr Glu Phe Thr Leu Thr Ile Ser Asp Leu Glu Cys
65                  70                  75                  80

Ala Asp Pro Ala Thr Tyr Tyr Cys Gln Gln Tyr Tyr Ala Thr Thr Ser
                85                  90                  95

Val Asp Phe Gly Gly Gly Thr Lys Val Glu Ile Lys
            100                 105

<210> SEQ ID NO 56
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 56

Lys Tyr Thr Val Ser
1               5

<210> SEQ ID NO 57
<211> LENGTH: 16
<212> TYPE: PRT
<213> ORGANISM: Artificial sequence
<220> FEATURE:
<223> OTHER INFORMATION: an artificially synthesized sequence
```

<400> SEQUENCE: 57

Ile Ile Asn Thr Gly Gly Ser Ala Tyr Tyr Ala Thr Trp Ala Lys Gly
1               5                   10                  15

<210> SEQ ID NO 58
<211> LENGTH: 10
<212> TYPE: PRT
<213> ORGANISM: Artificial sequence
<220> FEATURE:
<223> OTHER INFORMATION: an artificially synthesized sequence

<400> SEQUENCE: 58

Gly Asn Gly Asp Thr Asp Tyr Thr Asn Leu
1               5                   10

<210> SEQ ID NO 59
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 59

Ser Tyr Pro Met Gly
1               5

<210> SEQ ID NO 60
<211> LENGTH: 16
<212> TYPE: PRT
<213> ORGANISM: Artificial sequence
<220> FEATURE:
<223> OTHER INFORMATION: an artificially synthesized sequence

<400> SEQUENCE: 60

Thr Ile Ser Ala Gly Gly Ser Thr Tyr Tyr Pro Ser Trp Ala Lys Gly
1               5                   10                  15

<210> SEQ ID NO 61
<211> LENGTH: 12
<212> TYPE: PRT
<213> ORGANISM: Artificial sequence
<220> FEATURE:
<223> OTHER INFORMATION: an artificially synthesized sequence

<400> SEQUENCE: 61

Gly Tyr Pro Tyr Thr Asp Gly Thr Tyr Met Thr Leu
1               5                   10

<210> SEQ ID NO 62
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 62

Asn Tyr Pro Met Gly
1               5

<210> SEQ ID NO 63
<211> LENGTH: 16
<212> TYPE: PRT
<213> ORGANISM: Artificial sequence
<220> FEATURE:
<223> OTHER INFORMATION: an artificially synthesized sequence

```
<400> SEQUENCE: 63

Ile Ile Ser Ser Ser Gly Gly Thr Ser Tyr Ala Ser Trp Ala Lys Gly
1               5                   10                  15

<210> SEQ ID NO 64
<211> LENGTH: 12
<212> TYPE: PRT
<213> ORGANISM: Artificial sequence
<220> FEATURE:
<223> OTHER INFORMATION: an artificially synthesized sequence

<400> SEQUENCE: 64

Gly Tyr Pro Tyr Arg Asp Ile Thr Tyr Phe Asn Leu
1               5                   10

<210> SEQ ID NO 65
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 65

Ser Tyr Thr Met Ile
1               5

<210> SEQ ID NO 66
<211> LENGTH: 16
<212> TYPE: PRT
<213> ORGANISM: Artificial sequence
<220> FEATURE:
<223> OTHER INFORMATION: an artificially synthesized sequence

<400> SEQUENCE: 66

Val Val Gly Gly Ser Gly Ile Thr Tyr Tyr Ala Ser Trp Ala Lys Gly
1               5                   10                  15

<210> SEQ ID NO 67
<211> LENGTH: 8
<212> TYPE: PRT
<213> ORGANISM: Artificial sequence
<220> FEATURE:
<223> OTHER INFORMATION: an artificially synthesized sequence

<400> SEQUENCE: 67

Asp Thr Ser Val Ala Gly Asp Leu
1               5

<210> SEQ ID NO 68
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 68

Arg Asn Ala Ile Asn
1               5

<210> SEQ ID NO 69
<211> LENGTH: 16
<212> TYPE: PRT
<213> ORGANISM: Artificial sequence
<220> FEATURE:
<223> OTHER INFORMATION: an artificially synthesized sequence

<400> SEQUENCE: 69
```

```
Gly Val Ser Gly Gly Ala Thr Thr Tyr Tyr Ala Ser Trp Ala Asn Gly
1               5                   10                  15
```

<210> SEQ ID NO 70
<211> LENGTH: 12
<212> TYPE: PRT
<213> ORGANISM: Artificial sequence
<220> FEATURE:
<223> OTHER INFORMATION: an artificially synthesized sequence

<400> SEQUENCE: 70

```
Gly Ala Gly Ser Asn Ile Asp Gly Pro Phe Asn Leu
1               5                   10
```

<210> SEQ ID NO 71
<211> LENGTH: 11
<212> TYPE: PRT
<213> ORGANISM: Artificial sequence
<220> FEATURE:
<223> OTHER INFORMATION: an artificially synthesized sequence

<400> SEQUENCE: 71

```
Gln Ala Ser Glu Asn Ile Tyr Ser Ala Leu Ala
1               5                   10
```

<210> SEQ ID NO 72
<211> LENGTH: 7
<212> TYPE: PRT
<213> ORGANISM: Artificial sequence
<220> FEATURE:
<223> OTHER INFORMATION: an artificially synthesized sequence

<400> SEQUENCE: 72

```
Gly Ala Ser Asn Leu Glu Ser
1               5
```

<210> SEQ ID NO 73
<211> LENGTH: 9
<212> TYPE: PRT
<213> ORGANISM: Artificial sequence
<220> FEATURE:
<223> OTHER INFORMATION: an artificially synthesized sequence

<400> SEQUENCE: 73

```
Gln Gln Tyr Tyr Phe Thr Ser Ser Thr
1               5
```

<210> SEQ ID NO 74
<211> LENGTH: 11
<212> TYPE: PRT
<213> ORGANISM: Artificial sequence
<220> FEATURE:
<223> OTHER INFORMATION: an artificially synthesized sequence

<400> SEQUENCE: 74

```
Gln Ala Ser Glu Asn Ile Tyr Ser Leu Leu Ala
1               5                   10
```

<210> SEQ ID NO 75
<211> LENGTH: 7
<212> TYPE: PRT
<213> ORGANISM: Artificial sequence
<220> FEATURE:
<223> OTHER INFORMATION: an artificially synthesized sequence

<400> SEQUENCE: 75

Gly Ala Ser Thr Leu Ala Ser
1               5

<210> SEQ ID NO 76
<211> LENGTH: 10
<212> TYPE: PRT
<213> ORGANISM: Artificial sequence
<220> FEATURE:
<223> OTHER INFORMATION: an artificially synthesized sequence

<400> SEQUENCE: 76

Gln Ser Tyr Tyr Asp Ser Ser Thr Thr Thr
1               5                   10

<210> SEQ ID NO 77
<211> LENGTH: 11
<212> TYPE: PRT
<213> ORGANISM: Artificial sequence
<220> FEATURE:
<223> OTHER INFORMATION: an artificially synthesized sequence

<400> SEQUENCE: 77

Gln Ala Ser Gln Asn Ile Tyr Ser Tyr Leu Ser
1               5                   10

<210> SEQ ID NO 78
<211> LENGTH: 7
<212> TYPE: PRT
<213> ORGANISM: Artificial sequence
<220> FEATURE:
<223> OTHER INFORMATION: an artificially synthesized sequence

<400> SEQUENCE: 78

Gly Ala Ser Thr Leu Thr Asn
1               5

<210> SEQ ID NO 79
<211> LENGTH: 12
<212> TYPE: PRT
<213> ORGANISM: Artificial sequence
<220> FEATURE:
<223> OTHER INFORMATION: an artificially synthesized sequence

<400> SEQUENCE: 79

Gln Asn Tyr Tyr Ser Gly Gly Ser Ala Asp Thr Thr
1               5                   10

<210> SEQ ID NO 80
<211> LENGTH: 11
<212> TYPE: PRT
<213> ORGANISM: Artificial sequence
<220> FEATURE:
<223> OTHER INFORMATION: an artificially synthesized sequence

<400> SEQUENCE: 80

Gln Ala Ser Gln Ser Ile Gly Val Ser Leu Ala
1               5                   10

<210> SEQ ID NO 81
<211> LENGTH: 7
<212> TYPE: PRT
<213> ORGANISM: Artificial sequence
<220> FEATURE:
<223> OTHER INFORMATION: an artificially synthesized sequence

<400> SEQUENCE: 81

Lys Ala Ser Asn Leu Ala Ser

-continued

<210> SEQ ID NO 82
<211> LENGTH: 12
<212> TYPE: PRT
<213> ORGANISM: Artificial sequence
<220> FEATURE:
<223> OTHER INFORMATION: an artificially synthesized sequence

<400> SEQUENCE: 82

Gln Gln Asp Tyr Thr Tyr Ser Asp Val Thr Asn Ile
1               5                   10

<210> SEQ ID NO 83
<211> LENGTH: 11
<212> TYPE: PRT
<213> ORGANISM: Artificial sequence
<220> FEATURE:
<223> OTHER INFORMATION: an artificially synthesized sequence

<400> SEQUENCE: 83

Gln Ala Ser Gln Asn Ile Tyr Ser Tyr Leu Ser
1               5                   10

<210> SEQ ID NO 84
<211> LENGTH: 7
<212> TYPE: PRT
<213> ORGANISM: Artificial sequence
<220> FEATURE:
<223> OTHER INFORMATION: an artificially synthesized sequence

<400> SEQUENCE: 84

Gly Ala Ser Thr Leu Ala Ser
1               5

<210> SEQ ID NO 85
<211> LENGTH: 10
<212> TYPE: PRT
<213> ORGANISM: Artificial sequence
<220> FEATURE:
<223> OTHER INFORMATION: an artificially synthesized sequence

<400> SEQUENCE: 85

Gln Gln Tyr Tyr Ala Thr Thr Ser Val Asp
1               5                   10

<210> SEQ ID NO 86
<211> LENGTH: 328
<212> TYPE: PRT
<213> ORGANISM: Artificial sequence
<220> FEATURE:
<223> OTHER INFORMATION: an artificially synthesized sequence

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Glu Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 87
<211> LENGTH: 328
<212> TYPE: PRT
<213> ORGANISM: Artificial sequence
<220> FEATURE:
<223> OTHER INFORMATION: an artificially synthesized sequence

<400> SEQUENCE: 87

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Arg Arg Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 88
<211> LENGTH: 107
<212> TYPE: PRT
<213> ORGANISM: Artificial sequence
<220> FEATURE:
<223> OTHER INFORMATION: an artificially synthesized sequence

<400> SEQUENCE: 88

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Cys
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

ANTI-C1S ANTIBODIES AND METHODS OF USE

CROSS-REFERENCE TO RELATED APPLICATIONS

This application is a U.S. National Phase of PCT Application No. PCT/JP2018/042054, filed Nov. 14, 2018, which claims the benefit of Japanese Patent Application No. 2017-219507, filed Nov. 14, 2017, and Japanese Patent Application No. 2018-188765, filed Oct. 4, 2018, each of which is incorporated herein by reference in its entirety.

REFERENCE TO SEQUENCE LISTING SUBMITTED ELECTRONICALLY

The content of the electronically submitted sequence listing (Name: 6663_0136 Sequence_Listing.txt; Size: 64.7 kilobytes; and Date of Creation: May 11, 2020) filed with the application is incorporated herein by reference in its entirety.

TECHNICAL FIELD

The present invention relates to anti-C1s antibodies and methods of using the same.

BACKGROUND

The complement system comprises about 25-30 complement proteins which play a critical role in host defense against pathogens, foreign antigens and tumor cells. The complement system is also involved in the maintenance of homeostasis by clearing immune complexes and apoptotic cells from the body. Complement components perform these functions by interacting in a cascading series of enzymatic processes and membrane binding events. The end result of these processes is the generation of products with lytic, immunoregulatory, and opsonic functions.

It is widely known that the complement system can be divided into three distinct pathways: the classical pathway, the lectin pathway, and the alternative pathway. Although the initiation of each pathway is distinct, all three pathways converge and share the same terminal complement components (C5 through C9), which is ultimately responsible for the destruction of the target cell.

The C1 complex is a large protein complex which functions as the key initiator of the classical pathway cascade. The C1 complex consists of three components, C1q, C1r and C1s, which are in molar ratio of 1:2:2 respectively (Non Patent Literature 1). The classical pathway is initiated when the C1 complex binds to a target that is bound by antibodies. C1q, which has 6 globular heads, mediates the binding of C1 complex to the antibodies by avidity interaction with the Fc regions. Once tightly bound to the target, C1r within the C1 complex autoactivates and become enzymatically active. The activated C1r then cleaves and activates proenzyme C1s within the C1 complex (Non Patent Literature 2). Subsequently, active C1s cleave its substrates complement component C2 and C4 into C2a/C2b, and C4a/C4b fragments respectively. This leads to the assembly of C4b2a, a C3 convertase, on the target surface which cleaves C3 to form C3b. C3b in turn cleaves C5 to initiate the formation of the terminal membrane attack complex, C5b, C6, C7, C8 and C9, which lyses the target via pore formation.

C1s forms homodimers in a calcium dependent manner (Non Patent Literature 3). It is reported that at 1 mM calcium ion concentration, the majority of C1s is in a dimeric state, whereas at 1 nM calcium concentration, it is mainly in monomeric state (Non Patent Literature 4). Within the circulation, C1s and C1r are mostly bound together as a calcium dependent C1r2s2 heterotetramer, which in turn reversibly binds to C1q at 1:1 ratio to form the C1 complex. In the absence or at low concentrations of calcium, the C1r2s2 tetramer dissociates into one C1r dimer and two C1s monomers (Non Patent Literature 5). C1s is a 79 kDa glycoprotein, with 5 to 6% of its mass attributable to glycosylation (Non Patent Literature 6). The concentration of C1s in serum is reported to be approximately 55 micro g/mL (0.7 micro M) (Non Patent Literature 7).

While a properly functioning complement system defends the host against pathogens, dysregulation or inappropriate activation of the classical pathway results in a variety of complement-mediated disorders such as, and not limited to, autoimmune hemolytic anemias (AIHA), Behcet's disease, Bullous Pemphigus (BP), immune thrombocytopenia purpura (ITP) etc. Therefore, inhibition of excessive or uncontrolled activation of the classical pathway can provide clinical benefit to patients with such disorders.

Antibodies are highly attractive pharmaceuticals as they are stable in plasma, highly specific for their target, and generally exhibit good pharmacokinetic profiles. However, due to their large molecular size, the dosage of therapeutic antibodies is usually high. In the case of targets that exist in high abundance, the required therapeutic dose of antibodies is even higher. As a result, methods that improve antibody pharmacokinetics, pharmacodynamics, and antigen binding properties are attractive ways to reduce the dosage and high production costs associated with therapeutic antibodies.

Several prior reports have described anti-C1s antibodies. For example, Matsumoto et. al. (1986) (Non Patent Literature 8) described three antibodies which bound to distinct epitopes on C1s. One clone exhibited preferential binding for the active form of C1s, whereas the other two bound to both proenzyme and active C1s. Of these two clones, only one was able to inhibit C2 and C4 cleavage by C1s. Patent Literature 1 described an antibody which inhibited C1s mediated cleavage of C4 but not C2. Additionally, Patent Literature 2 described several antibodies which bound to a conformational epitope on C1s with selectivity to active C1s compared to its proenzyme form. Patent Literature 3 described two clones of anti-C1s antibodies which were able to block C4 cleavage.

The affinity of an antibody for its antigen determines how efficiently the antibody can neutralize its target. Various affinity maturation methods (Non Patent Literature 9) are used to increase antibody affinity to reduce the required dose for therapeutic effect. However, the limitation is that one antibody molecule typically has two binding sites, and thus can only neutralize two targets (one antigen per binding site) after administration. Even if the antibody can bind the target with infinite affinity by covalent interaction, the maximum number of targets neutralized by the antibody remains capped at two.

It has been reported that antibodies that bind to an antigen in a pH-dependent manner (herein below also referred to as "pH-dependent antibody" or "pH-dependent-binding antibody") enables a single antibody molecule to neutralize multiple antigen molecules (Non Patent Literature 10, Patent Literature 4). The pH-dependent antibody binds strongly to its antigen at neutral pH conditions in the plasma, but dissociates from the antigen under the acidic pH condition within the endosome of a cell. Once dissociated from the antigen, the antibody is recycled back to the plasma by FcRn receptors whereas the dissociated antigens are degraded within the lysosome of the cell. The recycled antibody is then free to bind to and neutralize antigen molecules again and this process continues to be repeated as long as the antibody remains in circulation.

CITATION LIST

Patent Literature

PTL 1 WO2014/071206
PTL 2 WO2014/066744
PTL 3 WO2014/186599
PTL 4 WO2009/125825

Non Patent Literature

NPL 1 Wang et. al. Mol Cell. 2016 Jul. 7; 63(1):135-45
NPL 2 Mortensen et. al. Proc Natl Acad Sci USA. 2017 Jan. 31; 114(5):986-991
NPL 3 Arlaud et. al. Biochim Biophys Acta. 1980 Nov. 6; 616(1):105-15
NPL 4 Rivas et. al. Biochemistry. 1992 Dec. 1; 31(47): 11707-12
NPL 5 Rossi et. al. Methods Mol Biol. 2014; 1100:43-60
NPL 6 Petillot et. al. FEBS Lett. 1995 Jan. 30; 358(3):323-8
NPL 7 Shi et. al. Blood. 2014 Jun. 26; 123(26):4015-22
NPL 8 Matsumoto et. al. J Immunol. 1986 Nov. 1; 137(9): 2907-12
NPL 9 Kim et. al. Methods Mol Biol. 2014; 1131:407-20
NPL 10 Igawa et. al. Nat Biotechnol. 2010 November; 28(11):1203-7

SUMMARY OF INVENTION

Technical Problem

The invention provides anti-C1s antibodies and methods of using the same.

Solution to Problem

In addition to binding to C1s in a pH-dependent manner, the effect of calcium on a pH-dependent antibody's affinity to C1s may be another important property. C1s forms dimers at high calcium concentrations but dissociates into monomers at low calcium concentrations. When C1s is in a dimeric state, a bivalent antibody is able to form immune complexes by crosslinking multiple C1s molecules. This allows the antibody to bind to C1s molecules within the complex by both affinity and avidity interactions, thus increasing the apparent affinity of the antibody. In contrast, when C1s is in a monomeric state, the antibody only binds by affinity interaction to C1s. This means that the pH-dependent C1s antibody can form immune complex with dimeric C1s in the plasma, but once within the acidic endosome, C1s will dissociate into monomers. This leads to the disassembly of the immune complex which then enhances the pH-dependent dissociation of the antibody from the antigen.

In some embodiments, an isolated anti-C1s antibody of the present invention is an antibody having the C1s-binding activity which varies depending on an ion concentration. In some embodiments, an isolated anti-C1s antibody binds to C1s with a higher affinity at neutral pH than at acidic pH. In some embodiments, anti-C1s antibody binds to C1s with a higher affinity under a high calcium concentration condition than under a low calcium concentration condition. In some embodiments, an isolated anti-C1s antibody binds to C1s with a higher affinity both at neutral pH and under a high calcium concentration condition than both at acidic pH and under a low calcium concentration.

In some embodiments, in an isolated anti-C1s antibody of the present invention, the ratio of the KD value for its C1s-binding activity at acidic pH to the KD value for the C1s-binding activity at neutral pH (KD(acidic pH)/KD (neutral pH)) is 2 or more when measured at a high calcium concentration at both neutral and acidic pH. In some embodiments, in an isolated anti-C1s antibody of the present invention, the ratio of the KD value for its C1s-binding activity at acidic pH to the KD value for the C1s-binding activity at neutral pH (KD(acidic pH)/KD(neutral pH)) is 2 or more when measured at a low calcium concentration at both neutral and acidic pH, wherein the anti-C1s antibody binds to the dimeric state of C1s. In some embodiments, in an isolated anti-C1s antibody of the present invention, the ratio of the koff value for its C1s-binding activity at acidic pH to the koff value for the C1s-binding activity at neutral pH (koff(acidic pH)/koff(neutral pH)) is 2 or more when measured at a high calcium concentration at both neutral and acidic pH. In some embodiments, in an isolated anti-C1s antibody of the present invention, the ratio of the koff value for its C1s-binding activity at acidic pH to the koff value for the C1s-binding activity at neutral pH (koff(acidic pH)/koff (neutral pH)) is 2 or more when measured at a low calcium concentration at both neutral and acidic pH, wherein the anti-C1s antibody binds to the dimeric state of C1s. In some embodiments, in an isolated anti-C1s antibody of the present invention, the ratio of the KD value for its C1s-binding activity at acidic pH to the KD value for the C1s-binding activity at neutral pH (KD(acidic pH)/KD(neutral pH)) is 5 or more when measured at a high calcium concentration at neutral pH and under low calcium concentration at acidic pH.

In some embodiments, an isolated anti-C1s antibody of the present invention comprises a histidine residue at one or more of the following Kabat numbering system positions;
Heavy chain: H26, H27, H28, H29, H30, H31, H32, H33, H34, H35, H50, H51, H52, H52a, H53, H54, H55, H57, H58, H59, H60, H61, H62, H63, H64, H65, H93, H94, H95, H96, H97, H98, H99, H100, H100a, H101, and H102; and
Light chain: L24, L25, L26, L27, L27a, L28, L29, L30, L31, L32, L33, L50, L51, L52, L53, L54, L55, L56 L91, L92, L93, L94, L95, L95a, L96, and L97.

In some embodiments, an isolated anti-C1s antibody of the present invention comprises a histidine residue at one or more of the following Kabat numbering system positions;
Heavy chain: H51, H65, and H99; and
Light chain: L92, L94, L95 and L96.

In some embodiments, an isolated anti-C1s antibody of the present invention comprises of one, two, three, four, or five histidines of the following Kabat numbering system positions;
Heavy chain: H51, H65, and H99; and
Light chain: L92, L94, L95 and L96.

In some embodiments, an isolated anti-C1s antibody of the present invention comprises a histidine residue at one or more of the following positions and one or more CDR or one or more FR amino acid positions, by Kabat numbering system;
Heavy chain: H51, H65, and H99; and
Light chain: L92, L94, L95 and L96.

In some embodiments, an isolated anti-C1s antibody of the present invention comprises a histidine residue at the following positions by Kabat numbering system;
1) L92 and L94
2) L92 and L95
3) L94 and L95
4) L92, L94 and L95
5) H65 and L92
6) H65 and L94
7) H65 and L95
8) H65, L92 and L94
9) H65, L92 and L95
10) H65, L94 and L95
11) H65, L92, L94 and L95
12) H99 and L92
13) H99 and L94
14) H99 and L95
15) H99, L92 and L94
16) H99, L92 and L95
17) H99, L94 and L95
18) H99, L92, L94 and L95
19) H65 and H99
20) H65, H99 and L92
21) H65, H99 and L94
22) H65, H99 and L95
23) H65, H99, L92 and L94
24) H65, H99, L92 and L95
25) H65, H99, L94 and L95
26) H65, H99, L92, L94 and L95, or
27) H27, H99 and L95.

In some embodiments, anti-C1s antibody of the present invention comprises at least one histidine which is substituted at one or more of the following Kabat numbering system positions;
Heavy chain: H26, H27, H28, H29, H30, H31, H32, H33, H34, H35, H50, H51, H52, H52a, H53, H54, H55, H57, H58, H59, H60, H61, H62, H63, H64, H65, H93, H94, H95, H96, H97, H98, H99, H100, H100a, H101, and H102; and
Light chain: L24, L25, L26, L27, L27a, L28, L29, L30, L31, L32, L33, L50, L51, L52, L53, L54, L55, L56 L91, L92, L93, L94, L95, L95a, L96, and L97.

In some embodiments, anti-C1s antibody of the present invention comprises at least one histidine which is substituted at one or more of the following Kabat numbering system positions;
Heavy chain: H51, H65, and H99; and
Light chain: L92, L94, L95 and L96.

In some embodiments, an isolated anti-C1s antibody of the present invention comprises one, two, three, four, or five histidines substituted of the following Kabat numbering system positions;
Heavy chain: H51, H65, and H99; and
Light chain: L92, L94, L95 and L96.

In some embodiments, an isolated anti-C1s antibody of the present invention comprises at least one histidine which is substituted residue at one of more of the following positions and one or more CDR or one or more FR amino acid position, by Kabat numbering system;
Heavy chain: H51, H65, and H99; and
Light chain: L92, L94, L95 and L96.

In some embodiments, an isolated anti-C1s antibody of the present invention comprises at least one histidine which is substituted residue at the following positions by Kabat numbering system;
1) L92 and L94
2) L92 and L95
3) L94 and L95
4) L92, L94 and L95
5) H65 and L92
6) H65 and L94
7) H65 and L95
8) H65, L92 and L94
9) H65, L92 and L95
10) H65, L94 and L95
11) H65, L92, L94 and L95
12) H99 and L92
13) H99 and L94
14) H99 and L95
15) H99, L92 and L94
16) H99, L92 and L95
17) H99, L94 and L95
18) H99, L92, L94 and L95
19) H65 and H99
20) H65, H99 and L92
21) H65, H99 and L94
22) H65, H99 and L95
23) H65, H99, L92 and L94
24) H65, H99, L92 and L95
25) H65, H99, L94 and L95
26) H65, H99, L92, L94 and L95, or
27) H27, H99 and L95.

In some embodiments, an isolated anti-C1s antibody of the present invention competes at neutral pH condition for binding to C1s with an antibody selected from the group consisting of:
(a) an antibody comprising the HVR-H1 sequence of SEQ ID NO: 23, the HVR-H2 sequence of SEQ ID NO: 24, the HVR-H3 sequence of SEQ ID NO: 25, the HVR-L1 sequence of SEQ ID NO: 26, the HVR-L2 sequence of SEQ ID NO: 27, and the HVR-L3 sequence of SEQ ID NO: 28,
(b) an antibody comprising the HVR-H1 sequence of SEQ ID NO: 29, the HVR-H2 sequence of SEQ ID NO: 30, the HVR-H3 sequence of SEQ ID NO: 31, the HVR-L1 sequence of SEQ ID NO: 32, the HVR-L2 sequence of SEQ ID NO: 33, and the HVR-L3 sequence of SEQ ID NO: 34,
(c) Human monoclonal anti-C1s antibody M241 or Human monoclonal anti-C1s antibody M81,
(d) an antibody comprising the HVR-H1 sequence of SEQ ID NO: 56, the HVR-H2 sequence of SEQ ID NO: 57, the HVR-H3 sequence of SEQ ID NO: 58, the HVR-L1 sequence of SEQ ID NO: 71, the HVR-L2 sequence of SEQ ID NO: 72, and the HVR-L3 sequence of SEQ ID NO: 73,
(e) an antibody comprising the HVR-H1 sequence of SEQ ID NO: 59, the HVR-H2 sequence of SEQ ID NO: 60, the HVR-H3 sequence of SEQ ID NO: 61, the HVR-L1 sequence of SEQ ID NO: 74, the HVR-L2 sequence of SEQ ID NO: 75, and the HVR-L3 sequence of SEQ ID NO: 76,
(f) an antibody comprising the HVR-H1 sequence of SEQ ID NO: 62, the HVR-H2 sequence of SEQ ID NO: 63, the HVR-H3 sequence of SEQ ID NO: 64, the HVR-L1 sequence of SEQ ID NO: 77, the HVR-L2 sequence of SEQ ID NO: 78, and the HVR-L3 sequence of SEQ ID NO: 79,
(g) an antibody comprising the HVR-H1 sequence of SEQ ID NO: 65, the HVR-H2 sequence of SEQ ID NO: 66, the HVR-H3 sequence of SEQ ID NO: 67, the HVR-L1 sequence of SEQ ID NO: 80, the HVR-L2 sequence of SEQ ID NO: 81, and the HVR-L3 sequence of SEQ ID NO: 82, and (h) an antibody comprising the HVR-H1 sequence of SEQ ID NO: 68, the HVR-H2 sequence of SEQ ID NO: 69, the HVR-H3 sequence of SEQ ID NO: 70, the HVR-L1 sequence of SEQ ID NO: 83, the HVR-L2 sequence of SEQ ID NO: 84, and the HVR-L3 sequence of SEQ ID NO: 85, wherein the antibody binds to C1s with a higher affinity at neutral pH than at acidic pH as described in (i) or (ii) below:

(i) when measured at a high calcium concentration at both neutral and acidic pH, the ratio of the KD value for C1s-binding activity at acidic pH to the KD value for C1s-binding activity at neutral pH (KD(acidic pH)/KD (neutral pH)) is 2 or more, (ii) when measured at a high calcium concentration at both neutral and acidic pH, the ratio of the koff value for C1s-binding activity at acidic pH to the koff value for C1s-binding activity at neutral pH (koff(acidic pH)/koff(neutral pH)) is 2 or more.

In some embodiments, an isolated anti-C1s antibody of the present invention competes for binding to C1s with an antibody selected from the group consisting of:

(a) an antibody comprising the HVR-H1 sequence of SEQ ID NO: 56, the HVR-H2 sequence of SEQ ID NO: 57, the HVR-H3 sequence of SEQ ID NO: 58, the HVR-L1 sequence of SEQ ID NO: 71, the HVR-L2 sequence of SEQ ID NO: 72, and the HVR-L3 sequence of SEQ ID NO: 73, (b) an antibody comprising the HVR-H1 sequence of SEQ ID NO: 59, the HVR-H2 sequence of SEQ ID NO: 60, the HVR-H3 sequence of SEQ ID NO: 61, the HVR-L1 sequence of SEQ ID NO: 74, the HVR-L2 sequence of SEQ ID NO: 75, and the HVR-L3 sequence of SEQ ID NO: 76, (c) an antibody comprising the HVR-H1 sequence of SEQ ID NO: 62, the HVR-H2 sequence of SEQ ID NO: 63, the HVR-H3 sequence of SEQ ID NO: 64, the HVR-L1 sequence of SEQ ID NO: 77, the HVR-L2 sequence of SEQ ID NO: 78, and the HVR-L3 sequence of SEQ ID NO: 79, (d) an antibody comprising the HVR-H1 sequence of SEQ ID NO: 65, the HVR-H2 sequence of SEQ ID NO: 66, the HVR-H3 sequence of SEQ ID NO: 67, the HVR-L1 sequence of SEQ ID NO: 80, the HVR-L2 sequence of SEQ ID NO: 81, and the HVR-L3 sequence of SEQ ID NO: 82, and (e) an antibody comprising the HVR-H1 sequence of SEQ ID NO: 68, the HVR-H2 sequence of SEQ ID NO: 69, the HVR-H3 sequence of SEQ ID NO: 70, the HVR-L1 sequence of SEQ ID NO: 83, the HVR-L2 sequence of SEQ ID NO: 84, and the HVR-L3 sequence of SEQ ID NO: 85.

In some embodiments, the present disclosure provides an isolated anti-C1s antibody that specifically binds to an epitope within a region encompassing domains IV and V of complement component Is (C1s). In some cases, the antibody inhibits binding of C1s to complement component 4 (C4). In some cases, the epitope bound by an isolated anti-C1s antibody of the present disclosure is a conformational epitope. In some embodiments, the above-described epitope of C1s is an epitope of human C1s.

In some embodiments, anti-C1s antibody of the present invention comprises a VH sequence of SEQ ID NO: 35, or 36 and/or a VL sequence of SEQ ID NO: 37, or 38, wherein at least one amino acid is substituted with a histidine at one or more of the following Kabat numbering system positions;
Heavy chain: H51, H65, and H99; and
Light chain: L92, L94, L95 and L96.

In some embodiments, anti-C1s antibody of the present invention comprises at least one amino acid at the variable region is substituted with an amino acid selected from the group consisting of D, E, K, R and Q, such that non-specific binding activity at acidic pH of the antibody will be reduced.

In some embodiments, anti-C1s antibody of the present invention comprises at least one amino acid at the variable region is substituted with an amino acid selected from the group consisting of D, E, K, R and Q, such that the ratio of the KD value for C1s-binding activity at acidic pH to the C1s-binding activity at neutral pH (KD(acidic pH)/KD (neutral pH)) will be increased.

In some embodiments, an isolated anti-C1s antibody of the present invention comprises (a) HVR-H1 comprising the amino acid sequence of SEQ ID NO: 39, (b) HVR-H2 comprising the amino acid sequence of SEQ ID NO: 40, and (c) HVR-H3 comprising the amino acid sequence of SEQ ID NO: 41, wherein the antibody comprises human-derived or primate-derived framework regions. In some embodiments, an isolated anti-C1s antibody of the present invention comprises (a) HVR-L1 comprising the amino acid sequence of SEQ ID NO: 42 or 45; (b) HVR-L2 comprising the amino acid sequence of SEQ ID NO: 43; and (c) HVR-L3 comprising the amino acid sequence of SEQ ID NO: 44, wherein the antibody comprises human-derived or primate-derived framework regions.

In some embodiments, anti-C1s antibody of the present invention comprises (a) a VH sequence having at least 95% sequence identity to the amino acid sequence of SEQ ID NO: 19, 17, or 22; (b) a VL sequence having at least 95% sequence identity to the amino acid sequence of SEQ ID NO: 20, 18, or 21; or (c) a VH sequence of (a) and a VL sequence of (b). In some embodiments, an anti-C1s antibody of the present invention comprises a VH sequence of SEQ ID NO: 19, 17, or 22. In some embodiments, an anti-C1s antibody of the present invention comprises a VL sequence of SEQ ID NO: 20, 18, or 21. In further embodiments, an anti-C1s antibody of the present invention comprises a VH sequence of SEQ ID NO: 19, 17, or 22 and a VL sequence of SEQ ID NO: 20, 18, or 21. In further embodiments, an anti-C1s antibody of the present invention comprises a VH sequence of SEQ ID NO: 19 and a VL sequence of SEQ ID NO: 20. In further embodiments, an anti-C1s antibody of the present invention comprises a VH sequence of SEQ ID NO: 19 and a VL sequence of SEQ ID NO: 21. In further embodiments, an anti-C1s antibody of the present invention comprises a VH sequence of SEQ ID NO: 22 and a VL sequence of SEQ ID NO: 21.

In some embodiments, an isolated anti-C1s antibody of the present invention is a monoclonal antibody. In some embodiments, an isolated anti-C1s antibody of the present invention is a human, humanized, or chimeric antibody. In further embodiments, an isolated anti-C1s antibody of the present invention is a full length IgG1, IgG2, IgG3 or IgG4 antibody. In further embodiments, an isolated anti-C1s antibody of the present invention is an antibody fragment that binds to C1s. In some specific embodiments, an isolated anti-C1s antibody of the present invention is a human IgG1 or humanized IgG1.

The invention also provides isolated nucleic acids encoding an anti-C1s antibody of the present invention. The invention also provides host cells comprising a nucleic acid of the present invention. The invention also provides a method of producing an antibody comprising culturing a host cell of the present invention so that the antibody is produced.

The invention also provides a pharmaceutical formulation comprising the antibody of the present invention and a pharmaceutically acceptable carrier.

Anti-C1s antibodies of the present invention may be for use as a medicament. Anti-C1s antibodies of the present invention may be for use in treating a complement-mediated disease or disorder. Anti-C1s antibodies of the present invention may be for use in enhancing the clearance of (or removing) C1s from plasma. Anti-C1s antibodies of the present invention may be for use in enhancing the clearance of (or removing) the complex of C1q, C1r and C1s from plasma. In some embodiments, anti-C1s antibodies of the present invention may be for use in inhibits cleavage of complement component C4, where the antibody does not inhibit cleavage of complement component C2. In some cases, the antibody inhibits a component of the classical complement pathway; in some cases, the classical complement pathway component is C1s.

Anti-C1s antibodies of the present invention may be used in the manufacture of a medicament. In some embodiments, the medicament is for treatment of a complement-mediated disease or disorder. In some embodiments, the medicament is for enhancing the clearance of (or removing) C1s from plasma. In some embodiments, the medicament is for enhancing the clearance of (or removing) the complex of C1q, C1r and C1s from plasma. The medicament is for inhibiting the cleavage of complement component C4, where the antibody does not inhibit cleavage of complement component C2. In some cases, the medicament inhibits a component of the classical complement pathway; in some cases, the classical complement pathway component is C1s.

The invention also provides a method of treating an individual having a complement-mediated disease or disorder. In some embodiments, the method comprises administering to the individual an effective amount of an anti-C1s antibody of the present invention. The invention also provides a method of enhancing the clearance of (or removing) C1s from plasma in an individual. In some embodiments, the method comprises administering to the individual an effective amount of an anti-CIS antibody of the present invention to enhance the clearance of (or remove) C1s from plasma. The invention also provides a method of enhancing the clearance of (or removing) the complex of C1q, C1r and C1s from plasma in an individual. In some embodiments, the method comprises administering to the individual an effective amount of an anti-C1s antibody of the present invention to enhance the clearance of (or remove) the complex of C1q, C1r and C1s from plasma. The invention also provides methods of inhibits cleavage of complement component C4, where the antibody does not inhibit cleavage of complement component C2. In some cases, the antibody inhibits a component of the classical complement pathway; in some cases, the classical complement pathway component is C1s.

More specifically, the present invention provides the following:

[1] An isolated antibody that binds to C1s, wherein the antibody binds to C1s with a higher affinity at neutral pH than at acidic pH as described in (i) or (ii) below:
   (i) when measured at a high calcium concentration at both neutral and acidic pH, the ratio of the KD value for C1s-binding activity at acidic pH to the KD value for C1s-binding activity at neutral pH (KD(acidic pH)/KD(neutral pH)) is 2 or more,
   (ii) when measured at a high calcium concentration at both neutral and acidic pH, the ratio of the koff value for C1s-binding activity at acidic pH to the koff value for C1s-binding activity at neutral pH (koff(acidic pH)/koff(neutral pH)) is 2 or more.

[2] The antibody of [1], wherein the antibody comprises a histidine residue at one or more of the following Kabat numbering system positions:
Heavy chain: H51, H65 and H99; and
Light chain: L92, L94, L95 and L96.

[3] The antibody of [1] or [2], wherein at least one amino acid is substituted with a histidine at one or more of the following Kabat numbering system positions:
Heavy chain: H51, H65 and H99; and
Light chain: L92, L94, L95 and L96.

[4] The antibody of any one of [1] to [3], wherein the antibody competes at a neutral pH condition for binding to C1s with an antibody selected from the group consisting of:
   (a) an antibody comprising the HVR-H1 sequence of SEQ ID NO: 23, the HVR-H2 sequence of SEQ ID NO: 24 the HVR-H3 sequence of SEQ ID NO: 25, the HVR-L1 sequence of SEQ ID NO: 26, the HVR-L2 sequence of SEQ ID NO: 27, and the HVR-L3 sequence of SEQ ID NO: 28,
   (b) an antibody comprising the HVR-H1 sequence of SEQ ID NO: 29, the HVR-H2 sequence of SEQ ID NO: 30, the HVR-H3 sequence of SEQ ID NO: 31, the HVR-L1 sequence of SEQ ID NO: 32, the HVR-L2 sequence of SEQ ID NO: 33, and the HVR-L3 sequence of SEQ ID NO: 34,
   (c) Human monoclonal anti-C1s antibody M241,
   (d) an antibody comprising the HVR-H1 sequence of SEQ ID NO: 56, the HVR-H2 sequence of SEQ ID NO: 57, the HVR-H3 sequence of SEQ ID NO: 58, the HVR-L1 sequence of SEQ ID NO: 71, the HVR-L2 sequence of SEQ ID NO: 72, and the HVR-L3 sequence of SEQ ID NO: 73,
   (e) an antibody comprising the HVR-H1 sequence of SEQ ID NO: 59, the HVR-H2 sequence of SEQ ID NO: 60, the HVR-H3 sequence of SEQ ID NO: 61, the HVR-L1 sequence of SEQ ID NO: 74, the HVR-L2 sequence of SEQ ID NO: 75, and the HVR-L3 sequence of SEQ ID NO: 76,
   (f) an antibody comprising the HVR-H1 sequence of SEQ ID NO: 62, the HVR-H2 sequence of SEQ ID NO: 63, the HVR-H3 sequence of SEQ ID NO: 64, the HVR-L1 sequence of SEQ ID NO: 77, the HVR-L2 sequence of SEQ ID NO: 78, and the HVR-L3 sequence of SEQ ID NO: 79,
   (g) an antibody comprising the HVR-H1 sequence of SEQ ID NO: 65, the HVR-H2 sequence of SEQ ID NO: 66, the HVR-H3 sequence of SEQ ID NO: 67, the HVR-L1 sequence of SEQ ID NO: 80, the HVR-L2 sequence of SEQ ID NO: 81, and the HVR-L3 sequence of SEQ ID NO: 82, and
   (h) an antibody comprising the HVR-H1 sequence of SEQ ID NO: 68, the HVR-H2 sequence of SEQ ID NO: 69, the HVR-H3 sequence of SEQ ID NO: 70, the HVR-L1 sequence of SEQ ID NO: 83, the HVR-L2 sequence of SEQ ID NO: 84, and the HVR-L3 sequence of SEQ ID NO: 85.

[5] The antibody of any one of [1] to [4], wherein the antibody comprises a VH sequence of SEQ ID NO: 35 or 36 and/or a VL sequence of SEQ ID NO: 37 or 38 wherein at least one amino acid at the variable region is substituted with a histidine at one or more of the following Kabat numbering system positions:
Heavy chain: H51, H65 and H99; and
Light chain: L92, L94, L95 and L96.

[6] The antibody of any one of [1] to [5], wherein additionally at least one amino acid at the variable region is substituted with an amino acid selected from the group consisting of D, E, K, R and Q, such that non-specific binding activity at acidic pH of the antibody will be reduced, or the ratio of the KD value for C1s-binding activity at acidic pH to the KD value for C1s-binding activity at neutral pH (KD(acidic pH)/KD(neutral pH)) will be increased.

[7] An isolated antibody that binds to C1s, wherein the antibody comprises (a) HVR-H1 comprising the amino acid sequence of SEQ ID NO: 39, (b) HVR-H2 comprising the amino acid sequence of SEQ ID NO: 40, and (c) HVR-H3 comprising the amino acid sequence of SEQ ID NO: 41, wherein the antibody comprises human-derived or primate-derived framework regions.

[8] An isolated antibody that binds to C1s, wherein the antibody comprises (a) HVR-L1 comprising the amino acid sequence of SEQ ID NO: 42; (b) HVR-L2 comprising the amino acid sequence of SEQ ID NO: 43; and (c) HVR-L3 comprising the amino acid sequence of SEQ ID NO: 44, wherein the antibody comprises human-derived or primate-derived framework regions.

[9] The antibody of any one of [1] to [8], comprising (a) a VH sequence having at least 95% sequence identity to the amino acid sequence of SEQ ID NO: 19, 17, or 22; (b) a VL sequence having at least 95% sequence identity to the amino acid sequence of SEQ ID NO: 20, 18, or 21; or (c) the VH sequence of (a) and the VL sequence of (b).

[10] The antibody of [9], comprising a VH sequence of SEQ ID NO: 19, 17, or 22.

[11] The antibody of [9], comprising a VL sequence of SEQ ID NO: 20, 18, or 21.

[12] An antibody comprising a VH sequence of SEQ ID NO: 19 and a VL sequence of SEQ ID NO: 20.

[13] A pharmaceutical formulation comprising the antibody of any one of [1] to and a pharmaceutically acceptable carrier.

[14] A method of treating an individual having a complement-mediated disease or disorder comprising administering to the individual an effective amount of the antibody of any one of [1] to [12].

Furthermore, the present invention provides the following:

[15] A method of removing C1s from plasma, the method comprising:
(a) identifying an individual in need of having C1s removed from the individual's plasma;
(b) providing an antibody that binds to C1s through the C1s-binding domain of the antibody and has a KD(pH5.8)/KD(pH7.4) value, defined as the ratio of KD for C1s at pH 5.8 and KD for C1s at pH 7.4, of 2 to 10,000, when KD is determined using a surface plasmon resonance technique, wherein the antibody binds to C1s in plasma in vivo and dissociates from the bound C1s under conditions present in an endosome in vivo, and wherein the antibody is a human IgG or a humanized IgG; and
(c) administering the antibody to the individual.

[16] A method of removing C1s from plasma in a subject, the method comprising:
(a) identifying a first antibody that binds to C1s through the C1s-binding domain of the first antibody;
(b) identifying a second antibody that:
(1) binds to C1s through the C1s-binding domain of the second antibody,
(2) is identical in amino acid sequence to the first antibody except having at least one amino acid of a variable region of the first antibody substituted with histidine and/or at least one histidine inserted into a variable region of the first antibody,
(3) has a KD(pH5.8)/KD(pH7.4) value that is higher than the first antibody's KD(pH5.8)/KD(pH7.4) value, and is between 2 and 10,000, wherein KD(pH5.8)/KD(pH7.4) is defined as the ratio of KD for C1s at pH 5.8 and KD for C1s at pH 7.4 when KD is determined using a surface plasmon resonance technique,
(4) binds to C1s in plasma in vivo,
(5) dissociates from the bound C1s under conditions present in an endosome in vivo, and
(6) is a human IgG or a humanized IgG;
(c) identifying a subject in need of having his or her plasma level of C1s reduced; and
(d) administering the second antibody to the subject so that the plasma level of C1s in the subject is reduced.

[17] A method of removing C1s from plasma in a subject, the method comprising:
(a) identifying a first antibody that:
(1) binds to C1s through the C1s-binding domain of the first antibody,
(2) is identical in amino acid sequence to a second antibody that binds to C1s through the antigen-binding domain of the second antibody, except that at least one variable region of the first antibody has at least one more histidine residue than does the corresponding variable region of the second antibody,
(3) has a KD(pH5.8)/KD(pH7.4) value that is higher than the second antibody's KD(pH5.8)/KD(pH7.4) value, and is between 2 and 10,000, wherein KD(pH5.8)/KD(pH7.4) is defined as the ratio of KD for C1s at pH 5.8 and KD for C1s at pH 7.4 when KD is determined using a surface plasmon resonance technique,
(4) binds to C1s in plasma in vivo,
(5) dissociates from the bound C1s under conditions present in an endosome in vivo, and
(6) is a human IgG or a humanized IgG;
(b) identifying a subject in need of having his or her plasma level of C1s reduced; and
(c) administering the first antibody at least once to the subject so that the plasma level of C1s in the subject is reduced.

[18] The method of any one of to [17], wherein the KD is determined using a surface plasmon resonance technique in which the antibody is immobilized, the antigen serves as analyte, and the following conditions are used: 10 mM MES buffer, 0.05% polyoxyethylenesorbitan monolaurate, and 150 mM NaCl at 37 degrees Celsius (C).

[19] An isolated antibody that binds to a C1 complex consisting of C1q, C1r and C1s, wherein the antibody binds to the C1 complex with a higher affinity at neutral pH than at acidic pH as described in (i) or (ii) below:
(i) when measured at a high calcium concentration at both neutral and acidic pH, the ratio of the KD value for C1 complex-binding activity at acidic pH to the KD value for C1 complex-binding activity at neutral pH (KD(acidic pH)/KD(neutral pH)) is 2, 3, 5, 10, 15, 20, 25, 30, 35, 40, 45, 50, 55, 60, 65, 70, 75, 80, 85, 90, 95, 100, 200, 400, 1000, 10000, or more, (ii) when measured at a high calcium concentration at neutral pH and at a low calcium concentration at acidic pH, the ratio of the KD value for C1 complex-binding activity at acidic pH to the KD value for C1 complex-binding activity at neutral pH (KD(acidic pH)/KD(neutral pH)) is 2, 3, 5, 10, 15, 20, 25, 30, 35, 40, 45, 50, 55, 60, 65, 70, 75, 80, 85, 90, 95, 100, 200, 400, 1000, 10000, or more.

[20] An isolated antibody that binds to C1s, wherein the antibody binds to C1s with a higher affinity at neutral pH than at acidic pH, wherein the ratio of the KD value for its C1s-binding activity at acidic pH to the KD value for the C1s-binding activity at neutral pH (KD(acidic pH)/KD(neutral pH)) is 2, 3, 5, 10, 15, 20, 25, 30, 35, 40, 45, 50, 55, 60, 65, 70, 75, 80, 85, 90, 95, 100, 200, 400, 1000, 10000, or more when measured at a low calcium concentration at both neutral and acidic pH, wherein the anti-C1s antibody binds to the dimeric state of C1s.

BRIEF DESCRIPTION OF DRAWINGS

FIG. 1 illustrates the correlation between Sweeping Index Improvement and ratio of KD (5.8+)/KD (7.4+) for all antibodies listed in Table 10, excluding antibody IPN92H0286/IPN93L0205-SG136.

FIG. 2 illustrates the correlation between Sweeping Index Improvement and ratio of koff (5.8+ of 775+)/koff (7.4+) for all antibodies listed in Table 10, excluding antibody IPN92H0286/IPN93L0205-SG136.

DESCRIPTION OF EMBODIMENTS

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3d edition (2001) Cold Spring Harbor Laboratory Press, Cold Spring Harbor, N.Y.; Current Protocols in Molecular Biology (F. M. Ausubel, et al. eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993).

I. DEFINITIONS

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. All references cited herein, including patent applications and publications, are incorporated by reference in their entirety.

For purposes of interpreting this specification, the following definitions will apply and whenever appropriate, terms used in the singular will also include the plural and vice versa. It is to be understood that the terminology used herein is for the purpose of describing particular embodiments only, and is not intended to be limiting. In the event that any definition set forth below conflicts with any document incorporated herein by reference, the definition set forth below shall control.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd or KD). Affinity can be measured by common methods known in the art, including those described herein. Specific illustrative and exemplary embodiments for measuring binding affinity are described in the following. The term "binding activity" refers to the strength of the sum total of noncovalent interactions between a single or more binding sites of a molecule (e.g., an antibody) and its binding partner (e.g., an antigen). Herein, binding activity is not strictly limited to an activity which reflects a 1:1 interaction between members of a binding pair (e.g., antibody and antigen). When members of a binding pair can bind to each other in the manner of both monovalent and multivalent binding, binding activity is the strength of the sum total of these bindings. The binding activity of a molecule X for its partner Y can generally be represented by the dissociation constant (KD). Alternatively, the association and dissociation rates (Kon and Koff) may be used for the assessment of binding. Binding activity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-C1s antibody" and "an antibody that binds to C1s" refer to an antibody that is capable of binding C1s with sufficient affinity such that the antibody is useful as a diagnostic and/or therapeutic agent in targeting C1s. In one embodiment, the extent of binding of an anti-C1s antibody to an unrelated, non-C1s protein is less than about 10% of the binding of the antibody to C1s as measured, e.g., by a radioimmunoassay (RIA). In certain embodiments, an antibody that binds to C1s has a dissociation constant (Kd) of 1 micro M or less, 100 nM or less, 10 nM or less, 1 nM or less, 0.1 nM or less, 0.01 nM or less, or 0.001 nM or less (e.g. 10-8 M or less, e.g. from 10-8 M to 10-13 M, e.g., from 10-9 M to 10-13 M). In certain embodiments, an anti-C1s antibody binds to an epitope of C1s that is conserved among C1s from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called alpha, delta, epsilon, gamma, and mu, respectively.

The term "cytotoxic agent" as used herein refers to a substance that inhibits or prevents a cellular function and/or causes cell death or destruction. Cytotoxic agents include, but are not limited to, radioactive isotopes (e.g., 211At, 131I, 125I, 90Y, 186Re, 188Re, 153Sm, 212Bi, 32P, 212Pb and radioactive isotopes of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" includes any determinant capable of being bound by an antibody. An epitope is a region of an antigen that is bound by an antibody that targets that antigen, and includes specific amino acids that directly contact the antibody. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, M D, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:
 (a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));
 (b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));
 (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
 (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-C1s antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies composing the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa and lambda, based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "C1s," as used herein, refers to any native C1s from any vertebrate source, including mammals such as primates (e.g. humans) and rodents (e.g., mice and rats), unless otherwise indicated. The term encompasses "full-length" unprocessed C1s as well as any form of C1s that results from processing in the cell. The term also encompasses naturally occurring variants of C1s, e.g., splice variants or allelic variants. The amino acid sequence of an exemplary human C1s is shown in SEQ ID NO: 1. The amino acid sequences of an exemplary cynomolgus monkey, and rat C1s are shown in SEQ ID Nos: 3 and 2, respectively.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. COMPOSITIONS AND METHODS

In one aspect, the invention is based, in part, on anti-C1s antibodies and uses thereof. In certain embodiments, antibodies that bind to C1s are provided. Antibodies of the invention are useful, e.g., for the diagnosis or treatment of complement-mediated disease or disorder.

A. Exemplary Anti-C1s Antibodies

In one aspect, the invention provides isolated antibodies that bind to C1s. In one aspect, the invention provides isolated antibodies that bind to C1s, whose binding activity varies depending on the ion concentration. In certain embodiments, the binding activity of anti-C1s antibody varies depending on pH, i.e., hydrogen ion (proton) concentration. In certain embodiments, the binding activity of anti-C1s antibody varies depending on the calcium concentration. In certain embodiment, the binding activity of anti-C1s antibody varies depending on both pH and the calcium concentration. Such antibodies are expected to be especially superior as pharmaceuticals, because the dose and frequency of administration in patients can be reduced and as a result the total dosage can be reduced.

In one aspect, in an isolated anti-C1s antibody of the present invention, the ratio of the KD value for its C1s-binding activity at acidic pH to the KD value for the C1s-binding activity at neutral pH (KD(acidic pH)/KD (neutral pH)) is 2 or more when measured at a high calcium concentration at both neutral and acidic pH. In one aspect, in an isolated anti-C1s antibody of the present invention, the ratio of the koff value for its C1s-binding activity at acidic pH to the koff value for the C1s-binding activity at neutral pH (koff(acidic pH)/koff(neutral pH)) is 2 or more when measured at a high calcium concentration at both neutral and acidic pH. In one aspect, in an isolated anti-C1s antibody of the present invention, the ratio of the KD value for its C1s-binding activity at acidic pH to the KD value for the C1s-binding activity at neutral pH (KD(acidic pH)/KD (neutral pH)) is 5 or more when measured at a high calcium concentration at neutral pH and at a low calcium concentration at acidic pH. In some embodiments, in an isolated anti-C1s antibody of the present invention, the ratio of the KD value for its C1s-binding activity at acidic pH to the KD value for the C1s-binding activity at neutral pH (KD(acidic pH)/KD(neutral pH)) is 2 or more when measured at a low calcium concentration at both neutral and acidic pH, wherein the anti-C1s antibody binds to the dimeric state of C1s. In some embodiments, in an isolated anti-C1s antibody of the present invention, the ratio of the koff value for its C1s-binding activity at acidic pH to the koff value for the C1s-binding activity at neutral pH (koff(acidic pH)/koff (neutral pH)) is 2 or more when measured at a low calcium concentration at both neutral and acidic pH, wherein the anti-C1s antibody binds to the dimeric state of C1s.

Without being bound by a particular theory, in case that 1) an epitope structure of C1s bound by the antibody of the present invention can be conformationally changed by the non-existence of calcium thereby altering the affinity of the antibody or 2) the interaction (affinity or avidity) of the antibody of the present invention can vary depending on the condition of C1s (a monomeric state or a dimeric state), the measurement by using specific conditions (at a high calcium concentration at neutral pH and at a low calcium concentration at acidic pH) may be used to evaluate the ratio of the KD value (KD(acidic pH)/KD(neutral pH)).

In other words, the antibody of the present invention binds to C1s with a higher affinity at neutral pH than at acidic pH as described in (i) or (iii) below:
  (i) when measured at a high calcium concentration at both neutral and acidic pH, the ratio of the KD value for C1s-binding activity at acidic pH to the KD value for C1s-binding activity at neutral pH (KD(acidic pH)/KD (neutral pH)) is 2 or more,
  (ii) when measured at a high calcium concentration at both neutral and acidic pH, the ratio of the koff value for C1s-binding activity at acidic pH to the koff value for C1s-binding activity at neutral pH (koff(acidic pH)/koff(neutral pH)) is 2 or more,
  (iii) when measured at a high calcium concentration at neutral pH and at a low calcium concentration at acidic pH, the ratio of the KD value for C1s-binding activity at acidic pH to the KD value for C1s-binding activity at neutral pH (KD(acidic pH)/KD(neutral pH)) is 5 or more.

More generally, without being bound by a particular theory, in case that 1) an epitope structure of a certain antigen bound by an antibody of the present invention can be conformationally changed by the non-existence of calcium thereby altering the affinity of the antibody or 2) the interaction (affinity or avidity) of the antibody of the present invention can vary depending on the condition of the antigen (a monomeric state or a dimeric state), the measurement by using specific conditions (at a high calcium concentration at neutral pH and at a low calcium concentration at acidic pH) may be used to evaluate the ratio of the KD value (KD (acidic pH)/KD(neutral pH)). If this ratio is high, the affinity at acidic pH is lower than that at neutral pH. Alternatively, as mentioned below, KD is defined as the ratio of $K_{off}/k_{on}$. The ratio of the $k_{off}$ values between acidic and neutral conditions, i.e., ($k_{off}$(acidic pH)/koff (neutral pH)) may also be used for the comparison between the affinities at acidic and neutral pH.

Therefore, the antibody of the present invention binds to an antigen with a higher affinity at neutral pH than at acidic pH as follows: when measured at a high calcium concentration at neutral pH and at a low calcium concentration at acidic pH, the ratio of the KD value for antigen binding activity at acidic pH to the KD value for antigen binding activity at neutral pH (KD(acidic pH)/KD(neutral pH)) is 5 or more.

In one aspect, in an isolated anti-C1s antibody of the present invention, the ratio of the KD value for its C1s-binding activity at acidic pH to the KD value for the C1s-binding activity at neutral pH (KD(acidic pH)/KD (neutral pH)) is 2 or more when measured at a high calcium concentration at both neutral and acidic pH, wherein said antibody does not comprise CDR-H1 (SEQ ID NO. 23), CDR-H2 (SEQ ID NO. 24), CDR-H3 (SEQ ID NO. 25), CDR-L1 (SEQ ID NO. 26), CDR-L2 (SEQ ID NO. 27) and CDR-L3 (SEQ ID NO. 28).

In one aspect, in an isolated anti-C1s antibody of the present invention, the ratio of the KD value for its C1s-binding activity at acidic pH to the KD value for the C1s-binding activity at neutral pH (KD(acidic pH)/KD (neutral pH)) is 5 or more when measured at a high calcium concentration at neutral pH and at a low calcium concentration at acidic pH, wherein said antibody does not comprise CDR-H1 (SEQ ID NO. 23), CDR-H2 (SEQ ID NO. 24), CDR-H3 (SEQ ID NO. 25), CDR-L1 (SEQ ID NO. 26), CDR-L2 (SEQ ID NO. 27) and CDR-L3 (SEQ ID NO. 28).

In one aspect, in an isolated anti-C1s antibody of the present invention, the ratio of the KD value for its C1s-binding activity at acidic pH to the KD value for the C1s-binding activity at neutral pH (KD(acidic pH)/KD (neutral pH)) is 2 or more when measured at a low calcium concentration at both neutral and acidic pH, wherein the anti-C1s antibody binds to the dimeric state of C1s, wherein said antibody does not comprise CDR-H1 (SEQ ID NO. 23), CDR-H2 (SEQ ID NO. 24), CDR-H3 (SEQ ID NO. 25), CDR-L1 (SEQ ID NO. 26), CDR-L2 (SEQ ID NO. 27) and CDR-L3 (SEQ ID NO. 28).

The above-mentioned KD ratio, i.e., KD(acidic pH)/KD (neutral pH) may be compared between the parent antibody (i.e., the original antibody before modification of this invention) and an antibody into which one or more amino acid mutations (e.g., additions, insertions, deletions, or substitution) have been introduced with respect to the original (parent) antibody. The original (parent) antibody may be any known or newly isolated antibody as long as it specifically binds to C1s. Thus, in one aspect, in an isolated anti-C1s antibody of the present invention, the ratio of the KD value for the C1s-binding activity at acidic pH to the KD value for the C1s-binding activity at neutral pH (KD(acidic pH)/KD (neutral pH)) is at least 1.2 times, 1.4 times, 1.6 times, 1.8 times, 2 times, 2.1 times, 2.2 times, 2.3 times, 2.4 times, 2.5 times, 2.6 times, 2.7 times, 2.8 times, 2.9 times, 3 times, 3.5 times, 4 times, 5 times, 8 times, 10 times higher than the ratio of the KD value for the C1s-binding activity at acidic pH to the KD value for the C1s-binding activity at neutral pH (KD(acidic pH)/KD(neutral pH)) of the original (parent) antibody. In other words, the present invention provides an isolated anti-C1s antibody wherein the isolated anti-C1s antibody has been introduced with one or more amino acid mutations (e.g., additions, insertions, deletions, or substitution) from a parent (original) antibody, and the ratio of (i) to (ii) below is at least 1.2, 1.4, 1.6, 1.8, 2, 2.1, 2.2, 2.3, 2.4, 2.5, 2.5, 2.7, 2.8, 2.9, 3, 3.5, 4, 5, 8, or 10: (i) the ratio of the KD value for the C1s-binding activity at acidic pH to the KD value for the C1s-binding activity at neutral pH (KD(acidic pH)/KD(neutral pH)) of the isolated anti-C1s antibody; (ii) the ratio of the KD value for the C1s-binding activity at acidic pH to the KD value for the C1s-binding activity at neutral pH (KD(acidic pH)/KD(neutral pH)) of the parent (original) antibody. These KD ratio may be measured at any (high or low) calcium concentration, e.g., measured at a high calcium concentration at both neutral and acidic pH, or measured at a high calcium concentration at neutral pH and at a low calcium concentration at acidic pH. In a further aspect, it is possible to use the dissociation rate constant (kd) instead of KD above to evaluate pH and/or Ca dependency.

In one aspect, antibodies of the present invention have antigen-binding activity which is different between intracellular condition and extracellular condition. Intracellular and extracellular conditions refer to conditions that are different between inside and outside of the cell. Categories of conditions include, for example, ion concentration, more specifically, metal ion concentration, hydrogen ion concentration (pH) and calcium ion concentration. "Intracellular condition" preferably refers to an environment characteristic to the environment inside the endosome, while "extracellular condition" preferably refers to an environment characteristic to the environment in plasma. Antibodies with the property of having an antigen-binding activity that changes according to the ion concentration can be obtained by screening a large number of antibodies for domains having such property. For example, antibodies with the above-described property can be obtained by producing a large number of antibodies whose sequences are different from each another by a hybridoma method or an antibody library method, and measuring their antigen binding activities at different ion concentrations. The B cell cloning method is one of examples of methods of screening for such antibodies. Furthermore, as described below, at least one distinctive amino acid residue that can confer an antibody with the property of having an antigen-binding activity that changes according to the ion concentration is specified, to prepare as a library of a large number of antibodies that have different sequences while sharing the distinctive amino acid residues as a common structure. Such a library can be screened to efficiently isolate antibodies that have the property described above.

In one aspect, the invention provides an antibody that binds to C1s with a higher affinity at neutral pH than at acidic pH. In another aspect, the invention provides anti-C1s antibodies that exhibit pH-dependent binding to C1s. As used herein, the expression "pH-dependent binding" means "reduced binding at acidic pH as compared to at neutral pH", and both expressions may be interchangeable. For example, anti-C1s antibodies "with pH-dependent binding characteristics" include antibodies that bind to C1s with higher affinity at neutral pH than at acidic pH.

In certain embodiment, the ratio of the KD value for C1s-binding activity at acidic pH to the KD value for C1s-binding activity at neutral pH (KD(acidic pH)/KD (neutral pH)) is 2 or more when measured at a high calcium concentration at both neutral and acidic pH. In particular embodiments, the antibodies of the present invention bind to C1s with at least 2, 2.1, 2.2, 2.3, 2.4, 2.5, 2.6, 2.7, 2.8, 2.9, 3, 5, 10, 15, 20, 25, 30, 35, 40, 45, 50, 55, 60, 65, 70, 75, 80, 85, 90, 95, 100, 200, 400, 1000, 10000, or more times higher affinity at neutral pH than at acidic pH.

In certain embodiment, the ratio of the koff value for C1s-binding activity at acidic pH to the koff value for C1s-binding activity at neutral pH (koff (acidic pH)/koff (neutral pH)) is 2 or more when measured at a high calcium concentration at both neutral and acidic pH. In particular embodiments, the antibodies of the present invention bind to C1s with at least 2, 2.1, 2.2, 2.3, 2.4, 2.5, 2.6, 2.7, 2.8, 2.9, 3, 5, 10, 15, 20, 25, 30, 35, 40, 45, 50, 55, 60, 65, 70, 75, 80, 85, 90, 95, 100, 200, 400, 1000, 10000, or more times higher affinity at neutral pH than at acidic pH.

In certain embodiment, the ratio of the KD value for C1s-binding activity at acidic pH to the KD value for C1s-binding activity at neutral pH (KD(acidic pH)/KD (neutral pH)) is 2 or more when measured at a high calcium concentration at neutral pH and at a low calcium concentration at acidic pH. In particular embodiments, the antibodies of the present invention bind to C1s with at least 2, 3, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95, 100, 200, 400, 1000, 10000, or more times higher affinity at neutral pH than at acidic pH.

In the above-mentioned cases, for example, acidic pH is 5.8 and neutral pH is 7.4, thus KD(acidic pH)/KD(neutral pH) is KD(pH 5.8)/KD(pH 7.4). In this connection, examples of acidic pH and neutral pH are herein described in detail later. In some embodiments, KD(acidic pH)/KD (neutral pH) such as KD(pH 5.8)/KD(pH 7.4) may be 2 to 10,000. In the above-mentioned cases, for example, acidic pH is 5.8 and neutral pH is 7.4, thus koff(acidic pH)/koff (neutral pH) is koff(pH 5.8)/koff(pH 7.4). In this connection, examples of acidic pH and neutral pH are herein described in detail later. In some embodiments, koff(acidic pH)/koff (neutral pH) such as koff(pH 5.8)/koff (pH 7.4) may be 2 to 10,000.

When an antigen is a soluble protein, the binding of an antibody to the antigen can result in an extended half-life of the antigen in plasma (i.e., reduced clearance of the antigen from plasma), since the antibody can have a longer half-life in plasma than the antigen itself and may serve as a carrier for the antigen. This is due to the recycling of the antigen-antibody complex by FcRn through the endosomal pathway in cell (Roopenian and Akilesh (2007) Nat Rev Immunol 7(9): 715-725). However, an antibody with pH-dependent binding characteristics, which binds to its antigen in neutral extracellular environment while releasing the antigen into acidic endosomal compartments following its entry into cells, is expected to have superior properties in terms of antigen neutralization and clearance relative to its counterpart that binds in a pH-independent manner (Igawa et al (2010) Nature Biotechnol 28(11); 1203-1207;

Devanaboyina et al (2013) mAbs 5(6): 851-859; International Patent Application Publication No: WO 2009/125825).

In one aspect, the invention provides an antibody that binds to C1s with a higher affinity under a high calcium concentration condition than under a low calcium concentration condition.

In the present invention, preferred metal ions include, for example, calcium ion. Calcium ion is involved in modulation of many biological phenomena, including contraction of muscles such as skeletal, smooth, and cardiac muscles; activation of movement, phagocytosis, and the like of leukocytes; activation of shape change, secretion, and the like of platelets; activation of lymphocytes; activation of mast cells including secretion of histamine; cell responses mediated by catecholamine alpha receptor or acetylcholine receptor; exocytosis; release of transmitter substances from neuron terminals; and axoplasmic flow in neurons. Known intracellular calcium ion receptors include troponin C, calmodulin, parvalbumin, and myosin light chain, which have several calcium ion-binding sites and are believed to be derived from a common origin in terms of molecular evolution. There are also many known calcium-binding motifs. Such well-known motifs include, for example, cadherin domains, EF-hand of calmodulin, C2 domain of Protein kinase C, Gla domain of blood coagulation protein Factor IX, C-type lectins of acyaroglycoprotein receptor and mannose-binding receptor, A domains of LDL receptors, annexin, thrombospondin type 3 domain, and EGF-like domains.

In the present invention, when the metal ion is calcium ion, it is desirable that the antigen-binding activity is lower under a low calcium ion concentration condition than under a high calcium ion concentration condition. Meanwhile, the intracellular calcium ion concentration is lower than the extracellular calcium ion concentration. Conversely, the extracellular calcium ion concentration is higher than the intracellular calcium ion concentration. In the present invention, the low calcium ion concentration is preferably 0.1 micromolar (micro M) to 30 micro M, more preferably 0.5 micro M to 10 micro M, and particularly preferably 1 micro M to 5 micro M which is close to the calcium ion concentration in the early endosome in vivo. Meanwhile, in the present invention, the high calcium ion concentration is preferably 100 micro M to 10 micro M, more preferably 200 micro M to 5 mM, and particularly preferably 0.5 mM to 2.5 mM which is close to the calcium ion concentration in plasma (in blood). In the present invention, it is preferable that the low calcium ion concentration is the calcium ion concentration in endosomes, and the high calcium ion concentration is the calcium ion concentration in plasma. When the level of antigen-binding activity is compared between low and high calcium ion concentrations, it is preferable that the binding of antibodies of the present invention is stronger at a high calcium ion concentration than at a low calcium ion concentration. In other words, it is preferable that the antigen-binding activity of an antibody of the present invention is lower at a low calcium ion concentration ion than at a high calcium ion concentration. When the level of binding activity is expressed with the dissociation constant (KD), the value of KD (low calcium ion concentration)/KD (high calcium ion concentration) is greater than 1, preferably 2 or more, still more preferably 10 or more, and yet more preferably 40, 45, 50, 55, 60, 65, 70, 75, 80, 85, 90, 95, 100, 200, 400, 1000, 10000 or more. The upper limit of the value of KD (low calcium ion concentration)/KD (high calcium ion concentration) is not particularly limited, and may be any value such as 100, 400, 1000, or 10000, as long as it can be produced with the techniques of skilled artisans. It is possible to use the dissociation rate constant (kd) instead of KD. When it is difficult to calculate the KD value, the activity may be assessed based on the level of binding response in Biacore when analytes are passed at the same concentration. When antigens are passed over a chip immobilized with antigen-binding molecules of the present invention, the binding response at a low calcium concentration is preferably ½ or less of the binding response at a high calcium concentration, more preferably ⅓ or less, still more preferably ⅕ or less, and particularly preferably ¹⁄₁₀ or less. It is known that in general the in vivo extracellular calcium ion concentration (for example, in plasma) is high, and the intracellular calcium ion concentration (for example, in the endosome) is low. Thus, in the present invention, it is preferable that the extracellular condition is a high calcium ion concentration, and the intracellular condition is a low calcium ion concentration. When the property that the antigen-binding activity is lower under an intracellular calcium ion concentration condition than under an extracellular calcium ion concentration condition is conferred to an antigen-binding molecule (e.g., an antibody) of the present invention, antigens that have bound to the antigen-binding molecule of the present invention outside of the cell dissociate from the antigen-binding molecule of the present invention inside the cell, thereby enhancing antigen incorporation into the cell from the outside of the cell. Such antibodies, when administered to the living body, can reduce antigen concentration in plasma and reduce the physiological activity of antigens in vivo. Thus, antibodies of the present invention are useful. Methods of screening for antigen-binding domains or antibodies having a lower antigen-binding activity under a low calcium ion concentration condition than under a high calcium ion concentration condition include, for example, the method described in WO2012/073992 (for example, paragraphs 0200-0213). Methods for conferring antigen-binding domains of the present invention with the property of binding more weakly to antigens under a low calcium ion concentration condition than under a high calcium ion concentration condition are not particularly limited, and may be carried out by any methods. Specifically, the methods are described in Japanese Patent Application No. 2011-218006 and include, for example, methods for substituting at least one amino acid residue in an antigen-binding domain with an amino acid residue having metal chelating activity, and/or inserting into an antigen-binding domain at least one amino acid residue having metal chelating activity. Antigen-binding molecules of the present invention in which at least one amino acid residue of the antigen-binding domain has been substituted with an amino acid residue having metal chelating activity and/or at least one amino acid residue having metal chelating activity has been inserted into the antigen-binding domain are a preferred embodiment of antigen-binding molecules of the present invention.

Amino acid residues having metal chelating activity preferably include, for example, serine, threonine, asparagine, glutamine, aspartic acid, and glutamic acid. Furthermore, amino acid residues that change the antigen-binding activity of antigen binding domains according to the calcium ion concentration preferably include, for example, amino acid residues that form a calcium-binding motif. Calcium-binding motifs are well known to those skilled in the art, and have been described in detail (for example, Springer et al., (Cell (2000) 102, 275-277); Kawasaki and Kretsinger (Protein Prof. (1995) 2, 305-490); Moncrief et al., (J. Mol. Evol.

(1990) 30, 522-562); Chauvaux et al., (Biochem. J. (1990) 265, 261-265); Bairoch and Cox (FEBS Lett. (1990) 269, 454-456); Davis (New Biol. (1990) 2, 410-419); Schaefer et al., (Genomics (1995) 25, 638 to 643); Economou et al., (EMBO J. (1990) 9, 349-354); Wurzburg et al., (Structure. (2006) 14, 6, 1049-1058)). EF hand in troponin C, calmodulin, parvalbumin, and myosin light chain; C2 domain in protein kinase C; Gla domain in blood coagulation protein factor IX; C-type lectin of acyaroglycoprotein receptor and mannose-binding receptor, ASGPR, CD23, and DC-SIGN; A domain in LDL receptor; annexin domain; cadherin domain; thrombospondin type 3 domain; and EGF-like domain are preferably used as calcium binding motifs.

Antigen-binding domains of the present invention can contain amino acid residues that change the antigen-binding activity according to the calcium ion concentration, such as the above-described amino acid residues with metal chelating activity and amino acid residues that form a calcium-binding motif. The location of such amino acid residues in the antigen-binding domain is not particularly limited, and they may be located at any position as long as the antigen binding activity changes according to the calcium ion concentration. Meanwhile, such amino acid residues may be contained alone or in combination of two or more, as long as the antigen binding activity changes according to the calcium ion concentration. The amino acid residues preferably include, for example, serine, threonine, asparagine, glutamine, aspartic acid, and glutamic acid. When an antigen-binding domain is an antibody variable region, the amino acid residues may be contained in the heavy chain variable region and/or the light chain variable region. In a preferred embodiment, the amino acid residues may be contained in the CDR3 of the heavy chain variable region, more preferably at positions 95, 96, 100a, and/or 101 according to Kabat numbering in the CDR3 of the heavy chain variable region.

In another preferred embodiment, the amino acid residues may be contained in the CDR1 of the light chain variable region, more preferably at positions 30, 31, and/or 32 according to Kabat numbering in the CDR1 of the light chain variable region. In still another preferred embodiment, the amino acid residues may be contained in the CDR2 of the light chain variable region, more preferably at position 50 according to Kabat numbering in the CDR2 of the light chain variable region. In yet another preferred embodiment, the amino acid residues may be contained in the CDR3 of the light chain variable region, more preferably at position 92 according to Kabat numbering in the CDR3 of the light chain variable region.

Furthermore, it is possible to combine the above-described embodiments. For example, the amino acid residues may be contained in two or three CDRs selected from the CDR1, CDR2, and CDR3 of the light chain variable region, more preferably at any one or more of positions 30, 31, 32, 50, and/or 92 according to Kabat numbering in the light chain variable region.

A large number of antigen-binding domains that have different sequences while sharing as a common structure the above-described amino acid residues that change the antigen-biding activity according to the calcium ion concentration, are prepared as a library. The library can be screened to efficiently obtain antigen-binding domains with binding activity to a desired antigen, in which their antigen-binding activity changes according to the calcium ion concentration.

The "affinity" of an antibody for C1s, for purposes of the present disclosure, is expressed in terms of the KD of the antibody. The KD of an antibody refers to the equilibrium dissociation constant of an antibody-antigen interaction. The greater the KD value is for an antibody binding to its antigen, the weaker its binding affinity is for that particular antigen. Accordingly, as used herein, the expression "higher affinity at neutral pH than at acidic pH" (or the equivalent expression "pH-dependent binding") means that the KD of the antibody at acidic pH is greater than the KD of the antibody at neutral pH. For example, in the context of the present invention, an antibody is considered to bind to C1s with higher affinity at neutral pH than at acidic pH if the KD of the antibody binding to C1s at acidic pH is at least 2 times greater than the KD of the antibody binding to C1s at neutral pH. Thus, the present invention includes antibodies that bind to C1s at acidic pH with a KD that is at least 2, 2.1, 2.2, 2.3, 2.4, 2.5, 2.6, 2.7, 2.8, 2.9, 3, 5, 10, 15, 20, 25, 30, 35, 40, 45, 50, 55, 60, 65, 70, 75, 80, 85, 90, 95, 100, 200, 400, 1000, 10000, or more times greater than the KD of the antibody binding to C1s at neutral pH. In another embodiment, the KD value of the antibody at neutral pH can be 10-7 M, 10-8 M, 10-9 M, 10-10 M, 10-11 M, 10-12 M, or less. In another embodiment, the KD value of the antibody at acidic pH can be 10-9 M, 10-8 M, 10-7 M, 10-6 M, or greater.

The binding properties of an antibody for a particular antigen may also be expressed in terms of the kd of the antibody. The kd of an antibody refers to the dissociation rate constant of the antibody with respect to a particular antigen and is expressed in terms of reciprocal seconds (i.e., sec-1). An increase in kd value signifies weaker binding of an antibody to its antigen. The present invention therefore includes antibodies that bind to C1s with a higher kd value at acidic pH than at neutral pH. The present invention includes antibodies that bind to C1s at acidic pH with a kd that is at least 2, 2.1, 2.2, 2.3, 2.4, 2.5, 2.6, 2.7, 2.8, 2.9, 3, 5, 10, 15, 20, 25, 30, 35, 40, 45, 50, 55, 60, 65, 70, 75, 80, 85, 90, 95, 100, 200, 400, 1000, 10000, or more times greater than the kd of the antibody binding to C1s at neutral pH. In another embodiment, the kd value of the antibody at neutral pH can be 10-2 l/s, 10-3 l/s, 10-4 l/s, 10-5 l/s, 10-6 l/s, or less. In another embodiment, the kd value of the antibody at acidic pH can be 10-3 l/s, 10-2 l/s, 10-1 l/s, or greater.

In certain instances, a "reduced binding at acidic pH as compared to at neutral pH" is expressed in terms of the ratio of the KD value of the antibody at acidic pH to the KD value of the antibody at neutral pH (or vice versa). For example, an antibody may be regarded as exhibiting "reduced binding to C1s at acidic pH as compared to its binding at neutral pH", for purposes of the present invention, if the antibody exhibits an acidic/neutral KD ratio of 2 or greater. In certain exemplary embodiments, the acidic/neutral KD ratio for an antibody of the present invention can be 2, 2.1, 2.2, 2.3, 2.4, 2.5, 2.6, 2.7, 2.8, 2.9, 3, 5, 10, 15, 20, 25, 30, 35, 40, 45, 50, 55, 60, 65, 70, 75, 80, 85, 90, 95, 100, 200, 400, 1000, 10000, or greater. In another embodiment, the KD value of the antibody at neutral pH can be 10-7 M, 10-8 M, 10-9 M, 10-10 M, 10-11 M, 10-12 M, or less. In another embodiment, the KD value of the antibody at acidic pH can be 10-9 M, 10-8 M, 10-7 M, 10-6 M, or greater.

Alternatively, a "reduced binding at acidic pH as compared to at neutral pH" is expressed in terms of the ratio of the koff value of the antibody at acidic pH to the koff value of the antibody at neutral pH (or vice versa). For example, an antibody may be regarded as exhibiting "reduced binding to C1s at acidic pH as compared to its binding at neutral pH", for purposes of the present invention, if the antibody exhibits an acidic/neutral koff ratio of 2 or greater. In certain exemplary embodiments, the acidic/neutral koff ratio for an antibody of the present invention can be 2, 2.1, 2.2, 2.3, 2.4, 2.5, 2.6, 2.7, 2.8, 2.9, 3, 5, 10, 15, 20, 25, 30, 35, 40, 45, 50, 55, 60, 65, 70, 75, 80, 85, 90, 95, 100, 200, 400, 1000, 10000, or greater.

In certain instances, a "reduced binding at acidic pH as compared to at neutral pH" is expressed in terms of the ratio of the kd value of the antibody at acidic pH to the kd value of the antibody at neutral pH (or vice versa). For example, an antibody may be regarded as exhibiting "reduced binding to C1s at acidic pH as compared to its binding at neutral pH", for purposes of the present invention, if the antibody exhibits an acidic/neutral kd ratio of 2 or greater. In certain exemplary embodiments, the acidic/neutral kd ratio for an antibody of the present invention can be 2, 2.1, 2.2, 2.3, 2.4, 2.5, 2.6, 2.7, 2.8, 2.9, 3, 5, 10, 15, 20, 25, 30, 35, 40, 45, 50, 55, 60, 65, 70, 75, 80, 85, 90, 95, 100, 200, 400, 1000, 10000, or greater. In another embodiment, the kd value of the antibody at neutral pH can be 10-2 1/s, 10-3 1/s, 10-4 1/s, 10-5 1/s, 10-6 1/s, or less. In another embodiment, the kd value of the antibody at acidic pH can be 10-3 1/s, 10-2 1/s, 10-1 1/s, or greater.

In certain embodiment, the ratio of the KD value of the anti-C1s antibody with pH and/or Ca dependency of the present invention for C1s-binding activity at acidic pH to the KD value for C1s-binding activity at neutral pH (KD(acidic pH)/KD(neutral pH)) is the same or greater than that of the reference antibody selected from the group consisting of 1) to 5) below.
1) an antibody comprising the VH and VL sequences in SEQ ID NO: 19 and SEQ ID NO: 20, respectively,
2) an antibody comprising the VH and VL sequences in SEQ ID NO: 17 and SEQ ID NO: 18, respectively,
3) an antibody comprising the VH and VL sequences in SEQ ID NO: 22 and SEQ ID NO: 20, respectively,
4) an antibody comprising the VH and VL sequences in SEQ ID NO: 19 and SEQ ID NO: 21, respectively, and
5) an antibody comprising the VH and VL sequences in SEQ ID NO: 22 and SEQ ID NO: 21, respectively.

In a further embodiment, anti-C1s antibodies such as IPN92H0288-SG4GK/IPN93L0211-SK1, IPN92H0288-SG4GK/IPN93L0058-SK1, and IPN92H0307-SG4GK/IPN93L0058-SK1 disclosed in Examples 4 can be used as the reference antibody above.

As used herein, the expression "acidic pH" means a pH of 4.0 to 6.5. The expression "acidic pH" includes pH values of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, and 6.5. In particular aspects, the "acidic pH" is 5.8 or 6.0.

As used herein, the expression "neutral pH" means a pH of 6.7 to about 10.0. The expression "neutral pH" includes pH values of 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0. In particular aspects, the "neutral pH" is 7.0 or 7.4.

As used herein, the expression "under high calcium concentration condition" or "at a high calcium concentration" means 100 micro M to 10 mM, more preferably 200 micro M to 5 mM, and particularly preferably 0.5 mM to 2.5 mM which is close to the calcium ion concentration in plasma (in blood). The expression "under high calcium concentration condition" or "at a high calcium concentration" includes calcium concentration values of 100 micro M, 200 micro M, 300 micro M, 400 micro M, 500 micro M, 600 micro M, 700 micro M, 800 micro M, 900 micro M, 0.5 mM, 0.7 mM, 0.9 mM, 1 mM, 1.2 mM, 1.4 mM, 1.6 mM, 1.8 mM, 2.0 mM, 2.2 mM, 2.4 mM, 2.5 mM, 3 mM, 4 mM, 5 mM, 6 mM, 7 mM, 8 mM, 9 mM, and 10 mM Ca2+. In particular aspects, "under high calcium concentration condition" or "at a high calcium concentration" refers to 1.2 mM Ca2+.

As used herein, the expression "under low calcium concentration condition" or "at a low calcium concentration" means 0.1 micro M to 30 micro M, more preferably 0.5 micro M to 10 micro M, and particularly preferably 1 micro M to 5 micro M which is close to the calcium ion concentration in the early endosome in vivo. The expression "under low calcium concentration condition" or "at a low calcium concentration" includes calcium concentration values of 0.1 micro M, 0.5 micro M, 1 micro M, 1.5 micro M, 2.0 micro M, 2.5 micro M, 2.6 micro M, 2.7 micro M, 2.8 micro M, 2.9 micro M, 3.0 micro M, 3.1 micro M, 3.2 micro M, 3.3 micro M, 3.4 micro M, 3.5 micro M, 4.0 micro M, 5.0 micro M, 6.0 micro M, 7.0 micro M, 8.0 micro M, 9.0 micro M, 10 micro M, 15 micro M, 20 micro M, 25 micro M, and 30 micro M Ca2+. In particular aspects, "under low calcium concentration condition" or "at a low calcium concentration" refers to 3.0 micro M Ca2+.

KD values and kd values, as expressed herein, may be determined using a surface plasmon resonance-based biosensor to characterize antibody-antigen interactions. (See, e.g., Example 2, herein). KD values and kd values can be determined at 25 degrees Celsius (C) or 37 degrees C. This determination can be performed in the presence of 150 mM NaCl. In some embodiments, this determination can be performed by using a surface plasmon resonance technique in which the antibody is immobilized, the antigen serves as analyte, and the following conditions are used: 10 mM MES buffer, 0.05% polyoxyethylenesorbitan monolaurate, and 150 mM NaCl at 37 degrees Celsius (C).

In one aspect, the invention provides an anti-C1s antibody with pH dependency, wherein the antibody comprises at least one histidine in the variable region, wherein at least one amino acid at the variable region is substituted with other amino acids, such that
1) non-specific binding activity at acidic pH and/or at neutral pH of the antibody will be reduced, or
2) the ratio of the KD value for C1s-binding activity at acidic pH to the KD value for C1s-binding activity at neutral pH (KD(acidic pH)/KD(neutral pH)) will be increased.

In one aspect, the invention provides an anti-C1s antibody with pH dependency, wherein the antibody comprises at least one histidine in the variable region, wherein at least one amino acid at the variable region is substituted with an amino acid selected from the group consisting of D, E, K, R and Q, such that
1) non-specific binding activity at acidic pH and/or at neutral pH of the antibody will be reduced, or
2) the ratio of the KD value for C1s-binding activity at acidic pH to the KD value for C1s-binding activity at neutral pH (KD(acidic pH)/KD(neutral pH)) will be increased.

In a certain aspect, the expression "non-specific binding activity" means extracellular matrix (ECM) binding activity of the antibody. In a certain aspect, the expression "non-specific binding activity" means ECM binding activity of the antibody at acidic pH. In certain embodiments, at least one amino acid in an anti-C1s antibody of the instant invention may be substituted with one or more amino acids such that the ECM binding activity is reduced at acidic pH. In certain embodiments, at least one amino acid in an anti-C1s antibody of the instant invention may be substituted with one or more amino acids such that the ECM binding activity is reduced at neutral pH.

In one aspect, the invention provides an anti-C1s antibody with pH dependency, wherein at least one amino acid is substituted in the variable region, such that the ECM binding activity of the antibody will be reduced. In certain embodiments, the ECM binding activity is reduced at acidic pH. In certain embodiments, the ECM binding activity is reduced at neutral pH. In certain embodiments, such an antibody refers to an antibody with one or more alterations in one or more hypervariable regions (HVRs), compared to a parent antibody which does not possess such alterations, such alterations resulting in an improvement in the ECM binding activity of the antibody for antigen, i.e. reducing the ECM binding activity.

The method for measuring "extracellular matrix-binding" is not particularly limited, and measurements can be carried out using an ELISA system that detects binding between a polypeptide and extracellular matrix by adding the polypeptide to an extracellular matrix-immobilized plate, and adding a labeled antibody against the polypeptide. In particular, a measurement method using the electrochemiluminescence (ECL) method is preferred since it enables detection of extracellular matrix-binding ability with higher sensitivity. Specifically, a mixture of polypeptide and ruthenium antibody is added to an extracellular matrix-immobilized plate, and the binding between the polypeptide and extracellular matrix can be measured using an ECL system that measures the electrochemiluminescence of ruthenium. The concentration of polypeptide added can be arbitrarily set, and it is preferable to add high concentrations to increase the detection sensitivity of extracellular matrix binding. While the extracellular matrix used in the present invention may be plant-derived or animal-derived as long as it contains glycoproteins such as collagen, proteoglycans, fibronectin, laminin, entactin, fibrin, and perlecan, animal-derived extracellular matrix is preferred in the present invention; and for example, extracellular matrix derived from animals such as humans, mice, rats, monkeys, rabbits, and dogs can be used. In particular, for monitoring the improvement of plasmacokinetics in humans, naturally-occurring human extracellular matrices derived from humans are preferred. Furthermore, the condition for evaluating the binding of polypeptides to extracellular matrix is desirably in a neutral range near pH 7.4 (physiological condition), but it does not necessarily have to be in the neutral range, and evaluation may also be performed in the acidic range (near pH 6.0). Furthermore, when evaluating the binding of a polypeptide to extracellular matrix, an antigen molecule bound by the polypeptide can be made to coexist for evaluation of the binding of the polypeptide/antigen molecule complex to the extracellular matrix.

In some embodiments, whether or not non-specific binding activity at acidic pH of the antibody will be reduced, can be measured by using, for example, ELISA or ECL mentioned elsewhere (see, e.g., Example 4). In further embodiments, in an isolated anti-C1s antibody of the present invention, the value of ECM binding may be compared between the parent antibody (i.e., the original antibody before D, E, K, R and/or Q substitution) and an antibody into which one or more amino acid substitutions (D, E, K, R and/or Q) have been introduced with respect to the original (parent) antibody, provided that the antibody comprises at least one histidine in the variable region. The original (parent) antibody may be any known or newly isolated antibody as long as it specifically binds to C1s. Thus, in one aspect, in an isolated anti-C1s antibody of the present invention, the value of the ECM binding of the substituted antibody is at least 1.2 times, 1.4 times, 1.6 times, 1.8 times, 2 times, 2.5 times, 3 times, 3.5 times, 4 times, 5 times, 8 times, 10 times lower than the value of the ECM binding of the original (parent) antibody.

Without being bounded by a particular theory, a histidine residue in the antibody can interact with various residues surrounding the histidine residue in the antibody. Such interaction can affect the structure of the antibody or the conformation of the CDRs. Histidine becomes protonated and positively charged at the acidic pH. Introduction of positively charged residue, such as arginine or lysine, at the position surrounding the histidine can cause repulsion between the positively charged residue and the protonated histidine at acidic pH, and thus induce structural or conformational change of the antibody or the CDRs. Similarly, introduction of negatively charged residue, such as aspartic acid or glutamic acid, at the position surrounding the histidine can cause interaction between the negatively charged residue and the protonated histidine at acidic pH, and thus induce structural or conformational change of the antibody or the CDRs. These structural or conformational changes of the antibody or the CDRs that occur at acidic pH can affect the antigen binding of the antibody, and reduce the binding affinity of the antibody to an antigen at acidic pH. In summary, introduction of charged residue (such as arginine, lysine, aspartic acid or glutamic acid) at the position surrounding the histidine residue in an antibody can reduce the binding affinity of the antibody to the antigen at acidic pH, and thus improve the pH dependency of antibody-antigen interaction in a unique mechanism.

In one aspect, the present invention provides a method for increasing the ratio of the KD value for antigen-binding activity of an antibody at acidic pH to the KD value for antigen-binding activity at neutral pH (KD(acidic pH)/KD (neutral pH)), comprising
1) providing an antibody with pH dependency comprising at least one histidine in the variable region,
2) substituting at least one amino acid at the variable region of the antibody with an amino acid selected from the group consisting of D, E, K, R, Q and H.

In one aspect, the present invention provides a method for enhancing the clearance of (or removing) an antigen from plasma, comprising
1) providing an antibody with pH dependency comprising at least one histidine in the variable region,
2) substituting at least one amino acid at the variable region of the antibody with an amino acid selected from the group consisting of D, E, K, R, Q and H.

In one aspect, the present invention provides a method for facilitating antigen-binding molecule-mediated antigen uptake into a cell, comprising
1) providing an antibody with pH dependency comprising at least one histidine in the variable region,
2) substituting at least one amino acid at the variable region of the antibody with an amino acid selected from the group consisting of D, E, K, R, Q and H.

In one aspect, the present invention provides a method for increasing the number of antigens to which a single antigen-binding molecule can bind, comprising
1) providing an antibody with pH dependency comprising at least one histidine in the variable region,
2) substituting at least one amino acid at the variable region of the antibody with an amino acid selected from the group consisting of D, E, K, R, Q and H.

In one aspect, the present invention provides a method for augmenting the ability of an antigen-binding molecule to eliminate an antigen from plasma, comprising 1) providing an antibody with pH dependency comprising at least one histidine in the variable region,
2) substituting at least one amino acid at the variable region of the antibody with an amino acid selected from the group consisting of D, E, K, R, Q and H.

In certain embodiments, in the above-mentioned method of the present invention, the distance between the histidine residue comprised at the variable region and the substituted amino acid (i.e., D, E, K, R, Q, or H) is less than 20 angstrom, 18 angstrom, 16 angstrom, 14 angstrom, 12 angstrom, 10 angstrom, 8 angstrom, 6 angstrom, 4 angstrom, or 2 angstrom.

In one aspect, the invention provides a method of enhancing the clearance of C1s from plasma in an individual. In some embodiments, the method comprises administering to the individual an effective amount of an anti-C1s antibody of the present invention to enhance the clearance of C1s from plasma. The invention also provides a method of enhancing the clearance of the complex of C1r and C1s from plasma in an individual. In some embodiments, the method comprises administering to the individual an effective amount of an anti-C1s antibody of the present invention to enhance the clearance of the complex of C1r and C1s from plasma. The invention also provides a method of enhancing the clearance of the complex of C1q, C1r and C1s from plasma in an individual. In some embodiments, the method comprises administering to the individual an effective amount of an anti-C1s antibody of the present invention to enhance the clearance of the complex of C1q, C1r and C1s from plasma.

In another aspect, the invention provides a method of removing C1s from plasma, the method comprising: (a) identifying an individual in need of having C1s removed from the individual's plasma; (b) providing an antibody that binds to C1s through the antigen-binding (C1s-binding) domain of the antibody and has a KD(pH5.8)/KD(pH7.4) value, defined as the ratio of KD for C1s at pH 5.8 and KD for C1s at pH 7.4, of 2 to 10,000, when KD is determined using a surface plasmon resonance technique, wherein the antibody binds to C1s in plasma in vivo and dissociates from the bound C1s under conditions present in an endosome in vivo, and wherein the antibody is a human IgG or a humanized IgG; and (c) administering the antibody to the individual. In further aspect, such a surface plasmon resonance technique can be used at 37 degrees C. and 150 mM NaCl. In further aspect, such a surface plasmon resonance technique can be used in which the antibody is immobilized, the antigen serves as analyte, and the following conditions are used: 10 mM MES buffer, 0.05% polyoxyethylenesorbitan monolaurate, and 150 mM NaCl at 37 degrees C. In a further aspect, it is possible to use the dissociation rate constant (kd) instead of KD above.

In another aspect, the invention provides a method of removing C1s from plasma in a subject, the method comprising: (a) identifying a first antibody that binds to C1s through the antigen-binding domain of the first antibody; (b) identifying a second antibody that: (1) binds to C1s through the antigen-binding (C1s-binding) domain of the second antibody, (2) is identical in amino acid sequence to the first antibody except having at least one amino acid of a variable region of the first antibody substituted with histidine and/or at least one histidine inserted into a variable region of the first antibody, (3) has a KD(pH5.8)/KD(pH7.4) value that is higher than the first antibody's KD(pH5.8)/KD(pH7.4) value, and is between 2 and 10,000, wherein KD(pH5.8)/KD(pH7.4) is defined as the ratio of KD for C1s at pH 5.8 and KD for C1s at pH 7.4 when KD is determined using a surface plasmon resonance technique, (4) binds to C1s in plasma in vivo, (5) dissociates from the bound C1s under conditions present in an endosome in vivo, and (6) is a human IgG or a humanized IgG; (c) identifying a subject in need of having his or her plasma level of C1s reduced; and (d) administering the second antibody to the subject so that the plasma level of C1s in the subject is reduced. In further aspect, such a surface plasmon resonance technique can be used at 37 degrees C. and 150 mM NaCl. In further aspect, such a surface plasmon resonance technique can be used at 37 degrees C. and 150 mM NaCl. In further aspect, such a surface plasmon resonance technique can be used in which the antibody is immobilized, the antigen serves as analyte, and the following conditions are used: 10 mM MES buffer, 0.05% polyoxyethylenesorbitan monolaurate, and 150 mM NaCl at 37 degrees C. In a further aspect, it is possible to use the dissociation rate constant (kd) instead of KD above.

In another aspect, the invention provides a method of removing C1s from plasma in a subject, the method comprising: (a) identifying a first antibody that: (1) binds to C1s through the antigen-binding domain of the first antibody, (2) is identical in amino acid sequence to a second antibody that binds to C1s through the antigen-binding (C1s-binding) domain of the second antibody, except that at least one variable region of the first antibody has at least one more histidine residue than does the corresponding variable region of the second antibody, (3) has a KD(pH5.8)/KD(pH7.4) value that is higher than the second antibody's KD(pH5.8)/KD(pH7.4) value, and is between 2 and 10,000, wherein KD(pH5.8)/KD(pH7.4) is defined as the ratio of KD for C1s at pH 5.8 and KD for C1s at pH 7.4 when KD is determined using a surface plasmon resonance technique, (4) binds to C1s in plasma in vivo, (5) dissociates from the bound C1s under conditions present in an endosome in vivo, and (6) is a human IgG or a humanized IgG; (b) identifying a subject in need of having his or her plasma level of C1s reduced; and (c) administering the first antibody at least once to the subject so that the plasma level of C1s in the subject is reduced. In further aspect, such a surface plasmon resonance technique can be used at 37 degrees C. and 150 mM NaCl. In further aspect, such a surface plasmon resonance technique can be used at 37 degrees C. and 150 mM NaCl. In further aspect, such a surface plasmon resonance technique can be used in which the antibody is immobilized, the antigen serves as analyte, and the following conditions are used: 10 mM MES buffer, 0.05% polyoxyethylenesorbitan monolaurate, and 150 mM NaCl at 37 degrees C. The invention also provides methods of inhibits cleavage of complement component C4, where the antibody does not inhibit cleavage of complement component C2. In some cases, the antibody inhibits a component of the classical complement pathway; in some cases, the classical complement pathway component is C1s. In a further aspect, it is possible to use the dissociation rate constant (kd) instead of KD above.

In one aspect, the present disclosure provides a method to modulate complement activation. In some embodiments the method inhibits complement activation, for example to reduce production of C4b2a. In some embodiments, the present disclosure provides a method to modulate complement activation in an individual having a complement-mediated disease or disorder, the method comprising administering to the individual an anti-C1s antibody of the present disclosure or a pharmaceutical composition of the present disclosure, wherein the pharmaceutical composition comprises an anti-C1s antibody of the present disclosure. In some embodiments such a method inhibits complement activation. In some embodiments, the individual is a mammal. In some embodiments, the individual is a human. Administering can be by any route known to those skilled in the art, including those disclosed herein. In some embodiments, administering is intravenous. In some embodiments, administering is intrathecal.

In certain embodiments, an anti-C1s antibody of the present invention binds to C1s from more than one species. In particular embodiments, the anti-C1s antibody binds to C1s from a human and non-human animal. In particular embodiments, the anti-C1s antibody binds to C1s from human, rat, and monkey (e.g. cynomolgus, rhesus macaque, marmoset, chimpanzee, and baboon).

In one aspect, the invention provides an anti-C1s antibody comprising at least one, two, three, four, five, or six HVRs selected from (a) HVR-H1 comprising the amino acid sequence of SEQ ID NO: 39; (b) HVR-H2 comprising the amino acid sequence of SEQ ID NO: 40; (c) HVR-H3 comprising the amino acid sequence of SEQ ID NO: 41; (d) HVR-L1 comprising the amino acid sequence of SEQ ID NO: 42 or 45; (e) HVR-L2 comprising the amino acid sequence of SEQ ID NO: 43; and (f) HVR-L3 comprising the amino acid sequence of SEQ ID NO: 44.

In one aspect, the invention provides an antibody comprising at least one, at least two, or all three VH HVR sequences selected from (a) HVR-H1 comprising the amino acid sequence of SEQ ID NO: 39; (b) HVR-H2 comprising the amino acid sequence of SEQ ID NO: 40; and (c) HVR-H3 comprising the amino acid sequence of SEQ ID NO: 41. In one embodiment, the antibody comprises HVR-H3 comprising the amino acid sequence of SEQ ID NO: 41. In another embodiment, the antibody comprises HVR-H3 comprising the amino acid sequence of SEQ ID NO: 41 and HVR-L3 comprising the amino acid sequence of SEQ ID NO: 44. In a further embodiment, the antibody comprises HVR-H3 comprising the amino acid sequence of SEQ ID NO: 41, HVR-L3 comprising the amino acid sequence of SEQ ID NO: 44, and HVR-H2 comprising the amino acid sequence of SEQ ID NO: 40. In a further embodiment, the antibody comprises (a) HVR-H1 comprising the amino acid sequence of SEQ ID NO: 39; (b) HVR-H2 comprising the amino acid sequence of SEQ ID NO: 40; and (c) HVR-H3 comprising the amino acid sequence of SEQ ID NO: 41.

In another aspect, the invention provides an antibody comprising at least one, at least two, or all three VL HVR sequences selected from (a) HVR-L1 comprising the amino acid sequence of SEQ ID NO: 42 or 45; (b) HVR-L2 comprising the amino acid sequence of SEQ ID NO: 43; and (c) HVR-L3 comprising the amino acid sequence of SEQ ID NO: 44. In one embodiment, the antibody comprises (a) HVR-L1 comprising the amino acid sequence of SEQ ID NO: 42 or 45; (b) HVR-L2 comprising the amino acid sequence of SEQ ID NO: 43; and (c) HVR-L3 comprising the amino acid sequence of SEQ ID NO: 44.

In another aspect, an antibody of the invention comprises (a) a VH domain comprising at least one, at least two, or all three VH HVR sequences selected from (i) HVR-H1 comprising the amino acid sequence of SEQ ID NO: 39, (ii) HVR-H2 comprising the amino acid sequence of SEQ ID NO: 40, and (iii) HVR-H3 comprising an amino acid sequence of SEQ ID NO: 41; and (b) a VL domain comprising at least one, at least two, or all three VL HVR sequences selected from (i) HVR-L1 comprising the amino acid sequence of SEQ ID NO: 42 or 45, (ii) HVR-L2 comprising the amino acid sequence of SEQ ID NO: 43, and (c) HVR-L3 comprising the amino acid sequence of SEQ ID NO: 44.

In another aspect, the invention provides an antibody comprising (a) HVR-H1 comprising the amino acid sequence of SEQ ID NO: 39; (b) HVR-H2 comprising the amino acid sequence of SEQ ID NO: 40; (c) HVR-H3 comprising the amino acid sequence of SEQ ID NO: 41; (d) HVR-L1 comprising the amino acid sequence of SEQ ID NO: 42 or 45; (e) HVR-L2 comprising the amino acid sequence of SEQ ID NO: 43; and (f) HVR-L3 comprising an amino acid sequence selected from SEQ ID NO: 44.

In some embodiments, anti-C1s antibody variants which are prepared by introducing amino acid modifications into an antibody comprising a VH sequence of SEQ ID No: 35 or 36 and a VL sequence of SEQ ID NO: 37 or 38 are provided.

In some embodiments, anti-C1s antibody variants which are prepared by introducing amino acid modifications into the antibody VH1/Vk1, VH1/Vk2, VH1/Vk3, VH2/Vk1, VH2/Vk2, VH2/Vk3, VH3/Vk1, VH3/Vk2, VH3/Vk3, VH4/Vk1, VH4/Vk2, or VH4/Vk3 disclosed in WO2014/071206 are provided.

In some embodiments, anti-C1s antibody of the present invention comprises a histidine at one or more of the following Kabat numbering system positions:
 Heavy chain: H26, H27, H28, H29, H30, H31, H32, H33, H34, H35, H50, H51, H52, H52a, H53, H54, H55, H57, H58, H59, H60, H61, H62, H63, H64, H65, H93, H94, H95, H96, H97, H98, H99, H100, H100a, H101, and H102; and
 Light chain: L24, L25, L26, L27, L27a, L28, L29, L30, L31, L32, L33, L50, L51, L52, L53, L54, L55, L56 L91, L92, L93, L94, L95, L95a, L96, and L97.

In some embodiments, anti-C1s antibody of the present invention comprises a histidine at one or more of the following Kabat numbering system positions:
 Heavy chain: H26, H27, H28, H29, H30, H32, H33, H34, H50, H51, H52a, H54, H57, H58, H59, H60, H61, H65, H93, H95, H99, H100, and H100a; and
 Light chain: L25, L28, L91, L92, L94, L95, L96, and L97.

In some embodiments, anti-C1s antibody of the present invention comprises at least one histidine substituted for one or more amino acid residues at positions selected from the following Kabat numbering system positions:
 Heavy chain: H26, H27, H28, H29, H30, H31, H32, H33, H34, H35, H50, H51, H52, H52a, H53, H54, H55, H57, H58, H59, H60, H61, H62, H63, H64, H65, H93, H94, H95, H96, H97, H98, H99, H100, H100a, H101, and H102; and
 Light chain: L24, L25, L26, L27, L27a, L28, L29, L30, L31, L32, L33, L50, L51, L52, L53, L54, L55, L56 L91, L92, L93, L94, L95, L95a, L96, and L97.

In some embodiments, any one or more amino acids of an anti-C1s antibody as provided above are substituted with histidine at the following Kabat numbering system positions:
 Heavy chain: H51, H65, and H99; and
 Light chain: L92, L94, L95 and L96.

In some embodiments, an isolated anti-C1s antibody of the present invention comprises one, two, three, four, or five histidines substituted for amino acid residues at the following Kabat numbering system positions:
 Heavy chain: H51, H65, and H99; and
 Light chain: L92, L94, L95 and L96.

In some embodiments, an isolated anti-C1s antibody of the present invention comprises at least one histidine which is a substituted residue at one or more of the following positions and a CDR or a FR amino acid position, by Kabat numbering system:

Heavy chain: H51, H65, and H99; and
Light chain: L92, L94, L95 and L96.

In some embodiments, an isolated anti-C1s antibody of the present invention comprises at least one histidine which is a substituted residue at the following positions by Kabat numbering system:
1) L92 and L94
2) L92 and L95
3) L94 and L95
4) L92, L94 and L95
5) H65 and L92
6) H65 and L94
7) H65 and L95
8) H65, L92 and L94
9) H65, L92 and L95
10) H65, L94 and L95
11) H65, L92, L94 and L95
12) H99 and L92
13) H99 and L94
14) H99 and L95
15) H99, L92 and L94
16) H99, L92 and L95
17) H99, L94 and L95
18) H99, L92, L94 and L95
19) H65 and H99
20) H65, H99 and L92
21) H65, H99 and L94
22) H65, H99 and L95
23) H65, H99, L92 and L94
24) H65, H99, L92 and L95
25) H65, H99, L94 and L95
26) H65, H99, L92, L94 and L95, or
27) H27, H99 and L95.

In any of the above embodiments, an anti-C1s antibody is humanized. In one embodiment, an anti-C1s antibody comprises HVRs as in any of the above embodiments, and further comprises an acceptor human framework, e.g. a human immunoglobulin framework or a human consensus framework. In another embodiment, an anti-C1s antibody comprises HVRs as in any of the above embodiments, and further comprises a VH or VL comprising an FR sequence. In a further embodiment, the anti-C1s antibody of the invention comprises the following heavy chain or light chain variable domain FR sequences: For the heavy chain variable domain, FR1 comprises the amino acid sequence of SEQ ID NO: 4 or 12, FR2 comprises the amino acid sequence of SEQ ID NO: 5, FR3 comprises the amino acid sequence of SEQ ID NO: 6, FR4 comprises the amino acid sequence of SEQ ID NO: 7. For the light chain variable domain, FR1 comprises the amino acid sequence of SEQ ID NO: 8, FR2 comprises the amino acid sequence of SEQ ID NO: 9, FR3 comprises the amino acid sequence of SEQ ID NO: 10, FR4 comprises the amino acid sequence of SEQ ID NO: 11.

In another aspect, an anti-C1s antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 19, 17, or 22. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C1s antibody comprising that sequence retains the ability to bind to C1s. In certain embodiments, a total of 1 to 10 amino acids have been substituted, inserted and/or deleted in SEQ ID NO: 19, 17, or 22. In certain embodiments, substitutions, insertions, or deletions occur in regions outside the HVRs (i.e., in the FRs). Optionally, the anti-C1s antibody comprises the VH sequence in SEQ ID NO: 19, 17, or 22, including post-translational modifications of that sequence. In a particular embodiment, the VH comprises one, two or three HVRs selected from: (a) HVR-H1 comprising the amino acid sequence of SEQ ID NO: 39, (b) HVR-H2 comprising the amino acid sequence of SEQ ID NO: 40, and (c) HVR-H3 comprising the amino acid sequence of SEQ ID NO: 41. Post-translational modifications include but are not limited to a modification of glutamine or glutamate in N-terminal of heavy chain or light chain to pyroglutamic acid by pyroglutamylation.

In another aspect, an anti-C1s antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 20, 18, or 21. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C1s antibody comprising that sequence retains the ability to bind to C1s. In certain embodiments, a total of 1 to 10 amino acids have been substituted, inserted and/or deleted in SEQ ID NO: 20, 18, or 21. In certain embodiments, the substitutions, insertions, or deletions occur in regions outside the HVRs (i.e., in the FRs). Optionally, the anti-C1s antibody comprises the VL sequence in SEQ ID NO: 20, 18, or 21, including post-translational modifications of that sequence. In a particular embodiment, the VL comprises one, two or three HVRs selected from (a) HVR-L1 comprising the amino acid sequence of SEQ ID NO: 42 or 45; (b) HVR-L2 comprising the amino acid sequence of SEQ ID NO: 43; and (c) HVR-L3 comprising the amino acid sequence of SEQ ID NO: 44. Post-translational modifications include but are not limited to a modification of glutamine or glutamate in N-terminal of heavy chain or light chain to pyroglutamic acid by pyroglutamylation.

In another aspect, an anti-C1s antibody is provided, wherein the antibody comprises a VH as in any of the embodiments provided above, and a VL as in any of the embodiments provided above. In one embodiment, the antibody comprises the VH and VL sequences in SEQ ID NO: 19 and SEQ ID NO: 20, respectively, including post-translational modifications of those sequences. Post-translational modifications include but are not limited to a modification of glutamine or glutamate in N-terminal of heavy chain or light chain to pyroglutamic acid by pyroglutamylation. In one embodiment, the antibody comprises the VH and VL sequences in SEQ ID NO: 17 and SEQ ID NO: 18, respectively, including post-translational modifications of those sequences. Post-translational modifications include but are not limited to a modification of glutamine or glutamate in N-terminal of heavy chain or light chain to pyroglutamic acid by pyroglutamylation. In one embodiment, the antibody comprises the VH and VL sequences in SEQ ID NO: 22 and SEQ ID NO: 20, respectively, including post-translational modifications of those sequences. Post-translational modifications include but are not limited to a modification of glutamine or glutamate in N-terminal of heavy chain or light chain to pyroglutamic acid by pyroglutamylation. In one embodiment, the antibody comprises the VH and VL sequences in SEQ ID NO: 19 and SEQ ID NO: 21, respectively, including post-translational modifications of those sequences. Post-translational modifications include but are not limited to a modification of glutamine or glutamate in N-terminal of heavy chain or light chain to pyroglutamic acid by pyroglutamylation. In one embodiment, the antibody comprises the VH and VL sequences in SEQ ID NO: 22 and SEQ ID NO: 21, respectively, including post-translational modifications of those sequences. Post-translational modifications include but are not limited to a modification of glutamine or glutamate in N-terminal of heavy chain or light chain to pyroglutamic acid by pyroglutamylation.

In a further aspect, the invention provides an antibody that binds to the same epitope as an anti-C1s antibody provided herein. For example, in certain embodiments, an antibody is provided that binds to the same epitope as an antibody selected from the group consisting of:
  (a) an antibody comprising the HVR-H1 sequence of SEQ ID NO: 23, the HVR-H2 sequence of SEQ ID NO: 24 the HVR-H3 sequence of SEQ ID NO: 25, the HVR-L1 sequence of SEQ ID NO: 26, the HVR-L2 sequence of SEQ ID NO: 27, and the HVR-L3 sequence of SEQ ID NO: 28,
  (b) an antibody comprising the HVR-H1 sequence of SEQ ID NO: 29, the HVR-H2 sequence of SEQ ID NO: 30, the HVR-H3 sequence of SEQ ID NO: 31, the HVR-L1 sequence of SEQ ID NO: 32, the HVR-L2 sequence of SEQ ID NO: 33, and the HVR-L3 sequence of SEQ ID NO: 34,
  (c) Human monoclonal anti-C1s antibody M241 (HycultBiotech, Catalog #: HM2109) or Human monoclonal anti-C1s antibody M81 (HycultBiotech, Catalog #: HM2108)
  (d) an antibody comprising the HVR-H1 sequence of SEQ ID NO: 56, the HVR-H2 sequence of SEQ ID NO: 57, the HVR-H3 sequence of SEQ ID NO: 58, the HVR-L1 sequence of SEQ ID NO: 71, the HVR-L2 sequence of SEQ ID NO: 72, and the HVR-L3 sequence of SEQ ID NO: 73,
  (e) an antibody comprising the HVR-H1 sequence of SEQ ID NO: 59, the HVR-H2 sequence of SEQ ID NO: 60, the HVR-H3 sequence of SEQ ID NO: 61, the HVR-L1 sequence of SEQ ID NO: 74, the HVR-L2 sequence of SEQ ID NO: 75, and the HVR-L3 sequence of SEQ ID NO: 76,
  (f) an antibody comprising the HVR-H1 sequence of SEQ ID NO: 62, the HVR-H2 sequence of SEQ ID NO: 63, the HVR-H3 sequence of SEQ ID NO: 64, the HVR-L1 sequence of SEQ ID NO: 77, the HVR-L2 sequence of SEQ ID NO: 78, and the HVR-L3 sequence of SEQ ID NO: 79,
  (g) an antibody comprising the HVR-H1 sequence of SEQ ID NO: 65, the HVR-H2 sequence of SEQ ID NO: 66, the HVR-H3 sequence of SEQ ID NO: 67, the HVR-L1 sequence of SEQ ID NO: 80, the HVR-L2 sequence of SEQ ID NO: 81, and the HVR-L3 sequence of SEQ ID NO: 82, and
  (h) an antibody comprising the HVR-H1 sequence of SEQ ID NO: 68, the HVR-H2 sequence of SEQ ID NO: 69, the HVR-H3 sequence of SEQ ID NO: 70, the HVR-L1 sequence of SEQ ID NO: 83, the HVR-L2 sequence of SEQ ID NO: 84, and the HVR-L3 sequence of SEQ ID NO: 85,
wherein the antibody binds to C1s with a higher affinity at neutral pH than at acidic pH as described in (i) or (ii) below:
  (i) when measured at a high calcium concentration at both neutral and acidic pH, the ratio of the KD value for C1s-binding activity at acidic pH to the KD value for C1s-binding activity at neutral pH (KD(acidic pH)/KD (neutral pH)) is 2 or more,
  (ii) when measured at a high calcium concentration at both neutral and acidic pH, the ratio of the koff value for C1s-binding activity at acidic pH to the koff value for C1s-binding activity at neutral pH (koff(acidic pH)/koff(neutral pH)) is 2 or more.

In some embodiments, an isolated anti-C1s antibody of the present invention competes for binding to C1s with an antibody selected from the group consisting of:
  (a) an antibody comprising the HVR-H1 sequence of SEQ ID NO: 56, the HVR-H2 sequence of SEQ ID NO: 57, the HVR-H3 sequence of SEQ ID NO: 58, the HVR-L1 sequence of SEQ ID NO: 71, the HVR-L2 sequence of SEQ ID NO: 72, and the HVR-L3 sequence of SEQ ID NO: 73,
  (b) an antibody comprising the HVR-H1 sequence of SEQ ID NO: 59, the HVR-H2 sequence of SEQ ID NO: 60, the HVR-H3 sequence of SEQ ID NO: 61, the HVR-L1 sequence of SEQ ID NO: 74, the HVR-L2 sequence of SEQ ID NO: 75, and the HVR-L3 sequence of SEQ ID NO: 76,
  (c) an antibody comprising the HVR-H1 sequence of SEQ ID NO: 62, the HVR-H2 sequence of SEQ ID NO: 63, the HVR-H3 sequence of SEQ ID NO: 64, the HVR-L1 sequence of SEQ ID NO: 77, the HVR-L2 sequence of SEQ ID NO: 78, and the HVR-L3 sequence of SEQ ID NO: 79,
  (d) an antibody comprising the HVR-H1 sequence of SEQ ID NO: 65, the HVR-H2 sequence of SEQ ID NO: 66, the HVR-H3 sequence of SEQ ID NO: 67, the HVR-L1 sequence of SEQ ID NO: 80, the HVR-L2 sequence of SEQ ID NO: 81, and the HVR-L3 sequence of SEQ ID NO: 82, and
  (e) an antibody comprising the HVR-H1 sequence of SEQ ID NO: 68, the HVR-H2 sequence of SEQ ID NO: 69, the HVR-H3 sequence of SEQ ID NO: 70, the HVR-L1 sequence of SEQ ID NO: 83, the HVR-L2 sequence of SEQ ID NO: 84, and the HVR-L3 sequence of SEQ ID NO: 85.

In a further aspect, the invention provides an antibody that binds to the same epitope as an anti-C1s antibody provided herein. For example, in certain embodiments, the invention provides an antibody that binds to the same epitope as an antibody selected from the group consisting of:
  IPN-M1, IPN-M2, IPN-M3, IPN-M8, IPN-M9, IPN-M10, IPN-M11, IPN-M13, IPN-M14, IPN-M15, IPN-M18, IPN-M23, IPN-M24, IPN-M27, IPN-M28, IPN-M29, and IPN-M33 disclosed in WO2014/066744.

In some embodiments, an isolated anti-C1s antibody of the present invention competes at neutral pH for binding to C1s with an antibody selected from the group consisting of:
  (a) an antibody comprising the HVR-H1 sequence of SEQ ID NO: 23, the HVR-H2 sequence of SEQ ID NO: 24, the HVR-H3 sequence of SEQ ID NO: 25, the HVR-L1 sequence of SEQ ID NO: 26, the HVR-L2 sequence of SEQ ID NO: 27, and the HVR-L3 sequence of SEQ ID NO: 28,
  (b) an antibody comprising the HVR-H1 sequence of SEQ ID NO: 29, the HVR-H2 sequence of SEQ ID NO: 30, the HVR-H3 sequence of SEQ ID NO: 31, the HVR-L1 sequence of SEQ ID NO: 32, the HVR-L2 sequence of SEQ ID NO: 33, and the HVR-L3 sequence of SEQ ID NO: 34, and
  (c) Human monoclonal anti-C1s antibody M241 (HycultBiotech, Catalog #: HM2109) or Human monoclonal anti-C1s antibody M81 (HycultBiotech, Catalog #: HM2108).

In some embodiments, an isolated anti-C1s antibody of the present invention competes at neutral pH for binding to C1s with an antibody selected from the group consisting of:

IPN-M1, IPN-M2, IPN-M3, IPN-M8, IPN-M9, IPN-M10, IPN-M11, IPN-M13, IPN-M14, IPN-M15, IPN-M18, IPN-M23, IPN-M24, IPN-M27, IPN-M28, IPN-M29, and IPN-M33 disclosed in WO2014/066744.

In one aspect, the present disclosure provides an isolated humanized monoclonal antibody with pH-dependent binding that specifically binds to an epitope within a region encompassing domains IV and V of complement component 1s (C1s). In some cases, the antibody inhibits binding of C1s to complement component 4 (C4). In some cases, the antibody does not inhibit protease activity of C1s. In some cases, the epitope bound by an isolated humanized monoclonal antibody of the present disclosure is a conformational epitope.

In one aspect, the present disclosure provides an isolated antibody with pH-dependent binding that specifically binds to an epitope within a complement C1s protein. In some embodiments, an isolated anti-C1s antibody of the present disclosure binds to an activated C1s protein. In some embodiments, an isolated anti-C1s antibody of the present disclosure binds to an inactive form of C1s. In other instances, an isolated anti-C1s antibody of the present disclosure binds to both an activated C1s protein and an inactive form of C1s.

In one aspect, the present disclosure provides an isolated humanized monoclonal antibody with pH-dependent binding that specifically binds to an epitope within a region encompassing domains IV and V of C1s. For example, the present disclosure provides an isolated humanized monoclonal antibody that specifically binds to an epitope within amino acids at positions 272-422 of the amino acid sequence set forth in SEQ ID NO: 1. In some cases, the isolated humanized monoclonal antibody specifically binds to an epitope within amino acids at positions 272-422 of the amino acid sequence set forth in SEQ ID NO: 1, and inhibits binding of C4 to C1s. The present disclosure also provides methods of treating a complement-mediated disease or disorder, the method comprising administering to an individual in need thereof an effective amount of an isolated humanized monoclonal antibody that specifically binds to an epitope within amino acids at positions 272-422 of the amino acid sequence set forth in SEQ ID NO: 1, and inhibits binding of C4 to C1s.

In one aspect, the present disclosure provides an isolated humanized monoclonal antibody with pH-dependent binding that specifically binds to an epitope comprising aspartic acid at position 357 of human C1s antigen.

In a further aspect of the invention, an anti-C1s antibody according to any of the above embodiments is a monoclonal antibody, including a chimeric, humanized or human antibody. In one embodiment, an anti-C1s antibody is an antibody fragment, e.g., a Fv, Fab, Fab', scFv, diabody, or F(ab')2 fragment. In another embodiment, the antibody is a full length antibody, e.g., an intact IgG1, IgG2, IgG3 or IgG4 antibody or other antibody class or isotype as defined herein.

In a further aspect, an anti-C1s antibody according to any of the above embodiments may incorporate any of the features, singly or in combination, as described in Sections 1-7 below:

1. Antibody Affinity

In certain embodiments, an antibody provided herein has a dissociation constant (Kd or KD) of 1 micro M or less, 100 nM or less, 10 nM or less, 1 nM or less, 0.1 nM or less, 0.01 nM or less, or 0.001 nM or less (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER (registered trademark) multi-well plates (Thermo Scientific) are coated overnight with 5 micro g/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23 degrees C.). In a non-adsorbent plate (Nunc #269620), 100 pM or 26 PM [125I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20 (registered trademark)) in PBS. When the plates have dried, 150 micro l/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE (registered trademark) surface plasmon resonance assay. For example, an assay using a BIACORE (registered trademark)-2000 or a BIACORE(registered trademark)-3000 (BIAcore, Inc., Piscataway, NJ) is performed at 25 degrees C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 micro g/ml (~0.2 micro M) before injection at a flow rate of 5 micro l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25 degrees C. at a flow rate of approximately 25 micro l/min. Association rates (kon) and dissociation rates (koff) are calculated using a simple one-to-one Langmuir binding model (BIACORE (registered trademark) Evaluation Software version 3.2) by simultaneously fitting the association and dissociation sensorgrams. The equilibrium dissociation constant (Kd) is calculated as the ratio koff/kon. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25 degrees C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

In some embodiments, the binding affinity of each histidine-substituted variant of the instant invention at pH 7.4 and pH 5.8 is determined at 37 degrees C. using Biacore T200 instrument (GE Healthcare). Recombinant Protein A/G (Pierce) can be immobilized onto all flow cells of a CM4 sensor chip using an amine coupling kit (GE Healthcare). Antibodies and analytes can be prepared in 7(+) buffer (20 mM ACES, 150 mM NaCl, 1.2 mM CaCl2, 0.05% Tween 20, 0.005% NaN3, pH 7.4), 5(+) buffer (20 mM ACES, 150 mM NaCl, 1.2 mM CaCl2, 0.05% Tween 20, 0.005% NaN3, pH 5.8), or 5(−) buffer (20 mM ACES, 150 mM NaCl, 3 micro M CaCl2, 0.05% Tween 20, 0.005% NaN3, pH 5.8). Each antibody can be captured onto the sensor surface by protein A/G. Antibody capture levels are aimed at 200 resonance unit (RU). Serum-derived human C1s (CompTech) or recombinant C1s prepared can be injected at, e.g., 50 or 200 nM, followed by dissociation. Sensor surface is regenerated each cycle with, e.g., 10 mM Glycine-HCl pH 1.5. Binding affinity may be determined by processing and fitting the data to 1:1 binding model using, e.g., Biacore T200 Evaluation software, version 2.0 (GE Healthcare).

Specific examples of steps of Biacore assay of the present invention are as follows.

The binding affinity of histidine-substituted variants at pH 7.4 and pH 5.8 are determined at 37 degrees C. using Biacore T200 instrument (GE Healthcare). Recombinant Protein A/G (Pierce) is immobilized onto all flow cells of a CM4 sensor chip using amine coupling kit (GE Healthcare). Antibodies and analytes are prepared in 7(+) buffer (20 mM ACES, 150 mM NaCl, 1.2 mM CaCl2, 0.05% Tween 20, 0.005% NaN3, pH 7.4) or 5(+) buffer (20 mM ACES, 150 mM NaCl, 1.2 mM CaCl2, 0.05% Tween 20, 0.005% NaN3, pH 5.8). Each antibody is captured onto the sensor surface by protein A/G. Antibody capture levels are aimed at 200 resonance unit (RU). Serum-derived human C1s is injected at 12.5, 50 nM for pH 7.4 or at 50, 200 nM at pH5.8, or 200 and 800 nM at pH5.8, followed by dissociation. Sensor surface is regenerated each cycle with 10 mM Glycine-HCl pH 1.5. Binding affinities are determined by processing and fitting the data to 1:1 binding model using Biacore T200 Evaluation software, version 2.0 (GE Healthcare). An additional dissociation phase at pH 5.8 is integrated immediately after the dissociation phase at pH 7.4. This dissociation rate in 5(+) buffer is determined by processing and fitting data using Scrubber 2.0 (BioLogic Software) curve fitting software.

Alternatively, the binding affinity of histidine-substituted variants at pH 7.4 and pH 5.8 are determined at 37 degrees C. using Biacore T200 instrument (GE Healthcare). Recombinant Protein A/G (Pierce) is immobilized onto all flow cells of a CM4 sensor chip using amine coupling kit (GE Healthcare). Antibodies and analytes are prepared in 7(+) buffer (20 mM ACES, 150 mM NaCl, 1.2 mM CaCl2, 0.05% Tween 20, 0.005% NaN3, pH 7.4) or 5(+) buffer (20 mM ACES, 150 mM NaCl, 1.2 mM CaCl2, 0.05% Tween 20, 0.005% NaN3, pH 5.8). Each antibody is captured onto the sensor surface by protein A/G. Antibody capture levels are aimed at 200 resonance unit (RU). Serum-derived human C1s is injected at 50 nM, followed by dissociation. Sensor surface is regenerated each cycle with 10 mM Glycine-HCl pH 1.5. Binding affinities are determined by processing and fitting the data to 1:1 binding model using Biacore T200 Evaluation software, version 2.0 (GE Healthcare). An additional dissociation phase at pH 5.8 is integrated immediately after the dissociation phase at pH 7.4. This dissociation rate in 5(+) buffer is determined by processing and fitting data using Scrubber 2.0 (BioLogic Software) curve fitting software.

In some embodiments, an additional dissociation phase at pH 5.8 is integrated immediately after the dissociation phase at pH 7.4, if necessary. This dissociation rate in 5(+) buffer can be determined by processing and fitting data using Scrubber 2.0 (BioLogic Software) curve fitting software.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB (registered trademark) technology; U.S. Pat. No. 7,041,870 describing K-M MOUSE (registered trademark) technology, and U.S. Patent Application Publication No. US 2007/0061900, describing VELOCIMOUSE (registered trademark) technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N J, 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N J, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for C1s and the other is for any other antigen. In certain embodiments, bispecific antibodies may bind to two different epitopes of C1s. Bispecific antibodies may also be used to localize cytotoxic agents to cells which express C1s. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting Fab" or "DAF" comprising an antigen binding site that binds to C1s as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Glu |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Typ (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be analyzed to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion of an enzyme (e.g. for ADEPT) or a polypeptide which increases the plasma half-life of the antibody to the N- or C-terminus of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about +/−3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks Fc gamma R binding (hence likely lacking ADCC activity), but retains FcRn binding ability. The primary cells for mediating ADCC, NK cells, express Fc gamma RIII only, whereas monocytes express Fc gamma RI, Fc gamma RII and Fc gamma RIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and Cyto-Tox 96 (registered trademark) non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with increased or decreased binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either increased or decreased) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and increased binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which increase binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-C1s antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0 cell). In one embodiment, a method of making an anti-C1s antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-C1s antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N J, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

Antibodies with pH-dependent characteristics may be obtained by using screening methods and/or mutagenesis methods e.g., as described in WO 2009/125825. The screening methods may comprise any process by which an antibody having pH-dependent binding characteristics is identified within a population of antibodies specific for a particular antigen. In certain embodiments, the screening methods may comprise measuring one or more binding parameters (e.g., KD or kd) of individual antibodies within an initial population of antibodies both at acidic pH and neutral pH. The binding parameters of the antibodies may be measured using, e.g., surface plasmon resonance, or any other analytic method that allows for the quantitative or qualitative assessment of the binding characteristics of an antibody to a particular antigen. In certain embodiments, the screening methods may comprise identifying an antibody that binds to an antigen with an acidic KD/neutral KD ratio of 2 or greater. Alternatively, the screening methods may comprise identifying an antibody that binds to an antigen with an acidic kd/neutral kd ratio of 2 or greater.

In another embodiment, the mutagenesis methods may comprise incorporating a deletion, substitution, or addition of an amino acid within the heavy and/or light chain of the antibody to enhance the pH-dependent binding of the antibody to an antigen. In certain embodiments, the mutagenesis may be carried out within one or more variable domains of the antibody, e.g., within one or more HVRs (e.g., CDRs). For example, the mutagenesis may comprise substituting an amino acid within one or more HVRs (e.g., CDRs) of the antibody with another amino acid. In certain embodiments, the mutagenesis may comprise substituting one or more amino acids in at least one HVR (e.g., CDR) of the antibody with histidine. In certain embodiments, "enhanced pH-dependent binding" means that the mutated version of the antibody exhibits a greater acidic KD/neutral KD ratio, or a greater acidic kd/neutral kd ratio, than the original "parent" (i.e., the less pH-dependent) version of the antibody prior to mutagenesis. In certain embodiments, the mutated version of the antibody has an acidic KD/neutral KD ratio of 2 or greater. Alternatively, the mutated version of the antibody has an acidic kd/neutral kd ratio of 2 or greater.

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl2, or RIN═C═NR, where R and R1 are different alkyl groups.

Animals (usually non-human mammals) are immunized against the antigen, immunogenic conjugates, or derivatives by combining, e.g., 100 micro g or 5 micro g of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature 256(5517):495-497 (1975). In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro.

The immunizing agent will typically include the antigenic protein or a fusion variant thereof. Generally, either peripheral blood lymphocytes (PBLs) are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press (1986), pp. 59-103).

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, California USA, and SP-2 cells (and derivatives thereof, e.g., X63-Ag8-653) available from the American Type Culture Collection, Manassas, Virginia USA. Human myeloma and mouse-human heteromyeloma cell lines also have been described for the production of human monoclonal antibodies (Kozbor et al. J. Immunol. 133(6):3001-3005 (1984); Brodeur et al., Monoclonal Antibody Production Techniques and Applications, Marcel Dekker, Inc., New York, pp. 51-63 (1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA). Such techniques and assays are known in the art. For example, binding affinity may be determined by the Scatchard analysis of Munson, Anal. Biochem. 107(1):220-239 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

C. Assays

Anti-C1s antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes for binding to C1s with any anti-C1s antibody described herein. In certain embodiments, when such a competing antibody is present in excess, it blocks (e.g., reduces) the binding of a reference antibody to C1s by at least 10%, 15%, 20%, 25%, 30%, 35%, 40%, 45%, 50%, 55%, 60%, 65%, 70%, 75% or more. In certain embodiments, such a competing antibody binds to the same epitope (e.g., a linear or a conformational epitope) that is bound by any anti-C1s antibody described herein. Detailed exemplary methods for mapping an epitope to which an antibody binds are provided in Morris (1996) "Epitope Mapping Protocols," in Methods in Molecular Biology vol. 66 (Humana Press, Totowa, NJ). In certain embodiments, such a competition assays can be conducted at neutral pH condition.

In an exemplary competition assay, immobilized C1s is incubated in a solution comprising a first labeled antibody that binds to C1s (e.g., one of those described herein) and a second unlabeled antibody that is being tested for its ability to compete with the first antibody for binding to C1s. The second antibody may be present in a hybridoma supernatant. As a control, immobilized C1s is incubated in a solution comprising the first labeled antibody but not the second unlabeled antibody. After incubation under conditions permissive for binding of the first antibody to C1s, excess unbound antibody is removed, and the amount of label associated with immobilized C1s is measured. If the amount of label associated with immobilized C1s is substantially reduced in the test sample relative to the control sample, then that indicates that the second antibody is competing with the first antibody for binding to C1s. See Harlow and Lane (1988) Antibodies: A Laboratory Manual ch. 14 (Cold Spring Harbor Laboratory, Cold Spring Harbor, NY).

In another aspect, an antibody that binds to the same epitope as an anti-C1s antibody provided herein or that competes for binding C1s with an anti-C1s antibody provided herein may be identified using sandwich assays. Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. See David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme. An antibody which simultaneously binds to C1s with an anti-C1s antibody provided herein can be determined to be an antibody that binds to a different epitope from the anti-C1s antibody. Therefore, an antibody which does not simultaneously bind to C1s with an anti-C1s antibody provided herein can be determined to be an antibody that binds to the same epitope as the anti-C1s antibody or that competes for binding C1s with the anti-C1s antibody.

2. Activity Assays

In one aspect, assays are provided for identifying anti-C1s antibodies thereof having biological activity. Biological activity may include blocking the activation of the classical pathway and generation of cleavage products resulting from the activation of the said pathway, C2a, C2b, C3a, C3b, C4a, C4b, C5a and C5b. Antibodies having such biological activity in vivo and/or in vitro are also provided.

In certain embodiments, an antibody of the invention is tested for such biological activity. In some embodiments, the antibody of the invention can be evaluated for its ability to inhibit complement-mediated hemolysis of chicken red blood cells (cRBC) that have been sensitized by antibodies directed against cRBC antigens. Using human serum as a source of complement proteins, the activity of the antibody of the invention can be determined by measuring the amount of haemoglobin released by a spectrophotometric method. In some embodiments, the antibody of the invention can be evaluated for its ability to inhibit activated C1s-mediated cleavage of purified C4 but not C2. The activity of the antibody is determined by measuring the amount of cleaved C4 or C2 by gel electrophoresis, or by the western blotting method. The cleaved C4 or C2 can be detected by its smaller molecular weight compared to its native uncleaved form.

3. Mouse PK Study for Assessing Antigen (C1s) Elimination

In certain embodiments, acceleration of elimination of antigen (e.g., human C1s (also referred to as hC1s)) by an antibody of the present invention can be assessed in vivo (e.g., in mouse) as follows.

Measurement of C1s Concentration in Mouse Plasma by High-Performance Liquid Chromatography-Electrospray Tandem Mass Spectrometry (LC/ESI-MS/MS)

The concentration of hC1s (or anti-C1s antibody) in mouse plasma can be measured by LC/ESI-MS/MS. The calibration standards are prepared by mixing and diluting hC1s (or anti-C1s antibody) in defined amounts in mouse plasma. The calibration standards and plasma samples are mixed with, e.g., Urea, dithiothreitol and lysozyme (chicken egg white) in ammonium bicarbonate, and incubated. Then, iodoacetamide is added and incubated in the dark. Next, trypsin in ammonium bicarbonate is added and incubated. Finally, trifluoroacetic acid is added to deactivate any residual trypsin. The samples are subjected to analysis by LC/ESI-MS/MS. A human C1s-specific peptide (e.g., LLEVPEGR) is monitored by the selected reaction monitoring (SRM). SRM transition may be [M+2H]2+ (m/z 456.8 to y6 ion (m/z 686.4) for human C1s. Calibration curve may be constructed by the weighted (1/x2) linear regression using the peak area plotted against the concentrations. The concentration in mouse plasma is calculated from the calibration curve.

Evaluation of Pharmacokinetics for Total hC1s after Administration of Anti-C1s Antibodies in Mice The in vivo pharmacokinetics of hC1s, hC1q, or an anti-C1s antibody may be assessed after administering the antigen alone or the antigen with an anti-C1s antibody to mice. A solution/mixture containing hC1s (etc.) is injected into mice intravenously. After dosing of antigen solution, an anti-C1s antibody solution is immediately administered to the same individual in the same way. The dose setting may be suitably designed to allow almost all hC1s to be in the bound form in circulation. Blood is collected over time, e.g., at 5, 30 minutes, 2, 7 hours, 3, 7, 14, 21 and 28 days after injection. The blood is centrifuged immediately to separate the plasma samples. Plasma concentrations of hC1s (etc.) are measured at each sampling points by LC/ESI-MS/MS. PK parameters of hC1s (etc.) is estimated by non-compartmental analysis. For example, an hC1s CL (clearance) ratio is calculated for the anti-C1s antibodies. If this ratio is higher, this means that the hC1s elimination can be more accelerated.

D. Immunoconjugates

The invention also provides immunoconjugates comprising an anti-C1s antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu. When the radioconjugate is used for detection, it may comprise a radioactive atom for scintigraphic studies, for example Tc-99m or $^{123}$I, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

E. Methods and Compositions for Diagnostics and Detection

In certain embodiments, any of the anti-C1s antibodies provided herein is useful for detecting the presence of C1s in a biological sample. The term "detecting" as used herein encompasses quantitative or qualitative detection. In certain embodiments, a biological sample comprises a cell or tissue, such as serum, whole blood, plasma, biopsy sample, tissue sample, cell suspension, saliva, sputum, oral fluid, cerebrospinal fluid, amniotic fluid, ascites fluid, milk, colostrum, mammary gland secretion, lymph, urine, sweat, lacrimal fluid, gastric fluid, synovial fluid, peritoneal fluid, ocular lens fluid or mucus.

In one embodiment, an anti-C1s antibody for use in a method of diagnosis or detection is provided. In a further aspect, a method of detecting the presence of C1s in a biological sample is provided. In certain embodiments, the method comprises contacting the biological sample with an anti-C1s antibody as described herein under conditions permissive for binding of the anti-C1s antibody to C1s, and detecting whether a complex is formed between the anti-C1s antibody and C1s. Such method may be an in vitro or in vivo method. In one embodiment, an anti-C1s antibody is used to select subjects eligible for therapy with an anti-C1s antibody, e.g. where C1s is a biomarker for selection of patients.

Exemplary disorders that may be diagnosed using an antibody of the invention include, but are not limited to, age-related macular degeneration, Alzheimer's disease, amyotrophic lateral sclerosis, anaphylaxis, argyrophilic grain dementia, arthritis (e.g., rheumatoid arthritis), asthma, atherosclerosis, atypical hemolytic uremic syndrome, autoimmune diseases, Barraquer-Simons syndrome, Behcet's disease, British type amyloid angiopathy, bullous pemphigoid, Buerger's disease, C1q nephropathy, cancer, catastrophic antiphospholipid syndrome, cerebral amyloid angiopathy, cold agglutinin disease, corticobasal degeneration, Creutzfeldt-Jakob disease, Crohn's disease, cryoglobulinemic vasculitis, dementia pugilistica, dementia with Lewy Bodies (DLB), diffuse neurofibrillary tangles with calcification, Discoid lupus erythematosus, Down's syndrome, focal segmental glomerulosclerosis, formal thought disorder, frontotemporal dementia (FTD), frontotemporal dementia with parkinsonism linked to chromosome 17, frontotemporal lobar degeneration, Gerstmann-Straussler-Scheinker disease, Guillain-Barre syndrome, Hallervorden-Spatz disease, hemolytic-uremic syndrome, hereditary angioedema, hypophosphastasis, idiopathic pneumonia syndrome, immune complex diseases, inclusion body myositis, infectious disease (e.g., disease caused by bacterial (e.g., *Neisseria meningitidis* or *Streptococcus*) viral (e.g., human immunodeficiency virus (HIV)), or other infectious agents), inflammatory disease, ischemia/reperfusion injury, mild cognitive impairment, immunothrombocytopenia purpura (ITP), molybdenum cofactor deficiency (MoCD) type A, membranoproliferative glomerulonephritis (MPGN) I, membranoproliferative glomerulonephritis (MPGN) II (dense deposit disease), membranous nephritis, multi-infarct dementia, lupus (e.g., systemic lupus erythematosus (SLE)), glomerulonephritis, Kawasaki disease, multifocal motor neuropathy, multiple sclerosis, multiple system atrophy, myasthenia gravis, myocardial infarction, myotonic dystrophy, neuromyelitis optica, Niemann-Pick disease type C, non-Guamanian motor neuron disease with neurofibrillary tangles, Parkinson's disease, Parkinson's disease with dementia, paroxysmal nocturnal hemoglobinuria, Pemphigus vulgaris, Pick's disease, postencephalitic parkinsonism, polymyositis, prion protein cerebral amyloid angiopathy, progressive subcortical gliosis, progressive supranuclear palsy, psoriasis, sepsis, Shiga-toxin *E coli* (STEC)-HuS, spinal muscular atrophy, stroke, subacute sclerosing panencephalitis, Tangle only dementia, transplant rejection, vasculitis (e.g., ANCA associated vasculitis), Wegner's granulomatosis, sickle cell disease, cryoglobulinemia, mixed cryoglobulinemia, essential mixed cryoglobulinemia, Type II mixed cryoglobulinemia, Type III mixed cryoglobulinemia, nephritis, drug-induced thrombocytopenia, lupus nephritis, bullous pemphigoid, Epidermolysis bullosa acquisita, delayed hemolytic transfusion reaction, hypocomplementemic urticarial vasculitis syndrome, pseudophakic bullous keratopathy, and platelet refractoriness.

In certain embodiments, labeled anti-C1s antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, those coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-C1s antibody as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutralactive hyaluronidase glycoproteins (sHASEGP), for example, human soluble PH-20 hyaluronidase glycoproteins, such as rHuPH20 (HYLENEX (registered trademark), Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide the formulation which is used for combination therapy, Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-C1s antibodies provided herein may be used in therapeutic methods.

In one aspect, an anti-C1s antibody for use as a medicament is provided. In further aspects, an anti-C1s antibody for use in treating a complement-mediated disease or disorder is provided. In certain embodiments, an anti-C1s antibody for use in a method of treatment is provided. In certain embodiments, the invention provides an anti-C1s antibody for use in a method of treating an individual having a complement-mediated disease or disorder comprising administering to the individual an effective amount of the anti-C1s antibody. In one such embodiment, the method further comprises administering to the individual an effective amount of at least one additional therapeutic agent.

In further embodiments, the invention provides an anti-C1s antibody for use in treating a complement-mediated disease or disorder. In further embodiments, anti-C1s antibodies of the present invention may be for use in enhancing the clearance of C1s from plasma. In further embodiments, anti-C1s antibodies of the present invention may be for use in enhancing the clearance of the complex of C1q, C1r and C1s from plasma. In some embodiments, anti-C1s antibodies of the present invention may be for use in inhibits cleavage of complement component C4, where the antibody does not inhibit cleavage of complement component C2. In some cases, the antibody inhibits a component of the classical complement pathway; in some cases, the classical complement pathway component is C1s. In certain embodiments, the invention provides an anti-C1s antibody for use in a method of treating a complement-mediated disease or disorder. In certain embodiments, the invention provides an anti-C1s antibody for use in a method of enhancing the clearance of C1s from plasma. In certain embodiments, the invention provides an anti-C1s antibody for use in a method of enhancing the clearance of the complex of C1q, C1r and C1s from plasma. In certain embodiments, the invention provides an anti-C1s antibody for use in a method of inhibiting cleavage of complement component C4, where the antibody does not inhibit cleavage of complement component C2. In certain embodiments, the invention provides an anti-C1s antibody for use in a method of inhibiting a component of the classical complement pathway; in some cases, the classical complement pathway component is C1s. An "individual" according to any of the above embodiments is preferably a human.

In one aspect, the present disclosure provides a method of modulating complement activation. In some embodiments the method inhibits complement activation, for example to reduce production of C4b2a. In some embodiments, the present disclosure provides a method of modulating complement activation in an individual having a complement-mediated disease or disorder, the method comprising administering to the individual an anti-C1s antibody of the present disclosure or a pharmaceutical composition of the present disclosure, wherein the pharmaceutical composition comprises an anti-C1s antibody of the present disclosure. In some embodiments such a method inhibits complement activation. In some embodiments, the individual is a mammal. In some embodiments, the individual is a human. Administration can be by any route known to those skilled in the art, including those disclosed herein. In some embodiments, administration is intravenous or subcutaneous. In some embodiments, administration is intrathecal.

A complement-mediated disease or disorder is a disorder characterized by an abnormal amount of complement C1s or an abnormal level of complement C1s proteolytic activity in a cell, a tissue, or a fluid of an individual.

In some cases, a complement-mediated disease or disorder is characterized by the presence in a cell, a tissue, or a fluid of an elevated (higher than normal) amount of C1s or of an elevated level of complement C1s activity. For example, in some cases, a complement-mediated disease or disorder is characterized by the presence in brain tissue and/or cerebrospinal fluid of an elevated amount and/or an elevated activity of C1s. A "higher than normal" amount of C1s in a cell, a tissue, or a fluid indicates that the amount of C1s in the cell, tissue or fluid is higher than a normal, control level, e.g., higher than a normal, control level for an individual or population of individuals of the same age group. A "higher than normal" level of C1s activity in a cell, a tissue, or a fluid indicates that the proteolytic cleavage effected by C1s in the cell, tissue or fluid is higher than a normal, control level, e.g., higher than a normal, control level for an individual or population of individuals of the same age group. In some cases, an individual having a complement-mediated disease or disorder exhibits one or more additional symptoms of such a disease or disorder.

In other cases, a complement-mediated disease or disorder is characterized by the presence in a cell, a tissue, or a fluid of a lower than normal amount of C1s or of a lower level of complement C1s activity. For example, in some cases, a complement-mediated disease or disorder is characterized by the presence in brain tissue and/or cerebrospinal fluid of a lower amount and/or a lower activity of C1s. A "lower than normal" amount of C1s in a cell, a tissue, or a fluid indicates that the amount of C1s in the cell, tissue or fluid is lower than a normal, control level, e.g., lower than a normal, control level for an individual or population of individuals of the same age group. A "lower than normal" level of C1s activity in a cell, a tissue, or a fluid indicates that the proteolytic cleavage effected by C1s in the cell, tissue or fluid is lower than a normal, control level, e.g., lower than a normal, control level for an individual or population of individuals of the same age group. In some cases, an individual having a complement-mediated disease or disorder exhibits one or more additional symptoms of such a disease or disorder.

A complement-mediated disease or disorder is a disease or disorder in which the amount or activity of complement C1s is such that it causes a disease or disorder in an individual. In some embodiments, the complement-mediated disease or disorder is selected from the group consisting of autoimmune disease, cancer, hematological disease, infectious disease, inflammatory disease, ischemia-reperfusion injury, neurodegenerative disease, neurodegenerative disorder, ocular disease, renal disease, transplant rejection, vascular disease, and vasculitis disease. In some embodiments, the complement-mediated disease or disorder is an autoimmune disease. In some embodiments, the complement-mediated disease or disorder is cancer. In some embodiments, the complement-mediated disease or disorder is an infectious disease. In some embodiments, the complement-mediated disease or disorder is an inflammatory disease. In some embodiments, the complement-mediated disease or disorder is a hematological disease. In some embodiments, the complement-mediated disease or disorder is an ischemia-reperfusion injury. In some embodiments, the complement-mediated disease or disorder is an ocular disease. In some embodiments, the complement-mediated disease or disorder is a renal disease. In some embodiments, the complement-mediated disease or disorder is transplant rejection. In some embodiments, the complement-mediated disease or disorder is antibody-mediated transplant rejection. In some embodiments, the complement-mediated disease or disorder is a vascular disease. In some embodiments, the complement-mediated disease or disorder is a vasculitis disorder. In some embodiments, the complement-mediated disease or disorder is a neurodegenerative disease or disorder. In some embodiments, the complement-mediated disease is a neurodegenerative disease. In some embodiments, the complement-mediated disorder is a neurodegenerative disorder. In some embodiments, the complement-mediated disease or disorder is a tauopathy.

Examples of a complement-mediated disease or disorder include, but are not limited to, age-related macular degeneration, Alzheimer's disease, amyotrophic lateral sclerosis, anaphylaxis, argyrophilic grain dementia, arthritis (e.g., rheumatoid arthritis), asthma, atherosclerosis, atypical hemolytic uremic syndrome, autoimmune diseases, Barraquer-Simons syndrome, Behcet's disease, British type amyloid angiopathy, bullous pemphigoid, Buerger's disease, C1q nephropathy, cancer, catastrophic antiphospholipid syndrome, cerebral amyloid angiopathy, cold agglutinin disease, corticobasal degeneration, Creutzfeldt-Jakob disease, Crohn's disease, cryoglobulinemic vasculitis, dementia pugilistica, dementia with Lewy Bodies (DLB), diffuse neurofibrillary tangles with calcification, Discoid lupus erythematosus, Down's syndrome, focal segmental glomerulosclerosis, formal thought disorder, frontotemporal dementia (FTD), frontotemporal dementia with parkinsonism linked to chromosome 17, frontotemporal lobar degeneration, Gerstmann-Straussler-Scheinker disease, Guillain-Barre syndrome, Hallervorden-Spatz disease, hemolytic-uremic syndrome, hereditary angioedema, hypophosphastasis, idiopathic pneumonia syndrome, immune complex diseases, inclusion body myositis, infectious disease (e.g., disease caused by bacterial (e.g., *Neisseria meningitidis* or *Streptococcus*) viral (e.g., human immunodeficiency virus (HIV)), or other infectious agents), inflammatory disease, ischemia/reperfusion injury, mild cognitive impairment, immuno-thrombocytopenia purpura (ITP), molybdenum cofactor deficiency (MoCD) type A, membranoproliferative glomerulonephritis (MPGN) I, membranoproliferative glomerulonephritis (MPGN) II (dense deposit disease), membranous nephritis, multi-infarct dementia, lupus (e.g., systemic lupus erythematosus (SLE)), glomerulonephritis, Kawasaki disease, multifocal motor neuropathy, multiple sclerosis, multiple system atrophy, myasthenia gravis, myocardial infarction, myotonic dystrophy, neuromyelitis optica, Niemann-Pick disease type C, non-Guamanian motor neuron disease with neurofibrillary tangles, Parkinson's disease, Parkinson's disease with dementia, paroxysmal nocturnal hemoglobinuria, Pemphigus vulgaris, Pick's disease, postencephalitic parkinsonism, polymyositis, prion protein cerebral amyloid angiopathy, progressive subcortical gliosis, progressive supranuclear palsy, psoriasis, sepsis, Shiga-toxin E coli (STEC)-HuS, spinal muscular atrophy, stroke, subacute sclerosing panencephalitis, Tangle only dementia, transplant rejection, vasculitis (e.g., ANCA associated vasculitis), Wegner's granulomatosis, sickle cell disease, cryoglobulinemia, mixed cryoglobulinemia, essential mixed cryoglobulinemia, Type II mixed cryoglobulinemia, Type III mixed cryoglobulinemia, nephritis, drug-induced thrombocytopenia, lupus nephritis, bullous pemphigoid, Epidermolysis bullosa acquisita, delayed hemolytic transfusion reaction, hypocomplementemic urticarial vasculitis syndrome, pseudophakic bullous keratopathy, and platelet refractoriness.

Alzheimer's disease and certain forms of Frontotemporal dementia (Pick's disease, sporadic Frontotemporal dementia and Frontotemporal dementia with Parkinsonism linked to chromosome 17) are the most common forms of tauopathy. In accordance with this, the present invention relates to any method as described above, wherein the tauopathy is Alzheimer's, Pick's disease, sporadic Frontotemporal dementia and Frontotemporal dementia with Parkinsonism linked to chromosome 17. Other tauopathies include, but are not limited to, Progressive supranuclear palsy (PSP), Corticobasal degeneration (CBD) and Subacute sclerosing panencephalitis.

A neurodegenerative tauopathy includes Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Straussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, Tangle only dementia, multi-infarct dementia, ischemic stroke, chronic traumatic encephalopathy (CTE), traumatic brain injury (TBI), and stroke.

The present disclosure also provides methods of treating a synucleinopathy, e.g., Parkinson's disease (PD); dementia with Lewy Bodies (DLB); multiple system atrophy (MSA); etc. For example, PD with dementia (PDD) can be treated with a method of the present disclosure.

In some embodiments, the complement-mediated disease or disorder comprises Alzheimer's disease. In some embodiments, the complement-mediated disease or disorder comprises Parkinson's disease. In some embodiments, the complement-mediated disease or disorder comprises transplant rejection. In some embodiments, the complement-mediated disease or disorder is antibody-mediated transplant rejection.

In some embodiments, an anti-C1s antibody of the present disclosure prevents or delays the onset of at least one symptom of a complement-mediated disease or disorder in an individual. In some embodiment, an anti-C1s antibody of the present disclosure reduces or eliminates at least one symptom of a complement-mediated disease or disorder in an individual. Examples of symptoms include, but are not limited to, symptoms associated with autoimmune disease, cancer, hematological disease, infectious disease, inflammatory disease, ischemia-reperfusion injury, neurodegenerative disease, neurodegenerative disorder, renal disease, transplant rejection, ocular disease, vascular disease, or a vasculitis disorder. The symptom can be a neurological symptom, for example, impaired cognitive function, memory impairment, loss of motor function, etc. The symptom can also be the activity of C1s protein in a cell, tissue, or fluid of an individual. The symptom can also be the extent of complement activation in a cell, tissue, or fluid of an individual.

In some embodiments, administering an anti-C1s antibody of the present disclosure to an individual modulates complement activation in a cell, tissue, or fluid of an individual. In some embodiments, administration of an anti-C1s antibody of the present disclosure to an individual inhibits complement activation in a cell, tissue, or fluid of an individual. For example, in some embodiments, an anti-C1s antibody of the present disclosure, when administered in one or more doses as monotherapy or in combination therapy to an individual having a complement-mediated disease or disorder, inhibits complement activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to complement activation in the individual before treatment with the anti-C1s antibody.

In some embodiments, an anti-C1s antibody of the present disclosure reduces C3 deposition onto red blood cells; for example, in some embodiments, an anti-C1s antibody of the present disclosure reduces deposition of C3b, iC3b, etc., onto RBCs. In some embodiments, an anti-C1s antibody of the present disclosure inhibits complement-mediated red blood cell lysis.

In some embodiments, an anti-C1s antibody of the present disclosure reduces C3 deposition onto platelets; for example, in some embodiments, an anti-C1s antibody of the present disclosure reduces deposition of C3b, iC3b, etc., onto platelets.

In some embodiments, administering an anti-C1s antibody of the present disclosure results in an outcome selected from the group consisting of: (a) a reduction in complement activation; (b) an improvement in cognitive function; (c) a reduction in neuron loss; (d) a reduction in phospho-Tau levels in neurons; (e) a reduction in glial cell activation; (f) a reduction in lymphocyte infiltration; (g) a reduction in macrophage infiltration; (h) a reduction in antibody deposition, (i) a reduction in glial cell loss; (j) a reduction in oligodendrocyte loss; (k) a reduction in dendritic cell infiltration; (l) a reduction in neutrophil infiltration; (m) a reduction in red blood cell lysis; (n) a reduction in red blood cell phagocytosis; (o) a reduction in platelet phagocytosis; (p) a reduction in platelet lysis; (q) an improvement in transplant graft survival; (r) a reduction in macrophage mediated phagocytosis; (s) an improvement in vision; (t) an improvement in motor control; (u) an improvement in thrombus formation; (v) an improvement in clotting; (w) an improvement in kidney function; (x) a reduction in antibody mediated complement activation; (y) a reduction in autoantibody mediated complement activation; (z) an improvement in anemia; (aa) reduction of demyelination; (ab) reduction of eosinophilia; (ac) a reduction of C3 deposition on red blood cells (e.g., a reduction of deposition of C3b, iC3b, etc., onto RBCs); and (ad) a reduction in C3 deposition on platelets (e.g., a reduction of deposition of C3b, iC3b, etc., onto platelets); and (ae) a reduction of anaphylatoxin toxin production; (af) a reduction in autoantibody mediated blister formation; (ag) a reduction in autoantibody induced pruritis; (ah) a reduction in autoantibody induced erythematosus; (ai) a reduction in autoantibody mediated skin erosion; (aj) a reduction in red blood cell destruction due to transfusion reactions; (ak) a reduction in red blood cell lysis due to alloantibodies; (al) a reduction in hemolysis due to transfusion reactions; (am) a reduction in allo-antibody mediated platelet lysis; (an) a reduction in platelet lysis due to transfusion reactions; (ao) a reduction in mast cell activation; (ap) a reduction in mast cell histamine release; (aq) a reduction in vascular permeability; (ar) a reduction in edema; (as) a reduction in complement deposition on transplant graft endothelium; (at) a reduction of anaphylatoxin generation in transplant graft endothelium; (au) a reduction in the separation of the dermal-epidermal junction; (av) a reduction in the generation of anaphylatoxins in the dermal-epidermal junction; (aw) a reduction in alloantibody mediated complement activation in transplant graft endothelium; (ax) a reduction in antibody mediated loss of the neuromuscular junction; (ay) a reduction in complement activation at the neuromuscular junction; (az) a reduction in anaphylatoxin generation at the neuromuscular junction; (ba) a reduction in complement deposition at the neuromuscular junction; (bb) a reduction in paralysis; (bc) a reduction in numbness; (bd) increased bladder control; (be) increased bowel control; (bf) a reduction in mortality associated with autoantibodies; and (bg) a reduction in morbidity associated with autoantibodies.

In some embodiments, an anti-C1s antibody of the present disclosure, when administered in one or more doses as monotherapy or in combination therapy to an individual having a complement-mediated disease or disorder, is effect to achieve a reduction of at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: (a) complement activation; (b) decline in cognitive function; (c) neuron loss; (d) phospho-Tau levels in neurons; (e) glial cell activation; (f) lymphocyte infiltration; (g) macrophage infiltration; (h) antibody deposition, (i) glial cell loss; (j) oligodendrocyte loss; (k) dendritic cell infiltration; (l) neutrophil infiltration; (m) red blood cell lysis; (n) red blood cell phagocytosis; (o) platelet phagocytosis; (p) platelet lysis; (q) transplant graft rejection; (r) macrophage mediated phagocytosis; (s) vision loss; (t) antibody mediated complement activation; (u) autoantibody mediated complement activation; (v) demyelination; (w) eosinophilia; compared to the level or degree of the outcome in the individual before treatment with the anti-C1s antibody.

In some embodiments, an anti-C1s antibody of the present disclosure, when administered in one or more doses as monotherapy or in combination therapy to an individual having a complement-mediated disease or disorder, is effect to achieve an improvement of at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: a) cognitive function; b) transplant graft survival; c) vision; d) motor control; e) thrombus formation; f) clotting; g) kidney function; and h) hematocrit (red blood cell count), compared to the level or degree of the outcome in the individual before treatment with the anti-C1s antibody.

In some embodiments, administering an anti-C1s antibody of the present disclosure to an individual reduces complement activation in the individual. For example, in some embodiments, an anti-C1s antibody of the present disclosure, when administered in one or more doses as monotherapy or in combination therapy to an individual having a complement-mediated disease or disorder, reduces complement activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to complement activation in the individual before treatment with the anti-C1s antibody.

In some embodiments, administering an anti-C1s antibody of the present disclosure improves cognitive function in the individual. For example, in some embodiments, an anti-C1s antibody of the present disclosure, when administered in one or more doses as monotherapy or in combination therapy to an individual having a complement-mediated disease or disorder, improves cognitive function in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the cognitive function in the individual before treatment with the anti-C1s antibody.

In some embodiments, administering an anti-C1s antibody of the present disclosure reduces the rate of decline in cognitive function in the individual. For example, in some embodiments, an anti-C1s antibody of the present disclosure, when administered in one or more doses as monotherapy or in combination therapy to an individual having a complement-mediated disease or disorder, reduces the rate of decline of cognitive function in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the rate of decline in cognitive function in the individual before treatment with the anti-C1s antibody.

In some embodiments, administering an anti-C1s antibody of the present disclosure to an individual reduces neuron loss in the individual. For example, in some embodiments, an anti-C1s antibody of the present disclosure, when administered in one or more doses as monotherapy or in combination therapy to an individual having a complement-mediated disease or disorder, reduces neuron loss in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to neuron loss in the individual before treatment with the anti-C1s antibody.

In some embodiments, administering an anti-C1s antibody of the present disclosure to an individual reduces phospho-Tau levels in the individual. For example, in some embodiments, an anti-C1s antibody of the present disclosure, when administered in one or more doses as monotherapy or in combination therapy to an individual having a complement-mediated disease or disorder, reduces phospho-Tau in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the phospho-Tau level in the individual before treatment with the anti-C1s antibody.

In some embodiments, administering an anti-C1s antibody of the present disclosure to an individual reduces glial cell activation in the individual. For example, in some embodiments, an anti-C1s antibody of the present disclosure, when administered in one or more doses as monotherapy or in combination therapy to an individual having a complement-mediated disease or disorder, reduces glial activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to glial cell activation in the individual before treatment with the anti-C1s antibody. In some embodiments, the glial cells are astrocytes or microglia.

In some embodiments, administering an anti-C1s antibody of the present disclosure to an individual reduces lymphocyte infiltration in the individual. For example, in some embodiments, an anti-C1s antibody of the present disclosure, when administered in one or more doses as monotherapy or in combination therapy to an individual having a complement-mediated disease or disorder, reduces lymphocyte infiltration in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to lymphocyte infiltration in the individual before treatment with the anti-C1s antibody.

In some embodiments, administering an anti-C1s antibody of the present disclosure to an individual reduces macrophage infiltration in the individual. For example, in some embodiments, an anti-C1s antibody of the present disclosure, when administered in one or more doses as monotherapy or in combination therapy to an individual having a complement-mediated disease or disorder, reduces macrophage infiltration in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to macrophage infiltration in the individual before treatment with the anti-C1s antibody.

In some embodiments, administering an anti-C1s antibody of the present disclosure to an individual reduces antibody deposition in the individual. For example, in some embodiments, an anti-C1s antibody of the present disclosure, when administered in one or more doses as monotherapy or in combination therapy to an individual having a complement-mediated disease or disorder, reduces antibody deposition in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to antibody deposition in the individual before treatment with the anti-C1s antibody.

In some embodiments, administering an anti-C1s antibody of the present disclosure to an individual reduces anaphylatoxin (e.g., C3a, C4a, C5a) production in an individual. For example, in some embodiments, an anti-C1s antibody of the present disclosure, when administered in one or more doses as monotherapy or in combination therapy to an individual having a complement-mediated disease or disorder, reduces anaphylatoxin production in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the level of anaphylatoxin production in the individual before treatment with the anti-C1s antibody.

In some embodiments, the present disclosure provides for use of an anti-C1s antibody of the present disclosure or a pharmaceutical composition comprising an anti-C1s antibody of the present disclosure and a pharmaceutically acceptable excipient to treat an individual having a complement-mediated disease or disorder. In some embodiments, the present disclosure provides for use of an anti-C1s antibody of the present disclosure to treat an individual having a complement-mediated disease or disorder. In some embodiments, the present disclosure provides for use of a pharmaceutical composition comprising an anti-C1s antibody of the present disclosure and a pharmaceutically acceptable excipient to treat an individual having a complement-mediated disease or disorder.

In some embodiments, the present disclosure provides for use of an anti-C1s antibody of the present disclosure in the manufacture of a medicament for the treatment of an individual having a complement-mediated disease or disorder.

In some embodiments, the present disclosure provides for use of an anti-C1s antibody of the present disclosure or a pharmaceutical composition comprising an anti-C1s antibody of the present disclosure and a pharmaceutically acceptable excipient to inhibit complement activation. In some embodiments, the present disclosure provides for use of an anti-C1s antibody of the present disclosure or a pharmaceutical composition comprising an anti-C1s antibody of the present disclosure and a pharmaceutically acceptable excipient to inhibit complement activation in an individual having a complement-mediated disease or disorder. In some embodiments, the present disclosure provides for use of an anti-C1s antibody of the present disclosure to inhibit complement activation in an individual having a complement-mediated disease or disorder. In some embodiments, the present disclosure provides for use of a pharmaceutical composition comprising an anti-C1s antibody of the present disclosure and a pharmaceutically acceptable excipient to inhibit complement activation in an individual having a complement-mediated disease or disorder.

In some embodiments, the present disclosure provides for use of an anti-C1s antibody of the present disclosure in the manufacture of a medicament for modulating complement activation. In some embodiments, the medicament inhibits complement activation. In some embodiments, the medicament inhibits complement activation in an individual having a complement-mediated disease or disorder.

In some embodiments, the present disclosure provides for an anti-C1s antibody of the present disclosure or a pharmaceutical composition comprising an anti-C1s antibody of the present disclosure and a pharmaceutically acceptable excipient for use in medical therapy. In some embodiments, the present disclosure provides for an anti-C1s antibody of the present disclosure for use in medical therapy. In some embodiments, the present disclosure provides for a pharmaceutical composition comprising an anti-C1s antibody of the present disclosure and a pharmaceutically acceptable excipient for use in medical therapy.

In some embodiments, the present disclosure provides for an anti-C1s antibody of the present disclosure or a pharmaceutical composition comprising an anti-C1s antibody of the present disclosure and a pharmaceutically acceptable excipient for treating an individual having a complement-mediated disease or disorder. In some embodiments, the present disclosure provides for an anti-C1s antibody of the present disclosure for treating an individual having a complement-mediated disease or disorder. In some embodiments, the present disclosure provides for a pharmaceutical composition comprising an anti-C1s antibody of the present disclosure and a pharmaceutically acceptable excipient for treating an individual having a complement-mediated disease or disorder.

In some embodiments, the present disclosure provides for an anti-C1s antibody of the present disclosure or a pharmaceutical composition comprising an anti-C1s antibody of the present disclosure and a pharmaceutically acceptable excipient for modulating complement activation. In some embodiments, the present disclosure provides for an anti-C1s antibody of the present disclosure for modulating complement activation. In some embodiments, the present disclosure provides for a pharmaceutical composition comprising an anti-C1s antibody of the present disclosure and a pharmaceutically acceptable excipient for modulating complement activation. In some embodiments, the anti-C1s antibody inhibits complement activation.

In a further aspect, the invention provides for the use of an anti-C1s antibody in the manufacture or preparation of a medicament. In one embodiment, the medicament is for treatment of a complement-mediated disease or disorder. In a further embodiment, the medicament is for use in a method of treating a complement-mediated disease or disorder comprising administering to an individual having a complement-mediated disease or disorder an effective amount of the medicament. In one such embodiment, the method further comprises administering to the individual an effective amount of at least one additional therapeutic agent, e.g., as described below. In a further embodiment, the medicament is for use in enhancing the clearance of (or removing) C1s from plasma. In a further embodiment, the medicament is for use in enhancing the clearance of (or removing) the complex of C1q, C1r and C1s from plasma. In a further embodiment, the medicament is for use in inhibiting cleavage of complement component C4, where the antibody does not inhibit cleavage of complement component C2. In a further embodiment, the medicament is for use in inhibiting a component of the classical complement pathway; in some cases, the classical complement pathway component is C1s In a further embodiment, the medicament is for use in a method of treating in an individual having a complement-mediated disease or disorder comprising administering to the individual an amount effective of the medicament. An "individual" according to any of the above embodiments may be a human.

In a further aspect, the invention provides a method for treating a complement-mediated disease or disorder. In one embodiment, the method comprises administering to an individual having such a complement-mediated disease or disorder an effective amount of an anti-C1s antibody. In one such embodiment, the method further comprises administering to the individual an effective amount of at least one additional therapeutic agent, as described below. An "individual" according to any of the above embodiments may be a human.

In a further aspect, the invention provides a method for enhancing the clearance of (or removing) C1s from plasma in an individual. In a further aspect, the invention provides a method for enhancing the clearance of (or removing) the complex of C1q, C1r and C1s from plasma in an individual. In some embodiments, anti-C1s antibodies of the present invention provide a method for inhibiting cleavage of complement component C4, where the antibody does not inhibit cleavage of complement component C2 in an individual. In some cases, the invention provides a method for inhibiting a component of the classical complement pathway in an individual; in some cases, the classical complement pathway component is C1s. In one embodiment, an "individual" is a human.

In a further aspect, the invention provides pharmaceutical formulations comprising any of the anti-C1s antibodies provided herein, e.g., for use in any of the above therapeutic methods. In one embodiment, a pharmaceutical formulation comprises any of the anti-C1s antibodies provided herein and a pharmaceutically acceptable carrier. In another embodiment, a pharmaceutical formulation comprises any of the anti-C1s antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-C1s antibody and administration of an additional therapeutic agent occur within about one month, or within about one, two or three weeks, or within about one, two, three, four, five, or six days, of each other. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 micro g/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 micro g/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-C1s antibody.

H. Articles of Manufacture

In another aspect of the invention, an article of manufacture containing materials useful for the treatment, prevention and/or diagnosis of the disorders described above is provided. The article of manufacture comprises a container and a label on or a package insert associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active ingredient in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-C1s antibody.

III. EXAMPLES

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 1: Expression and Purification of Human C1s

Recombinant human C1s (SEQ ID NO: 1) with a Flag-tag on the C-terminus (hC1s-Flag) was expressed transiently using the FreeStyle293-F cell line (Thermo Fisher, Carlsbad, CA, USA). Conditioned media expressing human recombinant hC1s-Flag was applied to a column packed with anti-Flag M2 affinity resin (Sigma) and eluted with a Flag peptide (Sigma). Fractions containing hC1s-Flag were collected and subsequently subjected to a Superdex 200 gel filtration column (GE healthcare Uppsala, Sweden). Fractions containing hC1s-Flag were then pooled, concentrated, and stored at −80 degrees Celsius (C).

Recombinant C1s (SEQ ID NO: 1) with carboxyl terminal 8× Histidine tag (hC1s-His) was expressed transiently using the FreeStyle293-F cell line (Thermo Fisher, Carlsbad, CA, USA). Conditioned media containing hC1s-His was applied to a HisTrap excel column (GE healthcare, Uppsala, Sweden) and eluted with imidazole. Fractions containing hC1s-His were pooled and applied to a Superdex 200 gel filtration column (GE healthcare, Uppsala, Sweden). Fractions containing hC1s-His were pooled, concentrated, and stored at −80 degrees C.

Example 2: Preparation of Anti-C1s Antibody

The polynucleotides of the heavy and light chain variable regions of the anti-C1s antibody, IPN009VH2 (SEQ ID NO: 13) and IPN009VK3 (SEQ ID NO: 14) (as described in WO2016164358) were synthesized by GenScript Inc. The heavy and light chain variable regions were cloned into expression vectors containing the heavy chain constant region SG4GK (SEQ ID NO: 15) and the light chain constant region SK1 (SEQ ID NO: 16), respectively. Anti-C1s antibody C1_IPN009VH2-SG4GK/IPN009VK3-SK1 (IPN009VH2/IPN009VK3) was expressed transiently using FreeStyle FS293-F cells and 293fectin (Life technologies), according to the manufacturer's instructions. Recombinant antibodies were purified with protein A (GE Healthcare) and eluted in D-PBS, Tris Buffered Saline (TBS), or His buffer (20 mM Histidine, 150 mM NaCl, pH6.0). Size exclusion chromatography was further conducted to remove high molecular weight and/or low molecular weight components, if necessary.

Histidine scanning was conducted for CDRs and certain positions in the FRs of IPN009VH2/IPN009VK3. The positions of the mutations in the variants are shown in Table 2 (upper part, fourth and sixth columns). The same applies to Tables 3-1 to 6. Each amino acid was individually mutated to histidine using In-Fusion HD Cloning Kit (Clontech Inc. or Takara Bio Company) according to the manufacturer's instructions. All variants were transiently expressed and purified by the method described above. The binding affinity of each histidine-substituted variant at pH 7.4 and pH 5.8 was determined at 37 degrees C. using Biacore T200 instrument (GE Healthcare). Recombinant Protein A/G (Pierce) was immobilized onto all flow cells of a CM4 sensor chip using an amine coupling kit (GE Healthcare). Antibodies and analytes were prepared in 7(+) buffer (20 mM ACES, 150 mM NaCl, 1.2 mM CaCl2, 0.05% Tween 20, 0,005% NaN3, pH 7.4), 5(+) buffer (20 mM ACES, 150 mM NaCl, 1.2 mM CaCl2, 0.05% Tween 20, 0.005% NaN3, pH 5.8), or 5(−) buffer (20 mM ACES, 150 mM NaCl, 3 micro M CaCl2, 0.05% Tween 20, 0.005% NaN3, pH 5.8). Each antibody was captured onto the sensor surface by protein A/G. Antibody capture levels were aimed at 200 resonance unit (RU). Serum-derived human C1s (CompTech) or recombinant C1s prepared in EXAMPLE 1 was injected at 50 nM, followed by dissociation. The sensor surface was regenerated in each cycle with 10 mM Glycine-HCl, pH 1.5. Binding affinity was determined by processing and fitting the data to 1:1 binding model using Biacore T200 Evaluation software, version 2.0 (GE Healthcare). Several of the single-histidine substitutions showed larger KD in 5(+) buffer ("KD 5.8+") and/or KD in 5(−) buffer ("KD 5.8−") compared to the KD in 7(+) buffer ("KD 7.4+"). The ratio of KD 5.8+ to KD 7.4+("KD 5+/7+") and that of KD 5.8− to KD 7.4+("KD 5−/7+") were calculated. When the KD 5+/7+ or KD 5−/7+ of a variant is larger than that of the parent antibody IPN009VH2-SG4GK/IPN009VK3-SK1, that variant is considered to be "pH"- or "pH and Ca"-dependent, respectively. When binding response in 5(+) buffer and/or in 5(−) buffer of a variant is much lower than that of IPN009VH2/IPN009VK3, that variant is also considered as "pH"- and/or "pH and Ca"-dependent. Therefore, such mutations are effective to generate "pH"- and/or "pH and Ca"-dependent antibody. The results of the Biacore assay are shown in Table 2. When the binding response is much lower than that of IPN009VH2/IPN009VK3, "low" is indicated in the table. To further enhance "pH" and/or "pH and Ca" dependency, a combination of histidine mutations was conducted. Antibodies with combinations of histidine mutations were evaluated using Biacore by the method described above. The results of the Biacore assay are shown in Tables 3-1 and 3-2. Many variants showed much better "pH" and "pH and Ca" dependency compared with IPN009VH2/IPN009VK3.

TABLE 2

| Name of antibody | Abbregation | Name of VH | Mutation(s) in VH from IPN009VH2 | Name of VL | Mutation(s) in VL from IPN009VK3 | Kon 7.4+ | koff 7.4+ | KD 7.4+ | Binding response 7.4+ |
|---|---|---|---|---|---|---|---|---|---|
| C1_IPN009VH2-SG4GK/IPN009VK3-SK1 | IPN009VH2/IPN009VK3 | IPN009VH2 | — | IPN009VK3 | — | 3.62E+05 | 2.98E−04 | 8.24E−10 | |
| C1_IPN92H0026-SG4GK/IPN009VK3-SK1 | IPN92H0026/IPN009VK3 | IPN92H0026 | G65H | IPN009VK3 | — | 4.30E+05 | 2.36E−04 | 5.49E−10 | |
| C1_IPN92H0033-SG4GK/IPN009VK3-SK1 | IPN92H0033/IPN009VK3 | IPN92H0033 | Y99H | IPN009VK3 | — | 3.28E+05 | 2.60E−04 | 7.90E−10 | |
| C1_IPN009VH2-SG4GK/IPN93L0021-SK1 | IPN009VH2/IPN93L0021 | IPN009VH2 | — | IPN93L0021 | Y92H | 3.35E+05 | 8.98E−04 | 2.68E−09 | |
| C1_IPN009VH2-SG4GK/IPN93L0023-SK1 | IPN009VH2/IPN93L0023 | IPN009VH2 | — | IPN93L0023 | L94H | 3.32E+05 | 7.25E−04 | 2.18E−09 | |
| C1_IPN009VH2-SG4GK/IPN93L0024-SK1 | IPN009VH2/IPN93L0024 | IPN009VH2 | — | IPN93L0024 | P95H | 2.33E+05 | 5.74E−04 | 2.46E−09 | |

| Name of antibody | Kon 5.8+ | koff 5.8+ | KD 5.8+ | Binding response 5.8+ | Kon 5.8− | koff 5.8− | KD 5.8− | Binding response 5.8− | KD 5+/7+ | KD 5−/7+ |
|---|---|---|---|---|---|---|---|---|---|---|
| C1_IPN009VH2-SG4GK/IPN009VK3-SK1 | 6.62E+05 | 1.08E−04 | 1.64E−10 | | 6.06E+05 | 2.04E−03 | 3.37E−09 | | 0.2 | 4.1 |
| C1_IPN92H0026-SG4GK/IPN009VK3-SK1 | 7.29E+05 | 1.62E−04 | 2.22E−10 | | 6.65E+05 | 1.71E−03 | 2.58E−09 | | 0.4 | 4.7 |
| C1_IPN92H0033-SG4GK/IPN009VK3-SK1 | 7.22E+05 | 3.72E−04 | 5.15E−10 | | 6.64E+05 | 6.35E−03 | 9.57E−09 | | 0.7 | 12.1 |
| C1_IPN009VH2-SG4GK/IPN93L0021-SK1 | 6.32E+05 | 2.03E−03 | 3.21E−09 | | 1.20E+10 | 1.14E+02 | 9.54E−09 | | 1.2 | 3.6 |
| C1_IPN009VH2-SG4GK/IPN93L0023-SK1 | 7.16E+05 | 1.31E−03 | 1.83E−09 | | 6.67E+06 | 9.20E−02 | 1.38E−08 | | 0.8 | 6.3 |
| C1_IPN009VH2-SG4GK/IPN93L0024-SK1 | 3.84E+05 | 1.49E−03 | 3.87E−09 | | 5.92E+06 | 1.32E−01 | 2.23E−08 | | 1.6 | 9.1 |

TABLE 3-1

| Name of antibody | Abbregation | Name of VH | Mutation(s) in VH from IPN009VH2 | Name of VL | Mutation(s) in VL from IPN009VK3 | Kon (7.4+) | koff (7.4+) | KD (7.4 +) | Binding response (7.4+) |
|---|---|---|---|---|---|---|---|---|---|
| C1_IPN009VH2-SG4GK/IPN009VK3-SK1 | IPN009VH2/IPN009VK3 | IPN009VH2 | — | IPN009VK3 | — | 3.62E+05 | 2.98E−04 | 8.24E−10 | |
| C1_IPN009VH2-SG4GK/IPN93L0028-SK1 | IPN009VH2/IPN93L0028 | IPN009VH2 | — | IPN93L0028 | Y92H/L94H | 3.43E+05 | 4.76E−03 | 1.39E−08 | |
| C1_IPN009VH2-SG4GK/IPN93L0029-SK1 | IPN009VH2/IPN93L0029 | IPN009VH2 | — | IPN93L0029 | Y92H/P95H | 4.94E+05 | 8.97E−03 | 1.82E−08 | |
| C1_IPN009VH2-SG4GK/IPN93L0030-SK1 | IPN009VH2/IPN93L0030 | IPN009VH2 | — | IPN93L0030 | L94H/P95H | 6.12E+05 | 1.56E−02 | 2.55E−08 | low |
| C1_IPN009VH2-SG4GK/IPN93L0031-SK1 | IPN009VH2/IPN93L0031 | IPN009VH2 | — | IPN93L0031 | Y92H/L94H/P95H | 4.76E+04 | 8.00E−06 | 1.68E−10 | low |
| C1_IPN92H0026-SG4GK/IPN93L0021-SK1 | IPN92H0026/IPN93L0021 | IPN92H0026 | G65H | IPN93L0021 | Y92H | 5.87E+05 | 4.72E−04 | 8.04E−10 | |
| C1_IPN92H0026-SG4GK/IPN93L0023-SK1 | IPN92H0026/IPN93L0023 | IPN92H0026 | G65H | IPN93L0023 | L94H | 5.23E+05 | 6.08E−04 | 1.16E−09 | |
| C1_IPN92H0026-SG4GK/IPN93L0024-SK1 | IPN92H0026/IPN93L0024 | IPN92H0026 | G65H | IPN93L0024 | P95H | 4.12E+05 | 4.70E−04 | 1.14E−09 | |
| C1_IPN92H0026-SG4GK/IPN93L0028-SK1 | IPN92H0026/IPN93L0028 | IPN92H0026 | G65H | IPN93L0028 | Y92H/L94H | 5.35E+05 | 2.55E−03 | 4.76E−09 | |
| C1_IPN92H0026-SG4GK/IPN93L0029-SK1 | IPN92H0026/IPN93L0029 | IPN92H0026 | G65H | IPN93L0029 | Y92H/P95H | 5.07E+05 | 4.57E−03 | 9.03E−09 | |
| C1_IPN92H0026-SG4GK/IPN93L0030-SK1 | IPN92H0026/IPN93L0030 | IPN92H0026 | G65H | IPN93L0030 | L94H/P95H | 4.14E+05 | 1.03E−02 | 2.48E−08 | |
| C1_IPN92H0026-SG4GK/IPN93L0031-SK1 | IPN92H0026/IPN93L0031 | IPN92H0026 | G65H | IPN93L0031 | Y92H/L94H/P95H | 2.33E+04 | 1.60E−02 | 6.84E−07 | low |
| C1_IPN92H0033-SG4GK/IPN93L0021-SK1 | IPN92H0033/IPN93L0021 | IPN92H0033 | Y99H | IPN93L0021 | Y92H | 3.50E+05 | 6.72E−04 | 1.92E−09 | |
| C1_IPN92H0033-SG4GK/IPN93L0023-SK1 | IPN92H0033/IPN93L0023 | IPN92H0033 | Y99H | IPN93L0023 | L94H | 3.01E+05 | 9.78E−04 | 3.25E−09 | |
| C1_IPN92H0033-SG4GK/IPN93L0024-SK1 | IPN92H0033/IPN93L0024 | IPN92H0033 | Y99H | IPN93L0024 | P95H | 2.68E+05 | 7.76E−04 | 2.90E−09 | |
| C1_IPN92H0033-SG4GK/IPN93L0028-SK1 | IPN92H0033/IPN93L0028 | IPN92H0033 | Y99H | IPN93L0028 | Y92H/L94H | 3.35E+05 | 2.18E−03 | 6.50E−09 | |
| C1_IPN92H0033-SG4GK/IPN93L0029-SK1 | IPN92H0033/IPN93L0029 | IPN92H0033 | Y99H | IPN93L0029 | Y92H/P95H | 4.79E+05 | 7.40E−03 | 1.54E−08 | |
| C1_IPN92H0033-SG4GK/IPN93L0030-SK1 | IPN92H0033/IPN93L0030 | IPN92H0033 | Y99H | IPN93L0030 | L94H/P95H | 6.03E+05 | 1.46E−02 | 2.42E−08 | |
| C1_IPN92H0033-SG4GK/IPN93L0031-SK1 | IPN92H0033/IPN93L0031 | IPN92H0033 | Y99H | IPN93L0031 | Y92H/L94H/P95H | 5.22E+05 | 1.87E−03 | 3.59E−09 | low |
| C1_IPN92H0038-SG4GK/IPN009VK3-SK1 | IPN92H0033/IPN009VK3 | IPN92H0038 | G65H/Y99H | IPN009VK3 | — | 4.15E+05 | 2.82E−04 | 6.79E−10 | |
| C1_IPN92H0038-SG4GK/IPN93L0021-SK1 | IPN92H0038/IPN93L0021 | IPN92H0038 | G65H/Y99H | IPN93L0021 | Y92H | 4.98E+05 | 4.77E−04 | 9.58E−10 | |
| C1_IPN92H0038-SG4GK/IPN93L0023-SK1 | IPN92H0038/IPN93L0023 | IPN92H0038 | G65H/Y99H | IPN93L0023 | L94H | 4.22E+05 | 8.08E−04 | 1.91E−09 | |
| C1_IPN92H0038-SG4GK/IPN93L0024-SK1 | IPN92H0038/IPN93L0024 | IPN92H0038 | G65H/Y99H | IPN93L0024 | P95H | 3.80E+05 | 5.96E−04 | 1.57E−09 | |
| C1_IPN92H0038-SG4GK/IPN93L0028-SK1 | IPN92H0038/IPN93L0028 | IPN92H0038 | G65H/Y99H | IPN93L0028 | Y92H/L94H | 5.28E+05 | 1.25E−03 | 2.36E−09 | |
| C1_IPN92H0038-SG4GK/IPN93L0029-SK1 | IPN92H0038/IPN93L0029 | IPN92H0038 | G65H/Y99H | IPN93L0029 | Y92H/P95H | 4.19E+05 | 3.00E−03 | 7.15E−09 | |

TABLE 3-1-continued

| Name of antibody | Abbregation | Name of VH | Mutation(s) in VH from IPN009VH2 | Name of VL | Mutation(s) in VL from IPN009VK3 | Kon (7.4+) | koff (7.4+) | KD (7.4 +) | Binding response (7.4+) |
|---|---|---|---|---|---|---|---|---|---|
| C1_IPN92H0038-SG4GK/IPN93L0030-SK1 | IPN92H0038/IPN93L0030 | IPN92H0038 | G65H/Y99H | IPN93L0030 | L94H/P95H | 5.58E+05 | 1.11E−02 | 1.99E−08 | |
| C1_IPN92H0038-SG4GK/IPN93L0031-SK1 | IPN92H0038/IPN93L0031 | IPN92H0038 | G65H/Y99H | IPN93L0031 | Y92H/L94H/P95H | 7.59E+06 | 3.96E−02 | 5.22E−09 | low |
| C1_IPN92H0048-SG4GK/IPN93L0024-SK1 | IPN92H0048/IPN93L0024 | IPN92H0048 | F27H/Y99H | IPN93L0024 | P95H | 2.61E+05 | 8.20E−04 | 3.14E−09 | |

TABLE 3-2

| Name of antibody | Kon (5.8+) | koff (5.8+) | KD (5.8+) | Binding response (5.8+) | Kon (5.8−) | koff (5.8−) | KD (5.8−) | Binding response (5.8−) | KD 5(+)/7(+) | KD 5(−)/7(+) |
|---|---|---|---|---|---|---|---|---|---|---|
| C1_IPN009VH2-SG4GK/IPN009VK3-SK1 | 6.62E+05 | 1.08E−04 | 1.64E−10 | | 6.06E+05 | 2.04E−03 | 3.37E−09 | | 0.2 | 4.1 |
| C1_IPN009VH2-SG4GK/IPN93L0028-SK1 | 5.34E+05 | 7.51E−03 | 1.41E−08 | | 5.28E+05 | 3.51E−03 | 6.66E−09 | low | 1.0 | 0.5 |
| C1_IPN009VH2-SG4GK/IPN93L0029-SK1 | 5.53E+05 | 8.57E−03 | 1.55E−08 | | 5.34E+05 | 2.96E−03 | 5.54E−09 | low | 0.9 | 0.3 |
| C1_IPN009VH2-SG4GK/IPN93L0030-SK1 | 4.87E+05 | 2.22E−02 | 4.56E−08 | low | 4.42E+06 | 5.77E−03 | 1.30E−09 | low | 1.8 | 0.1 |
| C1_IPN009VH2-SG4GK/IPN93L0031-SK1 | 5.32E+05 | 1.27E−02 | 2.39E−08 | low | 7.11E+02 | 3.52E−03 | 4.96E−06 | low | 142.3 | 29523.8 |
| C1_IPN92H0026-SG4GK/IPN93L0021-SK1 | 7.63E+05 | 1.49E−03 | 1.95E−09 | | 2.10E+07 | 1.70E−01 | 8.12E−09 | | 2.4 | 10.1 |
| C1_IPN92H0026-SG4GK/IPN93L0023-SK1 | 8.13E+05 | 1.24E−03 | 1.53E−09 | | 6.23E+06 | 6.19E−02 | 9.95E−09 | | 1.3 | 8.6 |
| C1_IPN92H0026-SG4GK/IPN93L0024-SK1 | 4.51E+05 | 1.43E−03 | 3.16E−09 | | 7.43E+06 | 1.12E−01 | 1.51E−08 | | 2.8 | 13.2 |
| C1_IPN92H0026-SG4GK/IPN93L0028-SK1 | 5.57E+05 | 5.90E−03 | 1.06E−08 | | 6.40E+06 | 1.76E−01 | 2.76E−08 | low | 2.2 | 5.8 |
| C1_IPN92H0026-SG4GK/IPN93L0029-SK1 | 6.02E+05 | 6.13E−03 | 1.02E−08 | | 8.12E+05 | 4.12E−03 | 5.07E−09 | low | 1.1 | 0.6 |
| C1_IPN92H0026-SG4GK/IPN93L0030-SK1 | 2.26E+06 | 5.92E−02 | 2.62E−08 | low | 4.46E+03 | 1.20E−03 | 2.70E−07 | low | 1.1 | 10.9 |
| C1_IPN92H0026-SG4GK/IPN93L0031-SK1 | 4.14E+03 | 1.78E−02 | 4.29E−06 | low | 6.17E+03 | 1.33E−03 | 2.15E−07 | low | 6.3 | 0.3 |
| C1_IPN92H0033-SG4GK/IPN93L0021-SK1 | 5.85E+05 | 2.93E−03 | 5.01E−09 | | 5.42E+11 | 4.12E+03 | 7.59E−09 | low | 2.6 | 4.0 |
| C1_IPN92H0033-SG4GK/IPN93L0023-SK1 | 5.59E+05 | 2.82E−03 | 5.05E−09 | | 1.27E+10 | 1.44E+02 | 1.13E−08 | low | 1.6 | 3.5 |
| C1_IPN92H0033-SG4GK/IPN93L0024-SK1 | 5.19E+05 | 4.50E−03 | 8.66E−09 | | 4.00E+10 | 2.12E+02 | 5.30E−09 | low | 3.0 | 1.8 |
| C1_IPN92H0033-SG4GK/IPN93L0028-SK1 | 7.17E+05 | 1.44E−02 | 2.01E−08 | | 6.58E+05 | 5.60E−03 | 8.50E−09 | low | 3.1 | 1.3 |
| C1_IPN92H0033-SG4GK/IPN93L0029-SK1 | 9.05E+05 | 2.22E−02 | 2.46E−08 | | 3.84E+05 | 3.76E−03 | 9.79E−09 | low | 1.6 | 0.6 |
| C1_IPN92H0033-SG4GK/IPN93L0030-SK1 | 5.03E+05 | 4.49E−02 | 8.93E−08 | low | 2.35E+04 | 6.03E−02 | 2.56E−06 | low | 3.7 | 105.8 |
| C1_IPN92H0033-SG4GK/IPN93L0031-SK1 | 8.07E+05 | 2.09E−03 | 2.59E−09 | low | 6.74E+05 | 9.34E−03 | 1.39E−08 | low | 0.7 | 3.9 |

TABLE 3-2-continued

| Name of antibody | Kon (5.8+) | koff (5.8+) | KD (5.8+) | Binding response (5.8+) | Kon (5.8−) | koff (5.8−) | KD (5.8−) | Binding response (5.8−) | KD 5(+)/ 7(+) | KD 5(−)/ 7(+) |
|---|---|---|---|---|---|---|---|---|---|---|
| C1_IPN92H0038-SG4GK/IPN009VK3-SK1 | 6.93E+05 | 4.63E−04 | 6.68E−10 | | 6.46E+05 | 5.38E−03 | 8.33E−09 | | 1.0 | 12.3 |
| C1_IPN92H0038-SG4GK/IPN93L0021-SK1 | 6.34E+05 | 2.24E−03 | 3.53E−09 | | 1.41E+10 | 1.44E+02 | 1.02E−08 | low | 3.7 | 10.6 |
| C1_IPN92H0038-SG4GK/IPN93L0023-SK1 | 5.24E+05 | 2.79E−03 | 5.33E−09 | | 9.25E+09 | 1.12E+02 | 1.21E−08 | low | 2.8 | 6.3 |
| C1_IPN92H0038-SG4GK/IPN93L0024-SK1 | 5.11E+05 | 4.18E−03 | 8.19E−09 | | 1.25E+11 | 6.83E+02 | 5.47E−09 | low | 5.2 | 3.5 |
| C1_IPN92H0038-SG4GK/IPN93L0028-SK1 | 4.45E+05 | 7.89E−03 | 1.77E−08 | | 6.37E+05 | 1.74E−02 | 2.73E−08 | low | 7.5 | 11.6 |
| C1_IPN92H0038-SG4GK/IPN93L0029-SK1 | 5.39E+05 | 1.31E−02 | 2.42E−08 | | 7.89E+05 | 5.22E−03 | 6.62E−09 | low | 3.4 | 0.9 |
| C1_IPN92H0038-SG4GK/IPN93L0030-SK1 | 2.41E+05 | 1.70E−02 | 7.03E−08 | low | 8.98E+03 | 5.38E−03 | 5.99E−07 | low | 3.5 | 30.1 |
| C1_IPN92H0038-SG4GK/IPN93L0031-SK1 | 1.18E+06 | 1.46E−03 | 1.24E−09 | low | 1.22E+06 | 4.76E−03 | 3.90E−09 | low | 0.2 | 0.7 |
| C1_IPN92H0048-SG4GK/IPN93L0024-SK1 | 5.28E+05 | 6.37E−03 | 1.21E−08 | | 6.72E+10 | 2.26E+02 | 3.36E−09 | low | 3.9 | 1.1 |

Example 3: Further Optimization of "pH" and/or "pH and Ca" Dependent of Anti-C1s Antibody C1_IPN92H0033(SEQ ID NO: 17)-SG4GK/IPN93L0024 (SEQ ID NO: 18)-SK1 (IPN92H0033/IPN93L0024) was selected for further optimization. Histidine, Lysine, Arginine, aspartic acid, glutamic acid, and glutamine scanning was conducted for CDRs and certain positions of FRs of IPN92H0033/IPN93L0024. Variants with a mutation were generated and purified, and evaluated using Biacore by the method mentioned above. All variants were evaluated using Biacore as mentioned above. Mutations that improved "pH" and/or "pH and Ca" dependency were selected for the combination. Mutations that improved KD in 7(+) were also selected for the combination. After several rounds of combination, variants with multiple mutations obtained significant "pH" and/or "pH and Ca" dependency. The results of Biacore are shown in Tables 4-1 and 4-2.

As described in Tables 4-1 and 4-2, surprisingly, introduction of charged residue (arginine, lysine, aspartic acid or glutamic acid) into the antibody that already had a histidine residue, significantly improved the pH dependency of antibody-antigen interaction.

TABLE 4-1

| Name of antibody | Abbregation | Name of VH | Mutation(s) in VH from IPN009VH2 | Name of VL | Mutation(s) in VL from IPN009VK3 | Kon (7.4+) | koff (7.4+) | KD (7.4+) | Binding response (7.4+) |
|---|---|---|---|---|---|---|---|---|---|
| C1_IPN009VH2-SG4GK/IPN009VK3-SK1 | IPN009VH2/IPN009VK3 | IPN009VH2 | — | IPN009VK3 | — | 3.62E+05 | 2.98E−04 | 8.24E−10 | |
| C1_IPN92H0033-SG4GK/IPN93L0024-SK1 | IPN92H0033/IPN93L0024 | IPN92H0033 | Y99H | IPN93L0024 | P95H | 2.68E+05 | 7.76E−04 | 2.90E−09 | |
| C1_IPN92H0061-SG4GK/IPN93L0024-SK1 | IPN92H0061/IPN93L0024 | IPN92H0061 | F29K/Y99H | IPN93L0024 | P95H | 2.36E+05 | 1.61E−03 | 6.85E−09 | |
| C1_IPN92H0079-SG4GK/IPN93L0024-SK1 | IPN92H0079/IPN93L0024 | IPN92H0079 | Y32K/Y99H | IPN93L0024 | P95H | 3.73E+05 | 1.25E−03 | 3.36E−09 | |
| C1_IPN92H0080-SG4GK/IPN93L0024-SK1 | IPN92H0080/IPN93L0024 | IPN92H0080 | Y32R/Y99H | IPN93L0024 | P95H | 3.57E+05 | 1.14E−03 | 3.18E−09 | |

TABLE 4-1-continued

| Name of antibody | Abbregation | Name of VH | Mutation(s) in VH from IPN009VH2 | Name of VL | Mutation(s) in VL from IPN009VK3 | Kon (7.4+) | koff (7.4+) | KD (7.4+) | Binding response (7.4+) |
|---|---|---|---|---|---|---|---|---|---|
| C1_IPN92H0091-SG4GK/IPN93L0024-SK1 | IPN92H0091/IPN93L0024 | IPN92H0091 | M34K/Y99H | IPN93L0024 | P95H | 2.77E+05 | 7.46E−04 | 2.69E−09 | |
| C1_IPN92H0117-SG4GK/IPN93L0024-SK1 | IPN92H0117/IPN93L0024 | IPN92H0117 | S52aQ/Y99H | IPN93L0024 | P95H | 2.53E+05 | 8.63E−04 | 3.41E−09 | |
| C1_IPN92H0144-SG4GK/IPN93L0024-SK1 | IPN92H0144/IPN93L0024 | IPN92H0144 | H56K/Y99H | IPN93L0024 | P95H | 3.43E+05 | 1.26E−03 | 3.68E−09 | |
| C1_IPN92H0145-SG4GK/IPN93L0024-SK1 | IPN92H0145/IPN93L0024 | IPN92H0145 | H56R/Y99H | IPN93L0024 | P95H | 3.33E+05 | 1.57E−03 | 4.71E−09 | |
| C1_IPN92H0147-SG4GK/IPN93L0024-SK1 | IPN92H0147/IPN93L0024 | IPN92H0147 | T57D/Y99H | IPN93L0024 | P95H | 3.74E+05 | 7.65E−04 | 2.05E−09 | |
| C1_IPN92H0156-SG4GK/IPN93L0024-SK1 | IPN92H0156/IPN93L0024 | IPN92H0156 | Y58K/Y99H | IPN93L0024 | P95H | 3.64E+05 | 7.71E−04 | 2.12E−09 | |
| C1_IPN92H0157-SG4GK/IPN93L0024-SK1 | IPN92H0157/IPN93L0024 | IPN92H0157 | Y58R/Y99H | IPN93L0024 | P95H | 3.40E+05 | 6.89E−04 | 2.03E−09 | |
| C1_IPN92H0159-SG4GK/IPN93L0024-SK1 | IPN92H0159/IPN93L0024 | IPN92H0159 | Y59D/Y99H | IPN93L0024 | P95H | 3.02E+05 | 6.21E−04 | 2.06E−09 | |
| C1_IPN92H0160-SG4GK/IPN93L0024-SK1 | IPN92H0160/IPN93L0024 | IPN92H0160 | Y59E/Y99H | IPN93L0024 | P95H | 3.68E+05 | 5.58E−04 | 1.52E−09 | |
| C1_IPN92H0162-SG4GK/IPN93L0024-SK1 | IPN92H0162/IPN93L0024 | IPN92H0162 | Y59K/Y99H | IPN93L0024 | P95H | 3.03E+05 | 5.45E−04 | 1.80E−09 | |
| C1_IPN92H0165-SG4GK/IPN93L0024-SK1 | IPN92H0165/IPN93L0024 | IPN92H0165 | L60D/Y99H | IPN93L0024 | P95H | 2.89E+05 | 5.12E−04 | 1.77E−09 | |
| C1_IPN92H0166-SG4GK/IPN93L0024-SK1 | IPN92H0166/IPN93L0024 | IPN92H0166 | L60E/Y99H | IPN93L0024 | P95H | 2.94E+05 | 5.18E−04 | 1.76E−09 | |
| C1_IPN92H0188-SG4GK/IPN93L0024-SK1 | IPN92H0188/IPN93L0024 | IPN92H0188 | K64D/Y99H | IPN93L0024 | P95H | 2.71E+05 | 5.51E−04 | 2.03E−09 | |
| C1_IPN92H0193-SG4GK/IPN93L0024-SK1 | IPN92H0193/IPN93L0024 | IPN92H0193 | G65D/Y99H | IPN93L0024 | P95H | 5.13E+05 | 4.74E−04 | 9.25E−10 | |
| C1_IPN92H0194-SG4GK/IPN93L0024-SK1 | IPN92H0194/IPN93L0024 | IPN92H0194 | G65E/Y99H | IPN93L0024 | P95H | 5.29E+05 | 4.68E−04 | 8.85E−10 | |
| C1_IPN92H0231-SG4GK/IPN93L0024-SK1 | IPN92H0231/IPN93L0024 | IPN92H0231 | G98K/Y99H | IPN93L0024 | P95H | 4.44E+05 | 5.77E−04 | 1.30E−09 | |
| C1_IPN92H0232-SG4GK/IPN93L0024-SK1 | IPN92H0232/IPN93L0024 | IPN92H0232 | G98R/Y99H | IPN93L0024 | P95H | 4.06E+05 | 6.09E−04 | 1.50E−09 | |
| C1_IPN92H0253-SG4GK/IPN93L0024-SK1 | IPN92H0253/IPN93L0024 | IPN92H0253 | Y99H/D101K | IPN93L0024 | P95H | 5.69E+05 | 6.90E−05 | 1.21E−10 | |

TABLE 4-1-continued

| Name of antibody | Abbregation | Name of VH | Mutation(s) in VH from IPN009VH2 | Name of VL | Mutation(s) in VL from IPN009VK3 | Kon (7.4+) | koff (7.4+) | KD (7.4+) | Binding response (7.4+) |
|---|---|---|---|---|---|---|---|---|---|
| C1_IPN92H0033-SG4GK/IPN93L0072-SK1 | IPN92H0033/IPN93L0072 | IPN92H0033 | Y99H | IPN93L0072 | S29K/P95H | 4.13E+05 | 5.67E−04 | 1.37E−09 | |
| C1_IPN92H0033-SG4GK/IPN93L0090-SK1 | IPN92H0033/IPN93L0090 | IPN92H0033 | Y99H | IPN93L0090 | Y32K/P95H | 4.82E+05 | 6.76E−04 | 1.40E−09 | |
| C1_IPN92H0281-SG4GK/IPN93L0024-SK1 | IPN92H0281/IPN93L0024 | IPN92H0281 | H56K/Y59E/K64D/G65E/G98K/Y99H | IPN93L0024 | P95H | 3.96E+05 | 1.00E−03 | 2.52E−09 | |
| C1_IPN92H0282-SG4GK/IPN93L0024-SK1 | IPN92H0282/IPN93L0024 | IPN92H0282 | Y59E/K64D/G65E/G98K/Y99H | IPN93L0024 | P95H | 3.83E+05 | 6.32E−04 | 1.65E−09 | |
| C1_IPN92H0261-SG4GK/IPN93L0091-SK1 | IPN92H0261/IPN93L0091 | IPN92H0261 | Y59E/G98K/Y99H | IPN93L0091 | Y32R/P95H | 7.86E+05 | 7.74E−04 | 9.85E−10 | |
| C1_IPN92H0279-SG4GK/IPN93L0091-SK1 | IPN92H0279/IPN93L0091 | IPN92H0279 | Y59E/G65E/G98K/Y99H | IPN93L0091 | Y32R/P95H | 1.31E+06 | 8.97E−04 | 6.86E−10 | |
| C1_IPN92H0286-SG4GK/IPN93L0205-SK1 | IPN92H0286/IPN93L0205 | IPN92H0286 | Y32K/G65H/Y99H | IPN93L0205 | Y32R/Y92H/L94H | 9.84E+05 | 1.56E−03 | 1.58E−09 | |
| C1_IPN92H0282-SG4GK/IPN93L0091-SK1 | IPN92H0282/IPN93L0091 | IPN92H0282 | Y59E/K64D/G65E/G98K/Y99H | IPN93L0091 | Y32R/P95H | 4.71E+05 | 9.24E−04 | 1.96E−09 | |
| C1_IPN92H0281-SG4GK/IPN93L0091-SK1 | IPN92H0281/IPN93L0091 | IPN92H0281 | H56K/Y59E/K64D/G65E/G98K/Y99H | IPN93L0091 | Y32R/P95H | 4.57E+05 | 2.16E−03 | 4.72E−09 | |
| C1_IPN92H0288-SG4GK/IPN93L0212-SK1 | IPN92H0288/IPN93L0212 | IPN92H0288 | Y59E/K64D/G98K/Y99H | IPN93L0212 | S27aE/S30E/Y32R/P95H | 6.48E+05 | 1.17E−03 | 1.81E−09 | |

TABLE 4-2

| Name of antibody | Kon (5.8+) | koff (5.8+) | KD (5.8+) | Binding response (5.8+) | Kon (5.8−) | koff (5.8−) | KD (5.8−) | Binding response (5.8−) | KD 5(+)/7(+) | KD 5(−)/7(+) |
|---|---|---|---|---|---|---|---|---|---|---|
| C1_IPN009VH2-SG4GK/IPN009VK3-SK1 | 6.62E+05 | 1.08E−04 | 1.64E−10 | | 6.06E+05 | 2.04E−03 | 3.37E−09 | | 0.2 | 4.09 |
| C1_IPN92H0033-SG4GK/IPN93L0024-SK1 | 5.19E+05 | 4.50E−03 | 8.66E−09 | | 4.00E+10 | 2.12E+02 | 5.30E−09 | low | 3.0 | 1.83 |
| C1_IPN92H0061-SG4GK/IPN93L0024-SK1 | 1.85E+06 | 2.20E−02 | 1.19E−08 | low | 6.33E+05 | 3.44E−03 | 5.43E−09 | low | 1.7 | 0.79 |
| C1_IPN92H0079-SG4GK/IPN93L0024-SK1 | 8.38E+05 | 1.62E−02 | 1.93E−08 | | 5.94E+05 | 5.20E−03 | 8.75E−09 | low | 5.7 | 2.60 |
| C1_IPN92H0080-SG4GK/IPN93L0024-SK1 | 8.14E+05 | 1.29E−02 | 1.59E−08 | | 7.17E+05 | 6.51E−03 | 9.09E−09 | low | 5.0 | 2.86 |
| C1_IPN92H0091-SG4GK/IPN93L0024-SK1 | 5.30E+05 | 6.34E−03 | 1.20E−08 | | 7.80E+08 | 2.67E+00 | 3.43E−09 | low | 4.5 | 1.28 |
| C1_IPN92H0117-SG4GK/IPN93L0024-SK1 | 6.10E+05 | 7.99E−03 | 1.31E−08 | | 7.03E+05 | 5.42E−03 | 7.71E−09 | low | 3.8 | 2.26 |

TABLE 4-2-continued

| Name of antibody | Kon (5.8+) | koff (5.8+) | KD (5.8+) | Binding response (5.8+) | Kon (5.8−) | koff (5.8−) | KD (5.8−) | Binding response (5.8−) | KD 5(+)/7(+) | KD 5(−)/7(+) |
|---|---|---|---|---|---|---|---|---|---|---|
| C1_IPN92H0144-SG4GK/IPN93L0024-SK1 | 1.13E+06 | 2.65E−02 | 2.34E−08 | low | 5.62E+05 | 3.17E−03 | 5.65E−09 | low | 6.4 | 1.54 |
| C1_IPN92H0145-SG4GK/IPN93L0024-SK1 | 2.58E+06 | 4.96E−02 | 1.92E−08 | low | 4.69E+05 | 3.00E−03 | 6.40E−09 | low | 4.1 | 1.36 |
| C1_IPN92H0147-SG4GK/IPN93L0024-SK1 | 4.45E+05 | 5.89E−03 | 1.32E−08 | | 6.50E+10 | 2.10E+02 | 3.23E−09 | low | 6.4 | 1.58 |
| C1_IPN92H0156-SG4GK/IPN93L0024-SK1 | 6.41E+05 | 9.48E−03 | 1.48E−08 | | 6.45E+05 | 6.32E−03 | 9.80E−09 | low | 7.0 | 4.62 |
| C1_IPN92H0157-SG4GK/IPN93L0024-SK1 | 6.36E+05 | 1.20E−02 | 1.88E−08 | | 5.64E+05 | 5.83E−03 | 1.03E−08 | low | 9.3 | 5.07 |
| C1_IPN92H0159-SG4GK/IPN93L0024-SK1 | 4.21E+05 | 6.99E−03 | 1.66E−08 | | 5.44E+05 | 4.01E−03 | 7.36E−09 | low | 8.1 | 3.57 |
| C1_IPN92H0160-SG4GK/IPN93L0024-SK1 | 4.61E+05 | 6.34E−03 | 1.37E−08 | | 5.62E+05 | 4.11E−03 | 7.32E−09 | low | 9.0 | 4.82 |
| C1_IPN92H0162-SG4GK/IPN93L0024-SK1 | 4.56E+05 | 5.24E−03 | 1.15E−08 | | 1.60E+06 | 7.84E−03 | 4.89E−09 | low | 6.4 | 2.72 |
| C1_IPN92H0165-SG4GK/IPN93L0024-SK1 | 6.08E+05 | 2.28E−03 | 3.74E−09 | | 8.74E+07 | 7.15E−01 | 8.18E−09 | low | 2.1 | 4.62 |
| C1_IPN92H0166-SG4GK/IPN93L0024-SK1 | 6.00E+05 | 2.26E−03 | 3.77E−09 | | 1.02E+08 | 6.87E−01 | 6.75E−09 | low | 2.1 | 3.84 |
| C1_IPN92H0188-SG4GK/IPN93L0024-SK1 | 5.04E+05 | 4.13E−03 | 8.21E−09 | | 2.53E+06 | 1.06E−02 | 4.21E−09 | low | 4.0 | 2.07 |
| C1_IPN92H0193-SG4GK/IPN93L0024-SK1 | 7.27E+05 | 4.17E−03 | 5.74E−09 | | 2.14E+07 | 6.85E−02 | 3.21E−09 | low | 6.2 | 3.47 |
| C1_IPN92H0194-SG4GK/IPN93L0024-SK1 | 7.51E+05 | 4.29E−03 | 5.72E−09 | | 8.02E+05 | 5.17E−03 | 6.45E−09 | low | 6.5 | 7.29 |
| C1_IPN92H0231-SG4GK/IPN93L0024-SK1 | 5.68E+05 | 5.44E−03 | 9.59E−09 | | 1.28E+06 | 6.74E−03 | 5.28E−09 | low | 7.4 | 4.06 |
| C1_IPN92H0232-SG4GK/IPN93L0024-SK1 | 5.70E+05 | 4.85E−03 | 8.49E−09 | | 3.23E+06 | 1.73E−02 | 5.19E−09 | low | 5.7 | 3.46 |
| C1_IPN92H0253-SG4GK/IPN93L0024-SK1 | 4.71E+05 | 7.17E−04 | 1.52E−09 | | 5.78E+05 | 1.47E−02 | 2.54E−08 | | 12.6 | 209.92 |
| C1_IPN92H0033-SG4GK/IPN93L0072-SK1 | 5.30E+05 | 5.29E−03 | 9.12E−09 | | 9.67E+05 | 5.53E−03 | 5.72E−09 | low | 6.7 | 4.18 |
| C1_IPN92H0033-SG4GK/IPN93L0090-SK1 | 5.77E+05 | 5.50E−03 | 9.52E−09 | | 5.95E+05 | 4.27E−03 | 7.18E−09 | low | 6.8 | 5.13 |
| C1_IPN92H0281-SG4GK/IPN93L0024-SK1 | 1.02E+06 | 2.40E−02 | 2.36E−08 | | 6.02E+05 | 3.00E−03 | 4.98E−09 | low | 9.4 | 1.98 |
| C1_IPN92H0282-SG4GK/IPN93L0024-SK1 | 5.53E+05 | 9.98E−03 | 1.80E−08 | | 3.82E+05 | 3.27E−03 | 8.55E−09 | low | 10.9 | 5.18 |
| C1_IPN92H0261-SG4GK/IPN93L0091-SK1 | 3.32E+05 | 5.33E−03 | 1.61E−08 | low | 6.06E+05 | 7.36E−03 | 1.21E−08 | low | 16.3 | 12.28 |
| C1_IPN92H0279-SG4GK/IPN93L0091-SK1 | 3.42E+05 | 6.84E−03 | 2.00E−08 | low | 1.18E+06 | 6.11E−03 | 5.17E−09 | low | 29.2 | 7.54 |
| C1_IPN92H0286-SG4GK/IPN93L0205-SK1 | 5.27E+05 | 3.46E−03 | 6.57E−09 | low | 1.03E+06 | 4.77E−03 | 4.65E−09 | low | 4.2 | 2.94 |
| C1_IPN92H0282-SG4GK/IPN93L0091-SK1 | 4.45E+05 | 7.55E−03 | 1.69E−08 | low | 6.70E+05 | 1.48E−03 | 2.21E−09 | low | 8.6 | 1.13 |
| C1_IPN92H0281-SG4GK/IPN93L0091-SK1 | 6.25E+05 | 7.07E−03 | 1.13E−08 | low | 5.85E+05 | 2.27E−03 | 3.88E−09 | low | 2.4 | 0.82 |

TABLE 4-2-continued

| Name of antibody | Kon (5.8+) | koff (5.8+) | KD (5.8+) | Binding response (5.8+) | Kon (5.8−) | koff (5.8−) | KD (5.8−) | Binding response (5.8−) | KD 5(+)/ 7(+) | KD 5(−)/ 7(+) |
|---|---|---|---|---|---|---|---|---|---|---|
| C1_IPN92H0288-SG4GK/IPN93L0212-SK1 | 9.45E+05 | 1.98E−02 | 2.10E−08 | low | 7.84E+05 | 5.33E−03 | 6.79E−09 | low | 11.6 | 3.75 |

Without being bounded by a particular theory, a histidine residue in the antibody can interact with various residues surrounding the histidine residue in the antibody. Such interaction can affect the structure of antibody or the conformation of the CDRs. Histidine becomes protonated and positively charged at the acidic pH. Introduction of positively charged residue, such as arginine or lysine, at the position surrounding the histidine can cause repulsion between the positively charged residue and the protonated histidine at acidic pH, and thus induce structural or conformational change of the antibody or the CDRs. Similarly, introduction of negatively charged residue, such as aspartic acid or glutamic acid, at the position surrounding the histidine can cause interaction between the negatively charged residue and the protonated histidine at acidic pH, and thus induce structural or conformational change of the antibody or the CDRs. These structural or conformational changes of the antibody or the CDRs that occur at acidic pH can affect the antigen binding of the antibody, and reduce the binding affinity of the antibody to an antigen at acidic pH. In summary, introduction of charged residue (such as arginine, lysine, aspartic acid or glutamic acid) at the position surrounding the histidine residue in an antibody can reduce the binding affinity of the antibody to the antigen at acidic pH, and thus improve the pH dependency of antibody-antigen interaction in a unique mechanism.

Example 4: Reducing Non-Specific Binding

Non-specific binding is one of the important factors in predicting antibody pharmacokinetics. (MABS 2017, VOL. 9, NO. 5, 756-766). Since high non-specific binding would lead to fast clearance of an antibody and resulting in poor antibody pharmacokinetics, antibodies with high non-specific binding is unfavorable in developing therapeutic antibodies. Extracellular matrix binding assay (ECM binding assay) is one of the assay methods to predict non-specific binding (WO 2012/093704).

"pH"- and "pH and Ca"-dependent antibodies were selected for ECM binding assay. The ECM binding assay was incorporated with electrochemiluminescence (ECL) based on Meso Scale Discovery (MSD) technology. The ECM (BD Matrigel) was initially coated onto the surface of a Multi-Array High Bind 96-well plate (MSD) at 4 degrees C. overnight. The ECM-coated plate was then blocked with ECL blocking buffer either in pH 7.4 (20 mM ACES, 150 mM NaCl, 1.2 mM CaCl2, pH7.4 with 0.05% Tween 20 and 0.5% BSA) or pH 5.8 (20 mM ACES, 150 mM NaCl, 1.2 mM CaCl2, pH5.8 with 0.05% Tween 20 and 0.5% BSA) for 2 hrs, 30 degrees C. Selected variants and assay controls were then diluted with dilution buffer either in pH 7.4 (20 mM ACES, 150 mM NaCl, 1.2 mM CaCl2, pH7.4 with 0.01% Tween 20 and 0.1% BSA) or pH 5.8 (20 mM ACES, 150 mM NaCl, 1.2 mM CaCl2, pH5.8 with 0.01% Tween 20 and 0.1% BSA). Diluted samples and assay controls were incubated on the plate for 1 hr, 30 degrees C., at 600 rpm, followed by incubation with 0.25% glutaraldehyde (Sigma) for 10 mins at room temperature. The plate was then washed with 1×PBST (Sigma) and incubated with sulfo-tag labelled goat anti-human IgG (Invitrogen) for 1 hr at 30 degrees C., 600 rpm. The plate was washed again with 1×PBST and Read Buffer T (2×) with surfactant (MSD) was added into each well. The plate was read using MESO SECTOR S 600. Results of the ECM binding assay are shown in Table 5. The binding of selected variants against ECM at pH 5.8 is higher than that of IPN009VH2/IPN009VK3. Further optimization to reduce the binding against ECM was conducted to improve antibody pharmacokinetics. Negatively-charged residues were introduced into selected variants. Binding affinity and ECM binding were evaluated using Biacore and ECM binding assay as mentioned above, respectively. Several residues were identified to reduce ECM binding while maintaining or enhancing "pH" and/or "pH and Ca" dependency. By combining these identified mutations, three antibodies, C1_IPN92H0288(SEQ ID NO: 19)-SG4GK/IPN93L0211(SEQ ID NO: 20)-SK1, C1_IPN92H0288-SG4GK/IPN93L0058(SEQ ID NO: 21)-SK1, and C1_IPN92H0307(SEQ ID NO: 22)-SG4GK/IPN93L0058-SK1 were successfully generated. These three variants showed good "pH" and "pH and Ca" dependency with lower ECM binding at both pH 7.4 and pH 5.8. The results of Biacore and ECM binding assay of the three variants are shown in Table 6.

TABLE 5

| Name of antibody | ECM binding at pH 7.4 | | Average of ECM binding at pH 7.4 (N = 2) | ECM binding at pH 5.8 | | Average of ECM binding at pH 5.8 | Ratio to IPN009VH2/ IPN009VK3 at pH 7.4 | Ratio to IPN009VH2/ IPN009VK3 at pH 5.8 |
|---|---|---|---|---|---|---|---|---|
| IPN009VH2/IPN009VK3 | 9819 | 13150 | 11484.5 | 7646 | 6524 | 7085 | 1.00 | 1.00 |
| IPN92H0033/IPN009VK3 | 11067 | 11952 | 11509.5 | 57277 | 60338 | 58807.5 | 1.00 | 8.30 |
| IPN009VH2/IPN93L0021 | 7806 | 7542 | 7674 | 40282 | 44194 | 42238 | 0.67 | 5.96 |
| IPN009VH2/IPN93L0023 | 14043 | 11480 | 12761.5 | 35089 | 35856 | 35472.5 | 1.11 | 5.01 |
| IPN009VH2/IPN93L0024 | 20473 | 18567 | 19520 | 25709 | 25474 | 25591.5 | 1.70 | 3.61 |
| IPN92H0038/IPN93L0024 | 21067 | 20744 | 20905.5 | 194790 | 199601 | 197195.5 | 1.82 | 27.83 |
| IPN92H0033/IPN93L0024 | 16486 | 17975 | 17230.5 | 77873 | 85421 | 81647 | 1.50 | 11.52 |

TABLE 5-continued

| Name of antibody | ECM binding at pH 7.4 | | Average of ECM binding at pH 7.4 (N = 2) | ECM binding at pH 5.8 | | Average of ECM binding at pH 5.8 | Ratio to IPN009VH2/ IPN009VK3 at pH 7.4 | Ratio to IPN009VH2/ IPN009VK3 at pH 5.8 |
|---|---|---|---|---|---|---|---|---|
| IPN92H0281/IPN93L0024 | 8588 | 8988 | 8788 | 98350 | 103612 | 100981 | 0.77 | 14.25 |
| IPN92H0286/IPN93L0205 | 136963 | 136320 | 136641.5 | 461103 | 558294 | 509698.5 | 11.90 | 71.94 |

TABLE 6

| Name of antibody | Abbregation | Name of VH | Mutation(s) in VH from IPN009VH2 | Name of VL | Mutation(s) in VL from IPN009VK3 | Kon (7.4+) |
|---|---|---|---|---|---|---|
| C1_IPN009VH2-SG4G/ IPN009VK3-SK1 | IPN009VH2/ IPN009VK3 | IPN009VH2 | — | IPN009VK3 | — | 3.62E+05 |
| C1_IPN92H0288-SG4GK/ IPN93L0058-SK1 | IPN92H0288/ IPN93L0058 | IPN92H0288 | Y59E/K64D/ G98K/Y99H | IPN93L0058 | S27aE/P95H | 6.54E+05 |
| C1_IPN92H0288-SG4GK/ IPN93L0211-SK1 | IPN92H0288/ IPN93L0211 | IPN92H0288 | Y59E/K64D/ G98K/Y99H | IPN93L0211 | S27aE/S30E/ P95H | 5.27E+05 |
| C1_IPN92H0307-SG4GK/ IPN93L0058-SK1 | IPN92H0307/ IPN93L0058 | PN92H0307 | T28E/S30E/ Y59E/K64D/ G98K/Y99H | IPN93L0058 | S27aE/P95H | 4.46E+05 |

| Name of antibody | koff (7.4+) | KD (7.4+) | Binding response (7.4+) | Kon (5.8+) |
|---|---|---|---|---|
| C1_IPN009VH2-SG4G/ IPN009VK3-SK1 | 2.98E−04 | 8.24E−10 | 104.4 | 6.62E+05 |
| C1_IPN92H0288-SG4GK/ IPN93L0058-SK1 | 5.48E−04 | 8.38E−10 | | 7.32E+05 |
| C1_IPN92H0288-SG4GK/ IPN93L0211-SK1 | 8.80E−04 | 1.67E−09 | | 1.77E+06 |
| C1_IPN92H0307-SG4GK/ IPN93L0058-SK1 | 8.63E−04 | 1.93E−09 | | 7.31E+05 |

| Name of antibody | koff (5.8+) | KD (5.8+) | Binding response (5.8+) | Kon (5.8−) | koff (5.8−) | KD (5.8−) |
|---|---|---|---|---|---|---|
| C1_IPN009VH2-SG4GK/ IPN009VK3-SK1 | 1.08E−04 | 1.64E−10 | 132.9 | 6.05E+05 | 2.04E−03 | 3.37E−09 |
| C1_IPN92H0288-SG4GK/ IPN93L0058-SK1 | 1.43E−02 | 1.95E−08 | | 5.04E+05 | 4.01E−03 | 7.96E−09 |
| C1_IPN92H0288-SG4GK/ IPN93L0211-SK1 | 2.92E−02 | 1.65E−08 | low | 4.85E+05 | 5.04E−03 | 1.04E−08 |
| C1_IPN92H0307-SG4GK/ IPN93L0058-SK1 | 1.42E−02 | 1.95E−08 | | 3.96E+05 | 1.96E−03 | 4.95E−09 |

| Name of antibody | Binding response (5.8−) | KD 5(+)/ 7(+) | Larger than in KD 5(+)/ 7(+) than IPN009VH2/ IPN009VK3 | KD (5−)/ 7(+) | Larger than in KD 5(−)/ 7(+) than IPN009VH2/ IPN009VK3 |
|---|---|---|---|---|---|
| C1_IPN009VH2-SG4GK/ IPN009VK3-SK1 | 114.9 | 0.2 | | 4.09 | |
| C1_IPN92H0288-SG4GK/ IPN93L0058-SK1 | low | 23.3 | Y | 9.50 | |
| C1_IPN92H0288-SG4GK/ IPN93L0211-SK1 | low | 9.9 | Y | 6.23 | |
| C1_IPN92H0307-SG4GK/ IPN93L0058-SK1 | low | 10.1 | Y | 2.56 | |

| Name of antibody | ECM binding at pH 7.4 | | Average of ECM binding at pH 7.4 (N = 2) | ECM binding at pH 5.8 | | Average of ECM binding at pH 5.8 | Ratio to PN009VH2/ PN009VK3 at pH 7.4 | Ratio to IPN009VH2/ IPN009VK3 at pH 5.8 |
|---|---|---|---|---|---|---|---|---|
| C1_IPN009VH2-SG4GK/ IPN009VK3-SK1 | 9819 | 13150 | 11484.5 | 7646 | 6524 | 7085 | 1.00 | 1.00 |
| C1_IPN92H0288-SG4GK/ IPN93L0058-SK1 | 10045 | 12701 | 11373 | 63744 | 73309 | 68526.5 | 0.99 | 9.67 |

TABLE 6-continued

| | | | | | | | | |
|---|---|---|---|---|---|---|---|---|
| C1_IPN92H0288-SG4GK/<br>IPN93L0211-SK1 | 6129 | 6612 | 6370.5 | 26440 | 23366 | 24903 | 0.55 | 3.51 |
| C1_IPN92H0307-SG4GK/<br>IPN93L0058-SK1 | 5490 | 5947 | 5718.5 | 13886 | 14321 | 14103.5 | 0.50 | 1.99 |

Example 5: Affinity Measurement

The binding affinity of all histidine-substituted variants at pH 7.4 and pH 5.8 were determined at 37 degrees C. using Biacore T200 instrument (GE Healthcare). Recombinant Protein A/G (Pierce) was immobilized onto all flow cells of a CM4 sensor chip using amine coupling kit (GE Healthcare). Antibodies and analytes were prepared in 7(+) buffer (20 mM ACES, 150 mM NaCl, 1.2 mM $CaCl_2$, 0.05% Tween 20, 0.005% $NaN_3$, pH 7.4) or 5(+) buffer (20 mM ACES, 150 mM NaCl, 1.2 mM CaCl2, 0.05% Tween 20, 0.005% NaN3, pH 5.8). Each antibody was captured onto the sensor surface by protein A/G. Antibody capture levels were aimed at 200 resonance unit (RU). Serum-derived human C1s was injected at 12.5, 50 nM for pH 7.4 or at 50, 200 nM for all samples at pH5.8 except IPN92H0281/IPN93L0024-SG136 and IPN92H0286/IPN93L0205-SG136, and 200 and 800 nM for IPN92H0281/IPN93L0024-SG136 and IPN92H0286/IPN93L0205-SG136 at pH5.8, followed by dissociation. Sensor surface was regenerated each cycle with 10 mM Glycine-HCl pH 1.5. Binding affinities were determined by processing and fitting the data to 1:1 binding model using Biacore T200 Evaluation software, version 2.0 (GE Healthcare) (Table 7). An additional dissociation phase at pH 5.8 was integrated immediately after the dissociation phase at pH 7.4. This dissociation rate in 5(+) buffer was determined by processing and fitting data using Scrubber 2.0 (BioLogic Software) curve fitting software. The asterisk mark for affinity values at pH5.8 indicates that the affinity measurements could not be accurately determined due to low binding response.

TABLE 7

| Abbreviation<br>name of antibody | Lot | kon (7.4+) | koff (7.4+) | KD (7.4+) | koff (5.8+<br>of 775+) | koff (5.8+<br>of 775+)/<br>koff (7.4+) |
|---|---|---|---|---|---|---|
| IPN009VH2/IPN009VK3 | PPU2040 | 3.44E+05 | 4.11E−04 | 1.19E−09 | 8.86E−05 | 0.2 |
| IPN92H0033/IPN009VK3 | PPU2041 | 3.77E+05 | 3.80E−04 | 1.01E−09 | 2.65E−04 | 0.7 |
| IPN009VH2/IPN93L0021 | PPU2042 | 1.99E+05 | 5.80E−04 | 2.92E−09 | 1.10E−03 | 1.9 |
| IPN009VH2/IPN93L0023 | PPU2043 | 2.27E+05 | 6.28E−04 | 2.77E−09 | 6.91E−04 | 1.1 |
| IPN009VH2/IPN93L0024 | PPU2044 | 1.80E+05 | 6.12E−04 | 3.40E−09 | 7.41E−04 | 1.2 |
| IPN92H0038/IPN93L0024 | PPU2045 | 3.84E+05 | 4.61E−04 | 1.20E−09 | 3.54E−03 | 7.7 |
| IPN92H0033/IPN93L0024 | PPU2046 | 2.27E+05 | 5.71E−04 | 2.51E−09 | 2.90E−03 | 5.1 |
| IPN92H0281/IPN93L0024 | PPU2047 | 3.19E+05 | 6.45E−04 | 2.02E−09 | 2.47E−02 | 38.2 |
| IPN92H0286/IPN93L0205 | PPU2048 | 5.74E+05 | 8.22E−04 | 1.43E−09 | 1.34E−02 | 16.3 |
| IPN92H0288/IPN93L0211 | PPU2049 | 4.69E+05 | 5.20E−04 | 1.11E−09 | 2.82E−02 | 54.2 |
| IPN92H0288/IPN93L0058 | PPU2050 | 6.66E+05 | 4.08E−04 | 6.11E−10 | 1.58E−02 | 38.8 |
| IPN92H0307/IPN93L0058 | PPU2051 | 3.91E+05 | 5.23E−04 | 1.34E−09 | 1.51E−02 | 28.8 |

| Abbreviation<br>name of antibody | kon (5.8+) | koff (5.8+) | KD (5.8+) | KD (5.8+)/<br>KD (7.4+) |
|---|---|---|---|---|
| IPN009VH2/IPN009VK3 | 3.60E+05 | 1.62E−04 | 4.49E−10 | 0.4 |
| IPN92H0033/IPN009VK3 | 3.89E+05 | 3.62E−04 | 9.31E−10 | 0.9 |
| IPN009VH2/IPN93L0021 | 2.90E+05 | 1.26E−03 | 4.34E−09 | 1.5 |
| IPN009VH2/IPN93L0023 | 3.30E+05 | 8.18E−04 | 2.48E−09 | 0.9 |
| IPN009VH2/IPN93L0024 | 2.21E+05 | 9.56E−04 | 4.32E−09 | 1.3 |
| IPN92H0038/IPN93L0024 | 2.89E+05 | 3.09E−03 | 1.07E−08 | 8.9 |
| IPN92H0033/IPN93L0024 | 2.61E+05 | 3.10E−03 | 1.19E−08 | 4.7 |
| IPN92H0281/IPN93L0024 | 2.17E+05 | 2.67E−02 | 1.23E−07 | 60.9 |
| IPN92H0286/IPN93L0205 | * 2.78E+03 | * 2.37E−02 | * 8.53E−06 | — |
| IPN92H0288/IPN93L0211 | 2.33E+05 | 1.94E−02 | 8.31E−08 | 74.9 |
| IPN92H0288/IPN93L0058 | 3.15E+05 | 1.27E−02 | 4.01E−08 | 65.6 |
| IPN92H0307/IPN93L0058 | 3.18E+05 | 1.21E−02 | 3.81E−08 | 28.4 |

* Not Adopted due to low binding response at pH 5.8

Example 6: Mice PK Study Using pH and/or Ca Dependent Anti-Cs Antibody

Measurement of Anti-C1s Antibody and Total hC1s Concentration in Plasma by High-Performance Liquid Chromatography-Electrospray Tandem Mass Spectrometry (LC/ESI-MS/MS)

The concentrations of anti-C1s antibody and human C1s in mouse plasma was measured by LC/ESI-MS/MS. The calibration standards were prepared by mixing and diluting anti-C1s antibody and human C1s in defined amounts in mouse plasma, resulting in anti-C1s concentrations of 12.5, 25, 50, 100 200, 400 and 800 micrograms (micro g)/mL and human C1s concentrations of 0.977, 1.95, 3.91, 7.81, 15.6, 31.3, 62.5 micro/mL, respectively. A 2 micro L of the calibration standards and plasma samples was mixed with 25 micro L of 6.8 mol/L Urea, 9.1 mmol/L dithiothreitol and 0.45 micro g/mL lysozyme (chicken egg white) in 50 mmol/L ammonium bicarbonate and incubated for 45 min at 56 degrees C. Then, 2 micro L of 500 mmol/L iodoacetamide was added and incubated for 30 min at 37 degrees C. in the dark. Next, 160 micro L of 0.5 micro g/mL sequencing grade modified trypsin (Promega) in 50 mmol/L ammonium bicarbonate was added and incubated at 37 degrees C. overnight. Finally, 5 micro L of 10% trifluoroacetic acid was added to deactivate any residual trypsin. A 50 micro L of digestion samples were subjected to analysis by LC/ESI-MS/MS. LC/ESI-MS/MS was performed using Xevo TQ-S triple quadrupole instrument (Waters) equipped with 2D I-class UPLC (Waters). Anti-C1s antibody specific peptide GLPSSIEK and human C1s specific peptide LLEVPEGR were monitored by the selected reaction monitoring (SRM). SRM transition was [M+2H]2+ (m/z 415.7) to y6 ion (m/z 660.3) for anti-C1s antibody, and [M+2H]2+(m/z 456.8) to y6 ion (m/z 686.3) for human C1s. Calibration curve was constructed by the weighted (1/x2) linear regression using the peak area plotted against the concentrations. The concentration in mouse plasma was calculated from the calibration curve using the analytical software Masslynx Ver.4.1 (Waters).

Evaluation of Pharmacokinetics for Total hC1s and pH and/or Ca Dependent Anti-C1s Antibody in Mice The in vivo pharmacokinetics of hC1s (human complement component 1s prepared as described in Example 1) and pH and/or Ca dependent antibody prepared in EXAMPLE 2 was assessed after administering hC1s alone or anti-C1s antibody in combination to mice (CB17/Icr-Prkde$^{scid}$/Crl-Crlj: Charles River Japan). Three mice were allocated to each dosing group. hC1s solution (0.23 mg/mL) or a solution of mixture containing hC1s and anti-C1s antibody (0.23 and 2.5 mg/mL, respectively) was injected once at a dose of 10 mL/kg to mice intravenously.

The dose setting was excess concentration of anti-C1s antibody over C1s during the study, and thus almost all C1s was assumed to be bound form in circulation.

Blood was collected at 5, 30 minutes, 2, 7 hours, 3, 7, 14, 21 and 28 days after injection. These blood was centrifuged immediately to separate the plasma samples. Plasma concentration of anti-C1s antibody, hC1s were measured at each sampling points by LC/ESI-MS/MS. PK parameters of anti-C1s antibody and hC1s were estimated by non-compartmental analysis (Phoenix WinNonlin version 8.0, Certara). The following antibodies were administered to mice as anti-C1s antibodies:

1. IPN009VH2/IPN009VK3-SG136,
2. IPN92H0033/IPN009VK3-SG136,
3. IPN009VH2/IPN93L0021-SG136,
4. IPN009VH2/IPN93L0023-SG136,
5. IPN009VH2/IPN93L0024-SG136,
6. IPN92H0038/IPN93L0024-SG136,
7. IPN92H0033/IPN93L0024-SG136,
8. IPN92H0281/IPN93L0024-SG136,
9. IPN92H0286/IPN93L0205-SG136,
10. IPN92H0288/IPN93L0211-SG136,
11. IPN92H0288/IPN93L0058-SG136,
12. IPN92H0307/IPN93L0058-SG136

Plasma antibody time-concentration profile of IPN92H0286/IPN93L0205-SG136 rapidly eliminated from circulation. Highest ECM binding considered to be contributed the rapid elimination. Other pH and/or Ca dependent anti-C1s antibody showed similar plasma time-concentration profiles. CL of IPN92H0286/IPN93L0205-SG136 was 56.5 mL/day/kg, while the CL of other anti-C1s antibodies were within 2-fold range (4.8 to 8.1 mL/day/kg). The results indicates pH and/or Ca dependency does not affect plasma antibody pharmacokinetics.

Plasma hC1s time-concentration profiles of pH and/or Ca dependent anti-C1s antibody showed faster elimination compared to the non-pH/Ca dependent anti-C1s antibody, IPN009VH2/IPN009VK3-SG136. CL of hC1s in pH/Ca dependent anti-C1s antibody tended larger than those of either Ca or pH dependent anti-C1s antibody. These observation indicates pH and Ca dependent binding property or these combination is useful to accelerate C1s elimination in vivo.

Pharmacokinetics Parameters of Mice Co-Injected with Human C1S and Antibody Mixture and the Affinity Values of Antibody Variants The sweeping index of each antibody represents the ability of the antibody variant to clear antigen from the circulation. It was calculated as the antigen clearance rate divided by the antibody clearance rate (Table 8). The sweeping index improvement represents the relative ability of the antibody variant to clear antigen from the circulation as compared to the parent antibody. It is calculated by dividing the sweeping index of each antibody variant by sweeping index of the parent antibody (IPN009VH2/IPN009VK3-SG136), such that the sweeping index of the parent antibody will be 1. The koff (5.8+ of 775+) represents the dissociation rate of C1s during the additional dissociation phase at pH 5.8 which is immediately after the dissociation phase at pH 7.4. The "+" indicates the presence of 1.2 mM CaCl2 at both pH 7.4 and pH 5.8 phases. The column koff (5.8+ of 775+)/koff (7.4) indicate the ratio of the dissociation rate at pH 5.8 to the dissociation rate at pH 7.4 in the 775+ assay. The column KD (5.8+)/KD (7.4+) indicates the ratio of the antibody affinity at pH 5.8 to the affinity at pH 7.4. The "+" indicates the presence of 1.2 mM CaCl2 during affinity measurements at pH 5.8 and pH 7.4. The asterisk mark for affinity values at pH5.8 indicates that the affinity measurements could not be accurately determined due to low binding response.

TABLE 8

| Name of antibody | Ag CL (mL/day/kg) | mAb CL (mL/day/kg) | Sweeping Index Ag CL/ mAb CL | Sweeping Index Improvement (Parental Ab = 1) | kon (7.4+) | koff (7.4+) | KD (7.4+) | koff (5.8+ of 775+) | koff (5.8+ of (775+)/ koff (7.4+) |
|---|---|---|---|---|---|---|---|---|---|
| IPN009VH2/ IPN009VK3-SG136 | 51.5 | 7.2 | 7.1 | 1.0 | 3.44E+05 | 4.11E−04 | 1.19E−09 | 8.86E−05 | 0.2 |
| IPN92H0033/ IPN009VK3-SG136 | 43.7 | 7.5 | 5.9 | 0.8 | 3.77E+05 | 3.80E−04 | 1.01E−09 | 2.65E−04 | 0.7 |
| IPN009VH2/ IPN93L0021-SG136 | 35.3 | 6.1 | 5.8 | 0.8 | 1.99E+05 | 5.80E−04 | 2.92E−09 | 1.10E−03 | 1.9 |
| IPN00VH2/ IPN93L0023-SG136 | 83.1 | 7.2 | 11.5 | 1.6 | 2.27E+05 | 6.28E−04 | 2.77E−09 | 6.91E−04 | 1.1 |
| IPN009VH2/ IPN93L0024-SG136 | 112.4 | 6.8 | 16.5 | 2.3 | 1.80E+05 | 6.12E−04 | 3.40E−09 | 7.41E−04 | 1.2 |
| IPN92H0038/ IPN93L0024-SG136 | 84.2 | 8.1 | 10.4 | 1.5 | 3.84E+05 | 4.61E−04 | 1.20E−09 | 3.54E−03 | 7.7 |
| IPN92H0033/ IPN93L0024-SG136 | 120.8 | 7.7 | 15.6 | 2.2 | 2.27E+05 | 5.71E−04 | 2.51E−09 | 2.90E−03 | 5.1 |
| IPN92H0281/ IPN93L0024-SG136 | 164.7 | 6.0 | 27.3 | 3.8 | 3.19E+05 | 6.45E−04 | 2.02E−09 | 2.47E−02 | 38.2 |
| IPN92H0286/ IPN93L0205-SG136 | 123.2 | 56.5 | 2.2 | 0.3 | 5.74E+05 | 8.22E−04 | 1.43E−09 | 1.34E−02 | 16.3 |
| IPN92H0288/ IPN93L0211-SG136 | 189.4 | 5.9 | 32.1 | 4.5 | 4.69E+05 | 5.20E−04 | 1.11E−09 | 2.82E−02 | 54.2 |
| IPN92H0288/ IPN93L0058-SG136 | 141.1 | 6.1 | 23.1 | 3.2 | 6.66E+05 | 4.08E−04 | 6.11E−10 | 1.58E−02 | 38.8 |
| IPN92H0307/ IPN93L0058-SG136 | 109.8 | 4.8 | 22.9 | 3.2 | 3.91E+05 | 5.23E−04 | 1.34E−09 | 1.51E−02 | 28.8 |

| Name of antibody | kon (5.8+) | koff (5.8+) | KD (5.8+) | KD (5.8+)/ KD (7.4+) | Mutation(s) In VH from IPN009VH2 | Mutation(s) in VL from IPN009VX3 |
|---|---|---|---|---|---|---|
| IPN009VH2/ IPN009VK3-SG136 | 3.60E+05 | 1.62E−04 | 4.49E−10 | 0.4 | — | — |
| IPN92H0033/ IPN009VK3-SG136 | 3.89E+05 | 3.62E−04 | 9.31E−10 | 0.9 | Y99H | — |
| IPN009VH2/ IPN93L0021-SG136 | 2.90E+05 | 1.26E−03 | 4.34E−09 | 1.5 | — | Y92H |
| IPN00VH2/ IPN93L0023-SG136 | 3.30E+05 | 8.18E−04 | 2.48E−09 | 0.9 | — | L94H |
| IPN009VH2/ IPN93L0024-SG136 | 2.21E+05 | 9.56E−04 | 4.32E−09 | 1.3 | — | P95H |
| IPN92H0038/ IPN93L0024-SG136 | 2.89E+05 | 3.09E−03 | 1.07E−08 | 8.9 | G65H/Y99H | P95H |
| IPN92H0033/ IPN93L0024-SG136 | 2.61E+05 | 3.10E−03 | 1.19E−08 | 4.7 | Y99H | P95H |
| IPN92H0281/ IPN93L0024-SG136 | 2.17E+05 | 2.67E−02 | 1.23E−07 | 60.9 | H56K/Y59E/ K64D/G65E/ G98K/Y99H | P95H |
| IPN92H0286/ IPN93L0205-SG136 | * 2.78E+03 | * 2.37E−02 | * 8.53E−06 | N.A | Y32K/G65H/ Y99H | Y32R/Y92H/ L94H |
| IPN92H0288/ IPN93L0211-SG136 | 2.33E+05 | 1.94E−02 | 8.31E−08 | 74.9 | Y59E/K64D/ G98K/ Y99H | S27aE/S30E/ P95H |
| IPN92H0288/ IPN93L0058-SG136 | 3.15E+05 | 1.27E−02 | 4.01E−08 | 65.6 | Y59E/K64D/ G98K/Y99H | S27aE/P95H |
| IPN92H0307/ IPN93L0058-SG136 | 3.18E+05 | 1.21E−02 | 3.81E−08 | 28.4 | T28E/S30E/ Y59E/K64D/ G98K/Y99H | S27aE/P95H |

The correlation between Sweeping Index Improvement and ratio of KD (5.8+)/KD (7.4+) was plotted for all antibodies excluding antibody IPN92H0286/IPN93L0205-SG136 (FIG. 1), as this antibody showed rapid clearance most likely due to high ECM binding (Table 5). The dotted line indicates the line of best fit using linear regression, and R-squared value indicates goodness of fit. The values for KD (5.8+)/KD (7.4+) indicates the ratio of the antibody affinity at pH 5.8 to the affinity at pH 7.4. The "+" indicates the presence of 1.2 mM CaCl2 during affinity measurements at pH 5.8 and pH 7.4.

The correlation between Sweeping Index Improvement and ratio of koff (5.8+ of 775+)/koff (7.4+) was plotted for all antibodies excluding antibody IPN92H0286/IPN93L0205-SG136 (FIG. 2), as this antibody showed rapid clearance most likely due to high ECM binding (Table 5). The dotted line indicates the line of best fit using linear regression, and R-squared value indicates goodness of fit. The values for koff (5.8+ of 775+)/koff (7.4) indicate the ratio of the dissociation rate at pH 5.8 to the dissociation rate at pH 7.4 in the 775+ assay. The "+" indicates the presence of 1.2 mM CaCl2 at both pH 7.4 and pH 5.8 phases.

Example 7

Histidine-substituted variants, IPN93L0026 and IPN92H0012 (Table 9) comprise variable regions with one histidine substitution, e.g., 196H, substitution at position 96 in the light chain and I51H, substitution at position 51 in the heavy chain, respectively, at the Kabat numbering system position. The binding affinity of all histidine-substituted variants at pH 7.4 and pH 5.8 were determined at 37 degrees C. using Biacore T200 instrument (GE Healthcare). Recombinant Protein A/G (Pierce) was immobilized onto all flow cells of a CM4 sensor chip using amine coupling kit (GE Healthcare). Antibodies and analytes were prepared in 7(+) buffer (20 mM ACES, 150 mM NaCl, 1.2 mM CaCl2, 0.05% Tween 20, 0.005% NaN3, pH 7.4) or 5(+) buffer (20 mM ACES, 150 mM NaCl, 1.2 mM CaCl2, 0.05% Tween 20, 0.005% NaN3, pH 5.8). Each antibody was captured onto the sensor surface by protein A/G. Antibody capture levels were aimed at 200 resonance unit (RU). Serum-derived human C1s was injected at 50 nM, followed by dissociation. Sensor surface was regenerated each cycle with 10 mM Glycine-HCl pH 1.5. Binding affinities were determined by processing and fitting the data to 1:1 binding model using Biacore T200 Evaluation software, version 2.0 (GE Healthcare). An additional dissociation phase at pH 5.8 was integrated immediately after the dissociation phase at pH 7.4. This dissociation rate in 5(+) buffer was determined by processing and fitting data using Scrubber 2.0 (BioLogic Software) curve fitting software (Table 9).

As described in Table 9, single histidine-substituted variants, IPN93L0026 and IPN92H0012 showed enhancement in the ratio of koff (5.8+ of 775+)/koff (7.4+). Taking reference from the correlation between Sweeping Index Improvement and ratio of koff (5.8+ of 775+)/koff (7.4+) (Table 8), these substitutions have the potential to enhance Sweeping Index Improvement either alone or in combination with other substitutions.

roacetic acid was added to deactivate any residual trypsin. A 40 micro L of digestion samples were subjected to analysis by LC/ESI-MS/MS. LC/ESI-MS/MS was performed using Xevo TQ-S triple quadrupole instrument (Waters) equipped with 2D I-class UPLC (Waters). Human C1s specific peptide LLEVPEGR was monitored by the selected reaction monitoring (SRM). SRM transition was [M+2H]2+ (m/z 456.8 to y6 ion (m/z 686.4) for human C1s. Calibration curve was constructed by the weighted (1/x2) linear regression using the peak area plotted against the concentrations. The concentration in mouse plasma was calculated from the calibration curve using the analytical software Masslynx Ver.4.1 (Waters).

Evaluation of Pharmacokinetics for Total hC1s after Administration of Anti-C1s Antibodies in Mice The in vivo pharmacokinetics of hC1s and anti-C1s antibodies was assessed after administering antigen alone (mixture of hC1q and rC1r2s2) or with anti-C1s antibody to mice (CB17/Icr-Prkde$^{scid}$/CrlCrlj: Charles River Japan). Three mice were allocated to each dosing group.

Firstly, a solution of mixture containing hC1q and rC1r2s2 (0.84 and 0.47 mg/mL, respectively) was injected at a dose of 10 mL/kg to mice intravenously. After dosing of antigen solution, anti-C1s antibody solution (2.5 mg/mL) was immediately administered to the same individual in the same way.

The dose setting of C1q and rC1r2s2 was designed to be physiological concentration in human plasma just after administration. Dosage of anti-C1s antibody was adjusted to be excess concentration of anti-C1s antibody over both antigens during the study, and thus almost all hC1s was assumed to be bound form in circulation.

TABLE 9

| | kon (7.4+) | koff (7.4+) | KD (7.4+) | Rmax (7.4+) | koff (5.8+ of 775+) | koff (5.8+ of 775+)/ koff (7.4+) |
|---|---|---|---|---|---|---|
| C1_IPN009VH2-SG4GK/IPN009VK3-SK1 | 2.98E+05 | 3.70E-04 | 1.24E-09 | 138.6 | 1.48E-04 | 0.40 |
| C1_IPN009VH2-SG4GK/IPN93L0026-SK1 | 3.50E+05 | 1.50E-03 | 4.28E-09 | 86.1 | 1.15E-03 | 0.77 |
| C1_IPN92H0012-SG4GK/IPN009VK3-SK1 | 1.83E+05 | 1.92E-03 | 1.05E-08 | 75.1 | 1.09E-03 | 0.57 |

Example 8: Mice PK Study Using CCP1-CCP2-SP Binders

Measurement of Total Human C1s Concentration in Mouse Plasma by High-Performance Liquid Chromatography-Electrospray Tandem Mass Spectrometry (LC/ESI-MS/MS)

The total concentrations of human C1s in mouse plasma was measured by LC/ESI-MS/MS. The calibration standards were prepared by mixing and diluting human C1s in defined amounts in mouse plasma, resulting in human C1s concentrations of 0.477, 0.954, 1.91, 3.82, 7.64, 15.3, 30.5 micro g/mL. A 2 micro L of the calibration standards and plasma samples was mixed with 25 micro L of 7.5 mol/L Urea, 8 mmol/L dithiothreitol and 1 micro g/mL lysozyme (chicken egg white) in 50 mmol/L ammonium bicarbonate and incubated for 45 min at 56 degrees C. Then, 2 micro L of 500 mmol/L iodoacetamide was added and incubated for 30 min at 37 degrees C. in the dark. Next, 160 micro L of 0.5 micro g/mL sequencing grade modified trypsin (Promega) in 50 mmol/L ammonium bicarbonate was added and incubated at 37 degrees C. overnight. Finally, 5 micro L of 10% trifluo- Blood was collected at 5, 30 minutes, 2, 7 hours, 3, 7, 14, 21 and 28 days after injection. These blood was centrifuged immediately to separate the plasma samples. Plasma concentrations of hC1s were measured at each sampling points by LC/ESI-MS/MS. PK parameters of hC1s was estimated by non-compartmental analysis (Phoenix WinNonlin version 8.0, Certara). The following antibodies were administered to mice as anti-C1s antibodies (Table 10):

1. COS0098bb-SG1148/SG136
2. COS0112gg-SG1148/SG136
3. COS0127bb-SG1148/SG136
4. COS0158ee-SG1148/SG136
5. COS0182hh-SG1148/SG136

SG136 Fc contains mutations to reduce both C1q and Fc gamma receptor binding. SG1148 Fc contains mutation to reduce C1q binding while retaining Fc gamma receptor binding. PK parameters of hC1s are shown in Table. 11. hC1s CL ratio (SG1148/SG136) of 5 CCP1-CCP2-SP binders (COS0098bb, COS0112gg, COS0127bb, COS0158ee and COS0182hh) was 9.2, 6.9, 5.6, 3.8 and 6.6, respectively. This value indicate potential to accelerate hC1s elimination.

TABLE 10

| Antibody name | SEQ ID NO: | | | | | | | |
|---|---|---|---|---|---|---|---|---|
| | VH | VL | HVR-H1 | HVR-H2 | HVR-H3 | HVR-L1 | HVR-L2 | HVR-L3 |
| COS0098bb | 46 | 51 | 56 | 57 | 58 | 71 | 72 | 73 |
| COS0112gg | 47 | 52 | 59 | 60 | 61 | 74 | 75 | 76 |
| COS0127bb | 48 | 53 | 62 | 63 | 64 | 77 | 78 | 79 |
| COS0158ee | 49 | 54 | 65 | 66 | 67 | 80 | 81 | 82 |
| COS0182hh | 50 | 55 | 68 | 69 | 70 | 83 | 84 | 85 |

Name of constant region: SG1148 (CH: SEQ ID NO: 86 and CL: SEQ ID NO: 88), SG136 (CH: SEQ ID NO: 87 and CL: SEQ ID NO: 88)

TABLE 11

| | C1s CL ratio (SG1148/SG136) |
|---|---|
| COS0098bb | 9.217 |
| COS0112gg | 6.928 |
| COS0127bb | 5.586 |
| COS0158ee | 3.796 |
| COS0182hh | 6.629 |

Sequence Listing C1-A1718Y1Psq_txt

The invention claimed is:

1. An isolated antibody that binds to C1s, wherein the antibody comprises the HVR-H1 sequence of SEQ ID NO: 56, the HVR-H2 sequence of SEQ ID NO: 57 the HVR-H3 sequence of SEQ ID NO: 58, the HVR-L1 sequence of SEQ ID NO: 71, the HVR-L2 sequence of SEQ ID NO: 72, and the HVR-L3 sequence of SEQ ID NO: 73.

2. The antibody of claim 1, comprising a VH sequence of SEQ ID NO:46 and a VL sequence of SEQ ID NO:51.

3. The antibody of claim 1, comprising a variable region which comprises at least one histidine residue.

4. The antibody of claim 1, wherein the antibody is a full-length antibody or a C1s binding antibody fragment.

5. The antibody of claim 4, wherein the antibody is a full-length antibody.

6. The antibody of claim 5, wherein the full-length antibody is a IgG1, IgG2, IgG3 or IgG4 antibody.

7. The antibody of claim 4, wherein the wherein the antibody is a C1s binding antibody fragment.

8. The antibody of claim 7, wherein the C1s binding antibody fragment is a Fv, Fab, Fab', scFv, diabody, or F(ab')2 fragment.

9. The antibody of claim 1, wherein the antibody is a multispecific antibody.

10. The antibody of claim 9, wherein the antibody is a bispecific antibody.

11. The antibody of claim 1, wherein the antibody binds neonatal Fc receptor (FcRn).

12. The antibody of claim 1, wherein the antibody contains a substitution that increases the binding of the antibody to Fc receptor (FcRn).

13. The antibody of claim 1, wherein the antibody contains a substitution at one or more amino acid positions selected from 238, 256, 265, 272, 286, 303, 305, 307, 311, 312, 317, 340, 356, 360, 362, 376, 378, 380, 382, 413, 424 and 434 according to EU numbering.

14. The antibody of claim 1, wherein the antibody comprises a Fc region or a variant Fc region.

15. The antibody of claim 14, wherein the antibody comprises a variant Fc region.

16. The antibody of claim 15, wherein the antibody has reduced effector function.

17. The antibody of claim 16, wherein the antibody contains a substitution at one or more amino acid positions selected from 238, 265, 269, 270, 297, 327 and 329 according to European Union numbering.

18. The antibody of claim 17, wherein the antibody has a substitution at two or more amino acid residues at positions selected from 265, 269, 270, 297 and 327 according to European Union numbering.

* * * * *